US008841471B2

(12) United States Patent
Yaghi et al.

(10) Patent No.: US 8,841,471 B2
(45) Date of Patent: Sep. 23, 2014

(54) OPEN METAL ORGANIC FRAMEWORKS WITH EXCEPTIONAL SURFACE AREA AND HIGH GAS STORAGE CAPACITY

(75) Inventors: Omar M. Yaghi, Los Angeles, CA (US); Jaheon Kim, Seong-Nam (KR); Nakeun Ko, Incheon (KR); Sang Beom Choi, Daejeon (KR); Hiroyasu Furukawa, Los Angeles, CA (US)

(73) Assignees: The Regents of the University of California, Oakland, CA (US); Foundation of Soongsil University-Industry Cooperation, Seoul (KR)

( * ) Notice: Subject to any disclaimer, the term of this patent is extended or adjusted under 35 U.S.C. 154(b) by 252 days.

(21) Appl. No.: 13/496,019

(22) PCT Filed: Sep. 24, 2010

(86) PCT No.: PCT/US2010/050170
§ 371 (c)(1),
(2), (4) Date: Mar. 14, 2012

(87) PCT Pub. No.: WO2011/038208
PCT Pub. Date: Mar. 31, 2011

(65) Prior Publication Data
US 2012/0172612 A1 Jul. 5, 2012

Related U.S. Application Data

(60) Provisional application No. 61/246,065, filed on Sep. 25, 2009.

(51) Int. Cl.
*C07F 3/06* (2006.01)
*C07F 11/00* (2006.01)
*C07F 15/00* (2006.01)
*B01D 15/00* (2006.01)
*C07F 3/00* (2006.01)
*C07C 63/38* (2006.01)
*C07C 63/66* (2006.01)
*C07C 63/331* (2006.01)

(52) U.S. Cl.
CPC ............. *C07F 3/003* (2013.01); *C07C 63/38* (2013.01); *C07C 63/66* (2013.01); *C07C 63/331* (2013.01)
USPC ............. 556/132; 556/49; 556/55; 556/61; 556/106; 556/115; 556/136; 556/147; 210/660; 95/116; 95/141

(58) Field of Classification Search
CPC ............. C07F 1/00; C07F 3/00; C07F 7/00; C07F 11/00; C07F 13/00; C07F 15/00; B01D 15/00; B01D 53/02
USPC ............. 556/49, 55, 61, 106, 115, 132, 136, 556/147; 95/116, 141; 210/660
See application file for complete search history.

(56) References Cited

U.S. PATENT DOCUMENTS

| | | | |
|---|---|---|---|
| 2,684,967 A | 7/1954 | Berg | |
| 4,532,225 A | 7/1985 | Tsao et al. | |
| 5,064,804 A | 11/1991 | Soo et al. | |
| 5,160,500 A | 11/1992 | Chu et al. | |
| 5,208,335 A | 5/1993 | Ramprasad et al. | |
| 5,648,508 A | 7/1997 | Yaghi | |
| 5,733,505 A | 3/1998 | Goldstein et al. | |
| 6,479,447 B2 | 11/2002 | Bijl et al. | |
| 6,501,000 B1 | 12/2002 | Stilbrany et al. | |
| 6,617,467 B1 | 9/2003 | Mueller et al. | |
| 6,624,318 B1 | 9/2003 | Mueller et al. | |
| 6,893,564 B2 | 5/2005 | Mueller et al. | |
| 6,929,679 B2 | 8/2005 | Mueller et al. | |
| 6,930,193 B2 | 8/2005 | Yaghi et al. | |
| 7,196,210 B2 | 3/2007 | Yaghi et al. | |
| 7,202,385 B2 | 4/2007 | Mueller et al. | |
| 7,279,517 B2 | 10/2007 | Mueller et al. | |
| 7,309,380 B2 | 12/2007 | Mueller et al. | |
| 7,343,747 B2 | 3/2008 | Mueller et al. | |
| 7,411,081 B2 | 8/2008 | Mueller et al. | |
| 7,524,444 B2 | 4/2009 | Hesse et al. | |
| 7,582,798 B2 | 9/2009 | Yaghi et al. | |
| 7,637,983 B1 | 12/2009 | Liu et al. | |
| 7,652,132 B2 | 1/2010 | Yaghi et al. | |
| 7,662,746 B2 | 2/2010 | Yaghi et al. | |
| 7,799,120 B2 | 9/2010 | Yaghi et al. | |
| 7,815,716 B2 | 10/2010 | Mueller et al. | |
| 2003/0004364 A1 | 1/2003 | Yaghi et al. | |
| 2003/0078311 A1 | 4/2003 | Mueller et al. | |
| 2003/0148165 A1 | 8/2003 | Mueller et al. | |

(Continued)

FOREIGN PATENT DOCUMENTS

DE 102005023856 A1 11/2006
DE 102005054523 A1 5/2007

(Continued)

OTHER PUBLICATIONS

Wang et al., Inorganic Chemistry, vol. 48, No. 1, pp. 296-306 (2009).*
Wong-Foy et al., Journal of American Chemical Society, vol. 129, No. 51, pp. 15740-15741 (2007).*
Doonan, C., "Hydrogen Storage in Metal-Organic Frameworks," In: Annual Merit Review Proceedings of DOE Hydrogen Program, May 22, 2009.
Young, Jung Doo, International Search Report and Written Opinion, PCT/US2010/050170, Korean Intellectual Property Office, Jun. 8, 2011.
Furukawa et al., "Crystal Structure, Dissolution, and Deposition of a 5 nm Functionalized Metal-Organic Great Rhombicuboctahedron," J. Am. Chem. Soc. 128:8398-8399 (2006).

(Continued)

*Primary Examiner* — Porfirio Nazario Gonzalez
(74) *Attorney, Agent, or Firm* — Joseph R. Baker, Jr.; Gavrilovich, Dodd & Lindsey LLP

(57) ABSTRACT

The disclosure provides metal organic frameworks comprising exception porosity.

20 Claims, 37 Drawing Sheets

(56) References Cited

U.S. PATENT DOCUMENTS

| | | |
|---|---|---|
| 2003/0222023 A1 | 12/2003 | Mueller et al. |
| 2004/0081611 A1 | 4/2004 | Mueller et al. |
| 2004/0225134 A1 | 11/2004 | Yaghi et al. |
| 2004/0249189 A1 | 12/2004 | Mueller et al. |
| 2004/0265670 A1 | 12/2004 | Mueller et al. |
| 2005/0004404 A1 | 1/2005 | Mueller et al. |
| 2005/0014371 A1 | 1/2005 | Tsapatsis et al. |
| 2005/0124819 A1 | 6/2005 | Yaghi et al. |
| 2005/0154222 A1 | 7/2005 | Mueller et al. |
| 2005/0192175 A1 | 9/2005 | Yaghi et al. |
| 2006/0057057 A1 | 3/2006 | Mueller et al. |
| 2006/0135824 A1 | 6/2006 | Mueller et al. |
| 2006/0154807 A1 | 7/2006 | Yaghi et al. |
| 2006/0185388 A1 | 8/2006 | Mueller et al. |
| 2006/0252641 A1 | 11/2006 | Yaghi et al. |
| 2006/0252972 A1 | 11/2006 | Pilliod et al. |
| 2006/0287190 A1 | 12/2006 | Eddaoudi et al. |
| 2007/0068389 A1 | 3/2007 | Yaghi et al. |
| 2007/0202038 A1 | 8/2007 | Yaghi et al. |
| 2007/0248575 A1 | 10/2007 | Conner et al. |
| 2008/0017036 A1 | 1/2008 | Schultink et al. |
| 2008/0184883 A1 | 8/2008 | Zhou et al. |
| 2009/0155588 A1 | 6/2009 | Hesse et al. |
| 2010/0132549 A1 | 6/2010 | Yaghi et al. |
| 2010/0143693 A1 | 6/2010 | Yaghi et al. |
| 2010/0186588 A1 | 7/2010 | Yaghi et al. |
| 2010/0286022 A1 | 11/2010 | Yaghi et al. |
| 2011/0137025 A1 | 6/2011 | Yaghi et al. |

FOREIGN PATENT DOCUMENTS

| | | |
|---|---|---|
| EP | 1674555 A1 | 6/2006 |
| WO | 2004101575 A2 | 11/2004 |
| WO | 2006047423 A2 | 5/2006 |
| WO | 2006072573 A2 | 7/2006 |
| WO | 2006116340 A1 | 11/2006 |
| WO | 2007101241 A2 | 9/2007 |
| WO | 2007111739 A2 | 10/2007 |
| WO | 2008091976 A1 | 7/2008 |
| WO | 2008138989 A1 | 11/2008 |
| WO | 2008140788 A1 | 11/2008 |
| WO | 2009020745 A9 | 2/2009 |
| WO | 2009042802 A1 | 4/2009 |
| WO | 2009/056184 A1 | 5/2009 |
| WO | 2009149381 A3 | 12/2009 |
| WO | 2010056092 A9 | 5/2010 |
| WO | 2010078337 A1 | 7/2010 |
| WO | 2010080618 A1 | 7/2010 |
| WO | 2010083418 A1 | 7/2010 |
| WO | 2010088629 A1 | 8/2010 |
| WO | 2010090683 A1 | 8/2010 |
| WO | 2010148276 A3 | 12/2010 |
| WO | 2010148296 A3 | 12/2010 |
| WO | 2010148374 A3 | 12/2010 |
| WO | 2011014503 A1 | 2/2011 |
| WO | 2011038208 A2 | 3/2011 |
| WO | 2011146155 A9 | 11/2011 |
| WO | 2012012495 A3 | 1/2012 |
| WO | 2012082213 A2 | 6/2012 |
| WO | 2012100224 A3 | 7/2012 |
| WO | 2012106451 A2 | 8/2012 |

OTHER PUBLICATIONS

Furkawa et al., "Independent verification of the saturation hydrogen uptake in MOF-177 and establishment of a benchmark for hydrogen adsorption in metal-organic frameworks," J. Mater. Chem. 17:3197-3204 (2007).

Furukawa et al., "Control of Vertex Geometry, Structure Dimensionality, Functionality, and Pore Metrics in the Reticular Synthesis of Crystalline Metal-Organic Frameworks and Polyhedra," J. Am. Chem. Soc.130:11650-11661 (2008).

Furukawa et al., "Storage of Hydrogen, Methane, and Carbon Dioxide in Highly Porous Covalent Organic Frameworks for Clean Energy Applications," J. Am. Chem. Soc. 25:8876-8883 (2009).

Furukawa et al., "Ultra-High Porosity in Metal-Organic Frameworks," Science 239:424-428 (2010).

Glover et al., "MOF-74 building unit has a direct impact on toxic gas adsorption," J. Chem. Eng. Sci. 66:163-170 (2011).

Gould et al., "The Amphidynamic Character of Crystalline MOF-5: Rotational Dynamics in a Free-Volume Environment," J. Am. Chem. Soc. 130:3246-3247 (2008).

Goebel, Matthias, Supplemental European Search Report and Written Opinion for EP08826913. Date of Completion of Search and Written Opinion: Nov. 10, 2010.

Goebel, Matthias, Supplemental European Search Report and Written Opinion for EP08754337. Date of Completion of Search and Written Opinion: Dec. 3, 2010.

Gonzalez-Arellano et al., "Homogeneous and heterogeneous Au(III) Schiff base-complexes as selective and general catalysts for self-coupling of aryl boronic acids," Chem. Comm. 15:1990-1992 (2005).

Grzesiak et al., "Polymer-Induced Heteronucleation for the Discovery of New Extended Solids," Angew. Chem. Int. Ed. 45:2553-2556 (2006).

Halper et al., "Topological Control in Heterometallic Metal-Organic Frameworks by Anion Templating and Metalloligand Design," J. Am. Chem. Soc. 128:15255-15268 (2006).

Han, SS et al., "Improved designs of metal-organic frameworks for hydrogen storage" Angew. Chem. Int. Ed. 2007, 46, pp. 6289-6292.

Han et al., "Covalent Organic Frameworks as Exceptional Hydrogen Storage Materials," J. Am. Chem. Soc. 130: 11580-11581 (2008).

Hayashi et al., "Zeolite A Imidazolate Frameworks," Nature Materials 6:501-506 (2007).

Hexiang et al., "Multiple Functional Groups of Varying Rations in Metal-Organic Frameworks," Science 327 (5967):846-850 (2010).

Holler et al., "The first dinitrile frameworks of the rare earth elements: [LnCl3(1,4-Ph(CN)2] and [Ln2Cl6(1,4Ph(CN)2], Ln = Sm, Gd, Tb, Y; Access to novel metal-organic frameworks by solvent free synthesis in molten 1,4-benodinitrile," Inorganic Chemistry 47(21): 10141-9 (2008).

Honda, Masashi, International Preliminary Report on Patentability for PCT/US2008/051859. Date of Issuance of the Report: Jul. 28, 2009.

Howe, Patrick. International Search Report and Written Opinion for PCT/US2009/068849. Date of Mailing of the Search Report: Apr. 6, 2010.

Howe, Patrick. International Search Report and Written Opinion for PCT/US2010/022777. Date of Mailing: Jun. 7, 2010.

Huang et al., "Thermal Conductivity of Metal-Organic Framework 5 (MOF-5): Part II. Measurement," Int. J. Heat Mass Transfer 50:405-411 (2007).

Hunt et al., "Reticular Synthesis of Covalent Organic Borosilicate Frameworks," J. Am. Chem. Soc. 130: 11872-11873 (2008).

Isaeva et al., "Metal-organic frameworks—new materials for hydrogen storage," Russian Journal of General Chemistry 77(4):721-739 (2007).

Jeong et al., "Asymmetric Catalytic Reactions by NbO-Type Chiral Metal-Organic Frameworks," Chem. Sci. 2:877-882 (2011).

Kaderi et al., "Designed Synthesis of 3D Covalent Organic Frameworks," Science 316:268-272 (2007).

Kaye et al., "Impact of Preparation and Handling on the Hydrogen Storage Properties of Zn4O(1,4-benzenedicarboxylate)3 (MOF-5)," J. Am. Chem. Soc. 129:14176-14177 (2007).

Kim et al., "Assembly of Metal-Organic Frameworks From Large Organic and Inorganic Secondary Building Units: New Examples and Simplifying Principles for Complex Structures," J. Am. Chem. Soc. 123:8239-8247 (2001).

Kim, Su Mi, International Search Report and Written Opinion for PCT/US2009/068731. Date of Mailing: Aug. 19, 2010.

Kim, Su Mi, International Search Report and Written Opinion, Date of Mailing: Feb. 24, 2010, International Application No. PCT/US09/46463.

Kim, Su Mi. International Search Report for PCT/US2010/039154. Date of Mailing: Feb. 23, 2011.

Kirai et al., "Homocoupling of arylboronic acids catalyzed by 1,10-phenanthroline-ligated copper complexes in air," European Journal of Organic Chemistry 12:1864-1867 (2009).

(56) References Cited

OTHER PUBLICATIONS

Klaes, Daphne. International Search Report and Written Opinion for PCT/US2010/021201. Date of Mailing: Apr. 27, 2010.
Koza et al., "An efficient High Yielding Approach for the Homocoupling of Aryl Boronic Acids," Synthesis 15:2183-2186 (2002).
Kyoungmoo et al., "A Crystalline Mesoporous Coordination Copolymer with High Microporosity," Angew. Chem. Int. Ed. 120:689-692 (2008).
Lee, Ji Min. International Search Report for PCT/US2010/039284. Date of Mailing: Feb. 23, 2011.
Li et al., "Coordinatively Unsaturated Metal Centers in the Extended Porous Framewokr of $Zn_3(BDC)_3$—$6CH_3OH$ (BDC= 1,4-Benzenedicarboxylate)," J. Am. Chem. Soc. 2186-2187 (1998).
Li et al., "Establishing Microporosity in Open Metal-Organic Frameworks: Gas Sorption Isotherms for Zn(BDC) (BDC=1,4-Benzenedicaroxylate)," J. Am. Chem. Soc. 120:8571-8572 (1998).
Li et al., "Porous Germanates: Synthesis, Structure and Inclusion Properties of $Ge_7O14.5F_2$-$[(CH_3)_2NH_2]_3(H_2O)$ O.86," J. Am. Chem. Soc. 120:8567-8568 (1998).
Li et al., "Transformation of Germanium Dioxide to 4-Connected Porous Germanate Net," J. Am. Chem. Soc. 10569-10570 (1998).
Li et al., "An Open-Framework Germanate with Polycubane-Like Topology," Angew. Chem. INt. Ed., 38:653-655 (1999).
Li et al., "Supertetrahedral Sulfide Crystals with Giant Cavities and Channels," Science 283:1145-1147 (1999).
Li et al., "Non-interpenetrating Indium Sulfide with a Supertetrahedral Cristobalite Famework," J. Am. Chem. Soc. 121:6096-6097 (1999).
Li et al., "Design and Synthesis of an Exceptionally Stable and Highly Porous Metal-Organic Framework," Science 402:276-279 (1999); Featured in (1) Chemical and Engineering News (Nov. 22, 1999) and (2) Science News (Nov. 20, 1999).
Li et al., "$Ge_2ZrO6F_2$ ($H_2DAB$)$H_2O$: A 4-Connected Microporous Material with "Bow Tie" Building Units and an Exceptional Proportion of 3-Rings," J. Am. Chem. Soc. 122:12409-12410 (2000).
Li et al., "20 A [$Cd_4In_{16}S_{35}$]14-Supertetrahedral T4 Clusters as Building Units in Decorated Cristobalite Frameworks," J. Am. Chem Soc. 123:4867-4868 (2001).
Li et al., "[$Cd_{16}In_{64}S_{134}$]44-: 31-Å Tetrahedron with a Large Cavity," Angew. Chem. Int. Ed., 42:1819-1821 (2003).
Li et al., "A metal-organic framework replete with ordered donor-acceptor catenanes," Chem. Commun. 46:380-382 (2010).
Li et al., "A Catenated Strut in a Catenated Metal-Organic Framework," Angew. Chem. Int. Ed. 49:6751-6755 (2010).
Li et al., "Docking in Metal-Organic Frameworks", Science, 325, 855 (2009).
Linder, Nora. International Preliminary Report on Patentability for PCT/US2010/022777. Date of Mailing: Aug. 11, 2011.
Burrows et al., "Post-Synthetic Modification of Tagged MOFs," Angew. Chem. Int. Ed. 47:8482-8486 (2008).
Ashton, Peter R. et al. "Hydrogen-Bonded Complexes of Aromatic Crown Ethers with (9-Anthracenyl) methylammonium Derivatives" J. Am. Chem. Soc., 1997, 119 (44), pp. 10641-10651.
Baharlou, Simin. International Preliminary Report on Patentability for PCT/US2009/046463. Date of Mailing: Dec. 16, 2010.
Banerjee et al., "High-Throughput Synthesis of Zeolitic Imidazolate Frameworks and Application to CO2 Capture," Science 319:939-943 (2008).
Banerjee et al., "Control of Pore Size and Functionality in Isoreticular Zeolitic Imidazolate Frameworks and their Carbon Dioxide Selective Capture Properties," J. Am. Chem. Soc. 131:3875-3877 (2009).
Barman et al., "Azulene Based Metal-Organic Frameworks for Strong Adsorption of H2," Chem. Commun. 46: 7981-7983 (2010).
Barton et al., "Tailored Porous Materials," Chem. Mater. 11:2633-2656 (1999).
Bloch et al., "Metal Insertion in a Microporous Metal-Organic Framework Lined with 2,2'-Bipyridine" J. Am. Chem. Soc. 132:14382-14384 (2010).

Braun et al., "1,4-Benzenedicarboxylate Derivatives as Links in the Design of Paddle-Wheel Units and Metal-Organic Frameworks," Chem. Commun. 24:2532-2533 (2001).
Britt et al., "Highly efficient separation of carbon dioxide by a metal-organic framework replete with open metal sites," Proc. Natl. Acad. Sci. USA 106:20637-20640 (2009).
Britt et al., "Ring-Opening Reactions Within Metal-Organic Frameworks," Inorg. Chem. 49:6387-6389 (2010).
Carlucci et al., "Nanoporous three-dimensional networks topologically related to cooperite from the self-assembly of copper(I)centres and 1,2,4,5-tetracyanobenzene," New J. Chem. 23(23):397-401 (1999).
Carlucci, Lucia et al., "Polycatenation, polythreading and polyknotting in coordination network chemistry" Coordination Chemistry Reviews 246, 2003, pp. 247-289.
Caskey et al., "Dramatic Tuning of CO2 Uptake via Metal Substitution in a Coordination Polymer with Cylindrical Pores," JACS 130(33):10870-10871 (2008).
Caskey et al., "Selected Applications of Metal-Organic Frameworks in Sustainable Energy Technologies," Material Matters 4.4:111 (2009).
Centrone et al., "Raman Spectra of Hydrogen and Deuterium Adsorbed on a Metal-Organic Framework," Chem. Phys. Lett. 411:516-519 (2005).
Chae et al., "Tertiary Building Units: Synthesis, Structure, and Porosity of a Metal-Organic Dendrimer Framework (MOD-1)," J. Am. Chem. Soc. 123:11482-11483 (2001).
Chae et al., "Design of Frameworks with Mixed Triangular and Octahedral Building Blocks Exemplified by the Structure of [$Zn_4O(TCA)_2$] Having the Pyrite Topology," Angew. Chem. Int. Ed. 42:3907-3909 (2003).
Chae et al., "A Route to High Surface Area, Porosity and Inclusion of Large Molecules in Crystals," Nature427, 523-527 (2004); Featured in (1) Chemical & Engineering News magazine, Feb. 9, 2004, (2) BBC World Service, Feb. 2004, (3) New Scientist, Feb. 2004.
Chen et al., "$Cu_2(ATC)6H_2O$: Design of Open Metal Sites in Porous Metal-Organic Crystals (ATC: 1,3,5,7-adamantane tetracarboxylate)," J. Am. Chem. Soc. 122:11559-11560 (2000).
Chen et al., "Interwoven Metal-Organic Framework on a Periodic Minimal Surface with Extra-Large Pores," Science 291:1021-1023 (2001); Featured in Chemical and Engineering News, Feb. 21, 2001.
Chen et al., "Transformation of a Metal-Organic Framework from the NbO to PtS Net," Inorg. Chem. 41:181-183 (2005).
Chen et al., "High H2 Adsorption in a Microporous Metal-Organic Framework with Open-Metal Sites," Angew. Chem. Int. Ed. 44:4745-4749 (2005).
Chen et al., "A Microporous Metal-Organic Framework for Gas-Chomatographic Separation of Alkanes," Angew. Chem. Int. Ed. 45:1390-1393 (2006).
Cho et al., "A metal-organic framework material that functions as an enantioselective catalyst for olefin epoxidation," Chem. Comm. 24:2563-2565 (2006).
Choi et al., "Heterogeneity within Order in Crystals of a Porous Metal Organic Framework," J. Am. Chem. Soc. 133:11920-11923 (2011).
Cote et al., "Porous, Crystalline, Covalent Organic Frameworks," Science 310:1166-1170 (2005).
Cote et al., "Reticular Synthesis of Microporous and Mesoporous 2D Covalent Organic Frameworks," J. Am. Chem. Soc. 129:12914-12915 (2007).
Czaja et al., "Industrial applications of metal-organic frameworks," Chemical Society Reviews 38(5):1284-1293 (2009).
Delgado-Friedrichs et al., "Three-Periodic Nets and Tilings: Regular and Quasiregular Nets," Acta Cryst. A59: 22-27 (2003).
Delgado-Friedrichs et al., "Three-Periodic Nets and Tilings: Semiregular Nets," Acta Cryst. A59:515-525 (2003).
Delgado-Friedrichs et al., "The CdSO4, Rutile, Cooperate and Quartz Dual Nets: Interpenetration and Catenation," Solid State Sciences 5:73-78 (2003).
Ockwig et al., "Reticular Chemistry: Occurrence and Taxonomy of Nets, and Grammar for the Design of Frameworks," Acc. Chem. Res. 38:176-182 (2005).
Delgado-Friedrichs et al. "What Do We Know About Three-Periodic Nets?," J. Solid State Chem. 178: 2533-2554 (2005).

(56) References Cited

OTHER PUBLICATIONS

Delgado-Friedrichs et al. "Three-Periodic Nets and Tilings: Edge-Transitive Binodal Structures," Acta Cryst. 62:350-355 (2006).
Delgado-Friedrichs et al., "Taxonomy of Periodic Nets and the Design of Materials," Phys. Chem. 9:1035-1043 (2007).
Demir et al., "Role of Copper Species in the Oxidative Dimerization of Arylboronic Acids: Synthesis of Symmetrical Biaryls," Journal of Organic Chemistry 68(26):10130-10134 (2003).
Deng et al., "Multiple Functional Groups of Varying Ratios in Metal-Organic Frameworks," Science 327:846-850 (2010).
Deng et al., "Robust dynamics" Nature Chem. 2:439-443 (2010).
Doonan et al., "Isoreticular Metalation of Metal-Organic Frameworks," J. Am. Chem. Soc. 131:9492-9493 (2009).
Doonan et al., "Exceptional ammonia uptake by a covalent organic framework," Nature Chem. 2:235-238 (2010).
Duren et al., "Design of New Materials for Methane Storage," Langmuir 20:2683-2689 (2004).
Eddaoudi et al., "Design and Synthesis of Metal-Organic Frameworks with Permanent Porosity," In Topics in Catalysis, G. A. Somorjai and J. M. Thomas, Eds., 9:105 (1999).
Eddaoudi et al., "Highly Porous and Stable Metal-Organic Framework: Structure Design and Sorption Properties," J. Am. Chem. Soc. 121:1391-1397 (2000).
Eddaoudi et al., "Porous Metal-Organic Polyhedra: 25 Å Cuboctahedron Constructed from Twelve $Cu_2(CO_2)_4$ Paddle-Wheel Building Blocks," J. Am. Chem. Soc. 123:4368-4369 (2001).
Eddaoudi et al., "Modular Chemistry: Secondary Building Units as a Basis for the Design of Highly Porous and Robust Metal-Organic Carboxylate Frameworks" Acc. Chem. Res. 34:319-330 (2001).
Eddaoudi et al., "Geometric Requirements and Examples of Important Structures in the Assembly of Square Building Blocks," Proc. Natl. Acad. Sci. 99:4900-4904 (2002).
Eddaoudi et al., "Systematic Design of Pore Size and Functionality in Isoreticular Metal-Organic Frameworks and Application in Methane Storage," Science 295:469-472 (2002): Featured in (1) Chemical and Engineering News, Jan. 21, 2002, and (2) Chemical Insight magazine, Nov. 15, 2002.
Eddaoudi et al., "$Cu_2[o-Br-C_6H_3(CO_2)_2]_2(H_2O)_2 \cdot (DMF)_8(H_2O)_2$: A Framework Deliberately Designed to have the NbO Structure Type," J. Am. Chem. Soc. 124:376-377 (2002).
Ferragut et al., "Positronium Formation in Porous Materials for Antihydrogen Production," J. Phys. Conf. Ser. 225:1-8 (2010).
Llabres et al., "MOFs as catalysts: Activity, reusability and shape-selectivity of a Pd-containing MOF," JOurnal of Catalysis 250(2):294-298, (2007).
Loeb, SJ, "Rotaxanes as ligands: from molecules to materials" Chemical Society reviews, 2007, 36, pp. 226-235.
Long et al., "The Pervasive Chemistry of Metal-Organic Frameworks," Chem. Soc. Rev. 38:1213-1214 (2009).
Lu et al., "Synthesis and Structure of Chemically Stable Metal-Organic Polyhedra," J. Am. Chem. Soc. 131:(35) 12532-12533 (2009).
Mendoza-Cortes et al., "Adsorption Mechanism and Uptake of Methane in Covalent Organic Frameworks: Theory and Experiment," J. Phys. Chem. 114:10824-10833 (2010).
Michalitsch, Richard. International Search Report and Written Opinion for PCT/US2009/069700. Date of Mailing: May 7, 2010.
Millward et al., "Metal-Organic Frameworks with Exceptionally High Capacity for Storage of Carbon Dioxide at Room Temperature," J. Am. Chem. Soc. 127:17998-17999 (2005).
Morris et al., "Crystals as Molecules: Postsynthesis Covalent Functionalization of Zeolitic Imidazolate Frameworks," J. Am. Chem. Soc. 130:12626-12627 (2008).
Morris et al., "A Combined Experimental-Computational Investigation of Carbon Dioxide Capture in a Series of Isoreticular Zeolitic Imidazolate Frameworks," J. Am. Chem. Soc. 132:11006-11008 (2010).
Morris et al., "Postsynthetic Modification of a Metal-Organic Framework for Stabilization of a Hemiaminal and Ammonia Uptake," Inorg. Chem. 50:6853-6855 (2011).
Moyse, Ellen, International Preliminary Report on Patentability and Written Opinion, Date of Issuance of Report: Nov. 17, 2009, International Application No. PCT/US08/006008.
Mulhausen, Dorothee. International Preliminary Report on Patentability for PCT/US2009/069700. Date of Mailing: Jul. 7, 2011.
Mulhausen, Dorothee. International Preliminary Report on Patentability for PCT/US2010/021201. Date of Mailing Jul. 28, 2011.
Ni et al,. "Porous Metal-Organic Truncated Octahedron Constructed from Paddle-Wheel Squares and Terthiophene Links," J. Am. Chem. Soc. 127:12752-12753 (2005).
Nickitas-Etienne, Athina, International Preliminary Report on Patentability and Written Opinion, Date of Issuance of Report: Jan. 19, 2010, International Application No. PCT/US08/70149.
Nickitas-Etienne, Athina. International Preliminary Report on Patentability for PCT/US2008/07741. Date of issuance of this report: Mar. 30, 2010.
Nickitas-Etienne, Athina. International Preliminary Report on Patentability for PCT/US2009/068849. Date of Mailing: Jun. 30, 2011.
Niu et al., "Synthesis and structural characterization of the one dimensional polymers $[Rh_2(OAc)_4(NCPhCN)]S$, S = $CH_3COCH_3$, $CH_3OH$, $C_2H_5OH$, $C_4H_8O$, and $C_6H_6$," Polyhedron 17(23-24):4079-89 (1998).
Novoa, Carlos, International Search Report and Written Opinion for PCT/US2010/021201, European Patent Office. Date of Mailing: Apr. 27, 2010.
Oisaki et al., "A Metal-Organic Framework with Covalently Bound Organometallic Complexes," J. Am. Chem. Soc. 132:9262-9264 (2010).
Wu et al., "Structural Study of New Hydrocarbon Nano-Crystals by Energy-Filtered Electron Diffraction," Ultramicroscopy 98:145-150 (2004).
O'Keefe et al., "Germanate Zeolites: Contrasting the Behavior of Germanate and Silicate Structures Built from Cubic $T_8O_{20}$ units (T = Si or Ge)," Chem. Eur. J. 5:2796-2801 (1999).
O'Keefe et al., "Frameworks for Extended Solids: Geometrical Design Principles," J. Solid State Chem. 152:3-20 (2000).
Okeefe et al., "Reticular Chemistry—Present and Future Prospects—Introduction," J. Solid State Chem.178:V-VI (2005).
O'Keeffe et al., "The Reticular Chemistry Structure Resource (RCSR) Database of, and Symbols for, Crystal Nets," Acc. Chem. Res. 41:1782-1789 (2008).
Park, Kyo Sung et al., "Exceptional chemical and thermal stability of zeolitic imidazolate frameworks," Proc. Natl. Acad. Sci., Jul. 5, 2006, pp. 10186-10191, vol. 103, No. 27.
Park, Jae Woo. International Search Report for PCT/US2010/039123. Date of Mailing: Feb. 24, 2011.
Patteux, Claudine. International Search Report for PCT/US2010/043373. Date of Mailing: Oct. 10, 2010.
Pawsey et al., "Hyperpolarized 129Xe Nuclear Magnetic Resonance Studies of Isoreticular Metal-Organic Frameworks," Phys. Chem. 111:6060-6067 (2007).
Phan et al., "Synthesis, Structure, and Carbon Dioxide Capture Properties of Zeolitic Imidazolate Frameworks," Acc. Chem. Res 43:58-67 (2009).
Phan et al., "Metal-Organic Frameworks of Vanadium as Catalysts for Conversion of Methane to Acetic Acid," Inorg. Chem. 50:7388-7390 (2011).
Plevert et al., "A Flexible Germanate Structure Containing 24-Ring Channels With Very Low Framework Density," J. Am. Chem. Soc. 123:12706-12707 (2001).
Plevert et al., "Synthesis and Characterization of Zirconogermanates," Inorg. Chem., 42:5954-5959 (2003).
Plevert et al., "Layered Structures Constructed from New Linkages of $Ge_7(O,OH,F)_{19}$ Clusters," Chem. Mater. 15:714-718 (2003).
Reineke et al., "From Condensed Lanthanide Coordination Solids to Microporous Frameworks Having Accessible Metal Sites," J. Am. Chem. Soc 121:1651-1657 (1999).
Reineke et al., "A Microporosity of Lanthanide-Organic Frameworks," Angew. Chem. Int. Ed. 38:2590-2594 (1999).

(56) References Cited

OTHER PUBLICATIONS

Reineke et al., "Large Free Volume in Interpenetrating Networks: The Role of Secondary Building Units Exemplified by Tb2(ADB)3[(CH3)2SO]4—16[(CH3)2SO]," J. Am. Chem. Soc. 122:4843-4844 (2000); Featured in Science Magazine, Editors Choice (Nov. 2000).

Rosi et al., "Infinite Secondary Building Units and Forbidden Catenation in Metal-Organic Frameworks," Angew. Chem. Int. Ed. 41:294-297 (2002).

Rosi et al., "Advances in the Chemistry of Metal-Organic Frameworks," CrystEngComm 4:401-404 (2002).

Rosi et al., "Hydrogen Storage in Microporous Metal-Organic Frameworks," Science 300:1127-1129 (2003); Featured in (1) Chemical & Engineering News magazine, May 19, 2004, and (2) Technology Research News Magazine, May 21, 2003.

Rosi et al., "Rod-Packings and Metal-Organic Frameworks Constructed from Rod-Shaped Secondary Building Units," J. Am. Chem. Soc. 127:1504-1518 (2005).

Rowsell et al., "Hydrogen Sorption in Functionalized Metal-Organic Frameworks," J. Am. Chem. Soc.126: 5666-5667 (2004).

Rowsell et al., "Metal-Organic Frameworks: A New Class of Porous Materials," Microporous Mesoporous Mater. 73:3-14 (2004).

Rowsell et al., "Strategies for Hydrogen Storage in Metal-Organic Frameworks," Angew. Chem. Int. Ed. 44: 4670-4679 (2005).

Rowsell et al., "Gas Adsorption Sites in a Large-Pore Metal-Organic Framework," Science 309:1350-1354 (2005).

Rowsell et al., "Characterization of H2 Binding sites in prototypical metal-organic frameworks by inelastic neutron scattering," J. Am. Chem. Soc. 127:14904-14910 (2005).

Rowsell et al., "Effects of Functionalization, Catenation, and Variation of the Metal Oxide and Organic Linking Units on the Low-Pressure Hydrogen Adsorption Properties of Metal-Organic Frameworks," J. Am. Chem. Soc. 128: 1304-1315 (2006).

Siberio-Perez, "Raman Spectroscopic Investigation of CH4 and N2 Adsorption in Metal-Organic Frameworks," Chem. Mater. 19:3681-3685 (2007).

Smaldone et al., "Metal-Organic Frameworks from Edible Nature Products," Angew. Chem. Int. Ed. 49:8630-8634 (2010).

Spencer et al., "Determination of the Hydrogen Absorption Sites in Zn4O(1,4-benzenedicarboxylate) by Single Crystal Neutron Diffraction," Chem. Commun. 3:278-280 (2006); Epub Dec. 6, 2005.

Oisaki et al., "A Metal-Organic Frameowrk with Covalently Bound Organometallic Compliexes," J. of the Amer. Chem. Soc., pp. 9262-9264, vol. 132, No. 27, 2010.

Lawrence, Frank M. Nonfinal Office Action for U.S. Appl. No. 12/699,616. Mail Date Apr. 10, 2012.

Lawrence, Frank M. Nonfinal Office Action for U.S. Appl. No. 12/699,616. Mail Date Aug. 3, 2012.

Lee et al., "Synthesis and Gas Sorption Properties of a Metal-Azolium Framework (MAF) Material," Inorganic Chemistry, Nov. 2, 2009, pp. 9971-9973, vol. 48, No. 21.

Li, Y et al., "Hydrogen Storage in Metal-Organic and Covalent-Organic Frameworks by Spillover," AIChe Journal 54 (1):269-279 (2008).

McKeown et al., "Phthalocyanine-Based Nanoporous Network Polymers," Chem. Comm. 23:2780-2781 (Oct. 31, 2002).

McKeown et al., "Porphyrin-Based Nanoporous Network Polymers," Chem. Comm. 23:2782-2783 (Oct. 31, 2002).

Morris et al., "Framework mobility in the metal-organic framework crystal IRMOF-3: Evidence for aromatic ring and amine rotation," Journal of Molecular Structure 1004:94-101 (2011).

Morris et al., "NMR and X-ray Study Revealing the Rigidity of Zeolitic Imidazolate Frameworks," J. Phys. Chem. 116 (24):13307-13312 (Jun. 1, 2012).

Morris et al., "Synthesis, Structure, and Metalation of Two New Highly Porous Zirconium Metal-Organic Frameworks," Inorg. Chem. 51:6443-6445 (Jun. 7, 2012).

O'Keeffe et al., "Deconstructing the Crystal Structures of Metal-Organic Frameworks and Related Materials into Their Underlying Nets," Chem. Rev. 112(2):675-702 (Feb. 8, 2012).

Park, H. et al., "Synthesis, Structure Determination and Hydrogen Sorption Studies of New Metal-Organic Frameworks Using Triazole and Naphthalenedicarboxylic Acid," Chem. Natur. 19:1302-1308 (2007).

Queen et al., "Site-Specific CO2 Adsorption and Zero Thermal Expansion in an Anisotropic Pore Network," J. Phys. Chem. C, 115:24915-24919 (Nov. 8, 2011).

Rinkel, Bert. Extended European Search Report for European Patent Application EP08713961. Mail Date Jan. 2, 2012.

Rouseau-Jager, Nadia, International Search Report and Written Opinion, PCT/US2011/024671, European Patent Office, Dec. 13, 2011.

Sines, Brian J. Nonfinal Office Action for U.S. Appl. No. 13/142,564. Mail Date Jul. 9, 2012.

Spitler et al., "Lewis Acid Catalyzed Formation of Two-Dimensional Phthalocyanine Covalent Organic Framewokrs." Nature Chem. 2:672-677 (Jun. 20, 2010).

Tilford et al., "Facile Synthesis of a Highly Crystalline, Covalently Porous Boronate Network," 18(22):5296-5301 (Oct. 11, 2006).

Tranchemontagne et al., "Hydrogen Storage in New Metal-Organic Frameworks," J. Phys. Chem. C 116 (24):13143-13151 (May 24, 2012).

Wan et al, "A Belt-Shaped, Blue Luminescent, and Semiconducting Covalent Organic Framework." Angew. Chem. Int. Ed. 47:8826-8830 (2008).

Wan et al., "Covalent Organic Frameworks with High Charge Carrier Mobility," Chem. Mater. 23:4094-4097 (Aug. 22, 2011).

Young, Jung Doo. International Search Report and Written Opinion for PCT/US2011/053423. Date of mailing of ISR Jul. 23, 2012.

Young, Jung Doo. International Search Report and Written Opinion for PCT/US2012/022114. Date of mailing of ISR Aug. 22, 2012.

Young, Jung Doo, "International Search Report and Written Opinion for PCT/2012/023516." Date of mailing of the International Search Report Oct. 19, 2012.

Zhang, J. et al., "Exceptional Framework Flexibility and Sorption Behavior of a Multifunctional Porous Cuprous Triazolate Framework," J. Am. Chem. Soc. 130:6010-6017 (2008).

Zhou, X et al., "Hydrothermal Syntheses and Structures of Three Novel Coordination Polymers Assembled from 1,2,3-Triazolate Ligands," CrystEngComm. 11:1964-1970 (2009).

Zhou et al., "Introduction to Metal-Organic Frameworks," Chemical Reviews 112:673-674 (Jan. 26, 2012).

Zhu, A. et al., "Isomeric Zinc(II) Triazolate Frameworks with 3-Connected Networks: Syntheses, Structures, and Sorption Properties," Inorg. Chem. 48:3882-3889 (2009).

Costa et al., "Chemical Modification of a Bridging Ligand Inside a Metal-Organic Framework while Maintaining the 3D Structure," Eur. J. Inorg. Chem. 10:1539-1545 (2008).

Cui et al., "IIn Situ Hydrothermal Growth of Metal-Organic Framework 199 Films on Stainless Steel Fibers for Solid-Phase Microextraction of Gaseous Benzene Homologues," Anal. Chem. 81(23):9771-9777 (2009).

Dugan et al., "Covalent modification of a metal-organic framework with isocyanates: probing substrate scope and reactivity," 29:3366-3368 (2008).

Luo et al., "Two new metal-triazole-benzenedicarboxylate frameworks affording an uncommon 3,4-connected net and unique 4,6-connected rod packing: hydrothermal synthesis, structure, thermostability and luminescence studies," CrystEngComm 11(6):1097-1102 (2009).

Galli et al., "Adsorption of Harmful Organic Vapors by Flexible Hydrophobic Bis-pyrazolate Based MOFs," Chem. Mater. 22(5):1664-1672 (2010).

Ingleson et al., "Framework fractionalization triggers metal complex binding," Chem. Comm. 23:2680-2682 (2008).

Li et al., "Synthesis and Structural Characterization of a New 3D Lead Coordination Polymer with a Tetrazole-1-acetate Ligand," Chinese J. Struct. Chem. 30(7):1049-1053 (2011).

Ling et al., "A zinc(II) metal-organic framework based on triazole and dicarboxylate ligands for selective adsorption of hexane isomers," Chem. Comm. 47:7197-7199 (2011).

(56) References Cited

OTHER PUBLICATIONS

Natarajan et al., "Non-carboxylate based metal-organic frameworks (MOFs) and related aspects," Current Opinion in Solid State and Materials Science 13(3-4):46-53 (2009).
Nickitas-Etienne, Athina, International Preliminary Report on Patentability for PCT/US2009/068731. Date of Issuance of the Report: Jun. 21, 2011.
Peterson et al., "Ammonia Vapor Removal by Cu3(BTC)2 and Its Characterization by MAS NMR," J. Phys. Chem. C. 113(32):13906-13917 (2009).
Seo et al., "A homochiral metal-organic porous material for enantioselective separation and catalysis," Nature 404:982-986 (2000).
Song et al., "A Multiunit Catalyst with Synergistic Stability and Reactivity: A PolyoxometalateMetal Organic Framework for Aerobic Decontamination," J. Am. Chem. Soc. 133(42):16839-16846 (Sep. 13, 2011).
Song et al., "Hydrothermal Synthesis and Structural Characterization of Three-dimensional Metal-organic Framework [Zn3(C2H2N3)2(C7H5O2)4]," Chem. Res. Chinese Universities 25(1):1-4 (2009).
Tanabe et al., "Systematic Functionalization of a Metal-Organic Framework via a Postsynthetic Modification Approach," J. Am. Chem. Soc. 130(26):8508-8517 (2008).
Vitillo et al., "Role of Exposed Metal Sites in Hydrogen Storage in MOFs," J. Am. Chem. Soc. 130(26):8386-8396 (2008).
Wang et al., "Postsynthetic Covalent Modification of a Neutral Metal-Organic Framework," J. Am. Chem. Soc. 129(41):12368-12369 (2007).
Wang et al., "Tandem Modification of Metal-Organic Frameworks by a Postsynthetic Approach," Angew. Chem. Int. 47:4699-4702 (2008).
Yaghi, Omar., "Porous Crystals for Carbon Dioxide Storage," slide presentation at the Fifth Annual Conference on Carbon Capture & Sequestration, US Department of Energy on May 10, 2006 http://www.netl.doe.gov/publications/proceedings/06/carbon-seq/Tech%20Session%20193.pdf.
Yaghi, Omar, "Hydrogen Storage in Metal-Organic Frameworks," slide presentation to DOE Hydrogen Program 2007 Annual Merit Review, US Department of Energy, on May 15, 2007 at http://www.hydrogen.energy.gov/pdfs/review07/st_10_yaghi.pdf.
Yang et al., "Four Novel Three-Dimensional Triazole-Based Zinc(II) Metal-Organic Frameworks Controlled by the Spacers of Dicarboxylate Ligands: Hydrothermal Synthesis, Crystal Structure, and Luminescence Properties," Crystal Growth Design 7(10):2009-2015 (2007).
Yang et al. "Two Novel Triazole-Based Metal-Organic Frameworks Consolidated by a Flexible Dicarboxylate Co-ligand: Hydrothermal Synthesis, Crystal Structure, and Luminescence Properties," Australian Journal of Chemistry 61(10):813-820 (2008).
Zhang et al., "Crystal engineering of binary metal imidazolate and triazolate frameworks," Chem. Comm. 1689-1699 (2006).
Zhang et al., "Syntheses, Structures, and Porous/Luminescent Properties of Silver 3-Alkyl-1,2,4-Triazolate Frameworks with Rare 3-Connected Topologies," Crystal Growth and Design 11:796-802 (2011).
Adkins, Chinessa T. Nonfinal Office Action for U.S. Appl. No. 12/524,205. Mail Date Apr. 17, 2012.
Adkins, Chinessa T. Final Office Action for U.S. Appl. No. 12/524,205. Mail Date Sep. 27, 2012.
Barman et al., "Incorporation of active metal sites in MOFs via in situ generated ligand deficient metal—linker complexes" Chem. Commun. 47:11882-11884 (Oct. 11, 2011).
Bork, Ana-Marie., International Search Report for PCT/US2011/24671, European Patent Office, Nov. 30, 2011.
Burrows et al., "Post-Synthetic Modivication fo Tagged Metal-Organic Frameworks," Angew. Chem Int'l., 2008, pp. 8482-8486, vol. 47.

Chen et al., "Noncovalently Netted, Photoconductive Sheets with Extremely High Carrier Mobility and Conduction Anisotropy from Triphenylene-Fused Meetal Trigon Conjugates," In. J. Am. Chem. Soc. 131:7287-7297 (2009).
Choi et al., "Reversible Interpenetration in a Metal-Organic Framework Triggered by Ligand Removal and Addition," Angew. Chem. Int. Ed. 51:8791-8795 (2012).
Coskun et al., "Metal-Organic Frameworks Incorporating Copper-Complexed Rotaxanes," Angew. Chem. Int. Ed., 51:2160-2163 (2012).
Chun et al., "Concomitant Formation of N-Heterocyclic Carbene—Copper Comlexies within a Supramolecular Network in the Self-Assembly of Immidzolium Dicarboxylate with Metal Ions," Inorganic Chemistry, Jul. 20, 2009, pp. 6353-6355, vol. 48, No. 14.
Chun et al., Cu2O: A versatile Reagent for Base-Free Direct Synthesis of NHC—Copper Complexes and Decoration of 3D-MOF with Coordinatively Unsaturated NHC-Copper Species, Organometallics, Mar. 16, 2010, pp. 1518-1521, vol. 29, No. 7.
Cordero Garcia, Marcela M. Nonfinal Office Action for U.S. Appl. No. 12/680,141. Mail Date Nov. 2, 2012.
Crees et al., "Synthesis of a Zinc(II) Imidazolium Dicarboxylate Logand Metal-Organic Framework (MOF): a Potential Precursor to MOF-Tethered N-Heterocyclic Carbene Compounds," Inorganic Chemistry, pp. 1712-1719, vol. 49, No. 4, 2009.
Demessence, A et al., "Strong CO2 Bnding in a Water-Stable, Triazolate-Bridged Metal-Organic Framework Functionalized with Ethylenediamine," J. Am. Chem. Soc. 131:8784-8786 (2009).
Deng et al., "Large-Pore Apertures in a Series of Metal-Organic Frameworks," Science 336:1018-1023 (May 25, 2012).
Fei et al., "A Nearly Planar Water Sheet Sandwiched between Strontium—Imidazolium Carboxylate Coordination Polymers," Inorg. Chem., 2005, pp. 5200-5202, vol. 44.
Fracaroli et al., "Isomers of Metal-Organic Complex Arrays," Inorg. Chem. 51: 6437-6439 (Jun. 5, 2012).
Furukawa et al., "Isoreticular Expansion of MetalOrganic Frameworks with Triangular and Square Building Units and the Lowest Calculated Density for Porous Crystals," Inorg. Chem. 50:9147-9152 (2011).
Gadzikwa, T. et al., "Selective Bifunctional Modification of a Non-catenated Metal-Organic Framework Material via Click Chemistry," J. Am. Chem. Soc. 131:13613-13615 (2009).
Gandara et al., "Porous, Conductive Metal-Triazolates and Their Structural Elucidation by the Charge-Flipping Method," Chem. Eur. J. 18:10595-10601 (2012).
Gassensmith et al., "Strong and Reversible Binding of Carbon Dioxide in a Green Metal-Organic Framework," J. Am. Chem. Soc. 133:15312-15315 (Aug. 30, 2011).
Goto, Yet al., "Clickable Metal-Organic Framework," J. Am. Chem. Soc. 130:14354-14355 (2008).
Hmadeh et al., "New Porous Crystals of Extended Metal-Catecholates," J. Chem. Mater. 24:3511-3513 (Aug. 28, 2012).
Jones, Christopher. Nonfinal Office Action for U.S. Appl. No. 12/598,855. Mail Date Jun. 14, 2012.
Jones, Christopher. Nonfinal Office Action for U.S. Appl. No. 12/598,855. Mail Date Oct. 12, 2012.
Koh et al., "A Crystalline Mesoporous Coordination Copolymer with High Microporosity," Angew Chem Int'l, 2008, pp. 677-680, vol. 47.
Stallmach et al., "NMR Studies on the Diffusion of Hydrocarbons on the Metal-Organic Framework Material MOF-5," Angew. Chem. Int. Ed. 45:2123-2126 (2006).
Sudik et al., "Design, Synthesis, Structure, and Gas (N2, Ar, CO2, CH4 and H2) Sorption Properties of Porous Metal-Organic Tetrahedral and Heterocuboidal Polyhedra," J. Am. Chem. Soc. 127:7110-7118 (2005).
Sudik et al., "Metal-Organic Frameworks Based on Trigonal Prismatic Building Blocks and the New "acs" Topology," Inorg. Chem. 44:2998-3000 (2005).
Sudik et al., "A Metal-Organic Framework with a Hierarchical System of Pores and Tetrahedral Bbuilding Blocks," Angew. Chem. Int. Ed. 45:2528-2533 (2006).
Tranchemontagne et al. "Metal-Organic Frameworks with High Capacity and Selectivity for Harmful Gases," Proc. Natl. Acad. Sci. USA 105:11623-11627 (2008).

(56) References Cited

OTHER PUBLICATIONS

Tranchemontagne et al., "Reticular Chemistry of Metal-Organic Polyhedra," Angew. Chem. Int. Ed., 2008, 47:5136-5147 (2008).
Tranchemontagne et al., "Room Temperature Synthesis of Metal-organic Frameworks: MOF-5, MOF-74, MOF-177, MOF-199, and IRMOF-0," Tetrahedron 64:8553-8557 (2008).
Tranchemontagne et al. "Secondary Building Units, Nets and Bonding in the Chemistry of Metal-Organic Frameworks," Chem. Soc. Rev. 38:1257-1283 (2009).
Uribe-Romo et al., "A Crystalline Imine-Linked 3-D Porous Covalent Organic Framework," J. Am. Chem. Soc. 131:4570-4571 (2009).
Uribe-Romo et al., "Crystalline Covalent Organic Frameworks with Hydrazone Linkages," J. Am. Chem. Soc. 133: 11478-11481 (2011).
Vairaprakash et al., "Synthesis of Metal-Organic Complex Arrays," J. Am. Chem. Soc. 133:759-761 (2011).
Valente et al., "Metal-organic Frameworks with Designed Chiral Recognition Sites," Chem. Commun. 46: 4911-4913 (2010).
Vodak et al., "Metal-Organic Frameworks Constructed from Pentagonal Antiprismatic and Cuboctahedral Secondary Building Units," Chem. Commun. 2534-2535 (2001).
Vodak et al., "One-Step Synthesis and Structure of an Oligo(spiro-orthocarbonate)," J. Am. Chem. Soc.124(18):4942-4943 (2002).
Vodak et al., "Computation of Aromatic C3N4 Networks and Synthesis of the Molecular Precursor N(C3N3)3C16," Chem. Eur. J. 9:4197-4201 (2003).
Walton et al., "Understanding Inflections and Steps in Carbon Dioxide Adsorption Isotherms in Metal-Organic Frameworks," J. Am. Chem. Soc.130:406-407 (2008).
Wang et al., "Colossal Cages in Zeolitic Imidazolate Frameworks as Selective Carbon Dioxide Reservoirs," Nature 453:207-211 (2008).
Wong-Foy, AG et al., "Exceptional H2 saturation uptake in microporous metal-organic frameworks" J. Am. Chem. Soc., 2006, 128, pp. 3494-3495.
Yaghi et al., "Selective binding and removal of guests in a microporous metal-organic framework," Nature, Dec. 1995, pp. 703-706, vol. 378.
Yaghi et al., "Conversion of Hydrogen-Bonded manganese(II) and zinc(II) squarate (C4O42-) molecules, Chains, and Sheets to 3-D Cage Networks," J. Chem. Soc., Dalton Trans., 1995, 727-732.
Yaghi et al., "Presence of Mutually Interpenetrating Sheets and Channels in the Extended Structure of Cu(4,4'-Bipyridine)Cl," Angew. Chem. Int. Ed. Engl., 1995, 34, 207-209.
Yaghi et al., "The Utility of Polymeric Matrices in the Preparation of Single Crystals of Coordination Solids: Synthesis and Structure of CuII(1,4-C4H4N2)(C4O4)(OH2)4," J. Solid State Chem., 1995, 117, 256-260.
Yaghi et al., "Open-Framework Solids with Diamond-Like Structures Prepared from Clusters and Metal-Organic Building Blocks," Mater. Res. Soc. Symp. Proc., 1995, 371, 15.
Yaghi et al., "Hydrothermal Synthesis of a Metal-Organic Framework Containing Large Rectangular Channels," J. Am. Chem. Soc., 1995, 117, 10401-10402.
Yaghi et al., "Construction of Microporous Materials from Molecular Building Blocks," Fundamental Materials Research, T. J. Pinnavaia and M. F. Thorpe, eds., vol. II, Plenum: New York, p. 111 (1995).
Yaghi et al., "T-Shaped Molecular Building Units in the Porous Structure of Ag(4,4'-bpy) NO3," J. Am. Chem. Soc., 1996, 118, 295-296.
Yaghi et al., "Construction of Porous Solids from Hydrogen-Bonded Metal Complexes of 1,3,5-Benzenetricarboxylic Acid," J. Am. Chem. Soc., 1996, 118, 9096-9101.

Yaghi et al., "Conversion of Molecules and Clusters to Extended 3-D Cage and Channel Networks," Metal Containing Polymeric Materials, C. U. Pittman, C. E. Carraher, B. M. Culbertson, M. Zeldin, J. E. Sheets, Eds., Plenum: New York, p. 219 (1996).
Yaghi et al., "Selective Guest Binding by Tailored Channels in a 3-D Porous Zinc(II)-1,3,5-Benzenetricarboxylate Network," J. Am. Chem. Soc., 1997, 119, 2861-2868.
Yaghi et al., "Crystal Growth of Extended Solids by Nonaqueous Gel Diffusion," Chem. Mater., 1997, 9, 1074-1076.
Yaghi et al., "A Molecular Railroad with Large Pores: Synthesis and Structure of Ni(4,4'-bpy)2.5(H2O)2(ClO4)2•1.5(4,4'-bpy)2(H2O)," Inorg. Chem., 1997, 36, 4292-4293.
Yaghi et al., "Construction of a New Open-Framework Solid form 1,3,5-Cyclohexanetricarboxylate and Zinc(II) Building Blocks," J. Chem. Soc. Dalton Trans. 2383-2384 (1997).
Yaghi et al., "Synthesis and Structure of a Metal-Organic Solid Having the Cadmium (II) Sulfate Net," Mater. Res. Soc. Symp. Proc. 453:127 , (1997).
Yaghi et al., "Designing Microporosity in Coordination Solids," Modular Chemistry, J. Michl, Ed., Kluwer: Boston, p. 663 (1997).
Yaghi et al., "Synthetic Strategies, Structure Patterns, and Emerging Properties in the Chemistry of Modular Porous Solids," Acc. Chem. Res. 31:474-484 (1998).
Yaghi et al., "Transformation of Germanium Dioxide to 4-Connected Porous Germanate Net," J. Am. Chem. Soc., 20:10569-10570 (1998).
Yaghi et al., "Design of Solids from Molecular Building Blocks: Golden Opportunities for Solid State Chemistry," J. Solid State Chem. 152, 1-2 (2000).
Yaghi et al., "A Molecular World Full of Holes," Chem. Innov. p. 3 (2000).
Yaghi et al., "Reticular Synthesis and the Design of New Materials," Nature 423:705-714 (2003).
Yaghi et al., "Metal-Organic Frameworks: A Tale of Two Entanglements," Nature materials 6:92-93 (2007).
Yaghi et al., "Reticular Chemistry and Metal-Organic Frameworks for Clean Energy," MRS Bulletin 34:682-690 (2009).
Young, Lee W., International Search Report and Written Opinion, Date of Mailing of Report: May 7, 2008, International Application No. PCT/US08/51859.
Young, Lee W., "International search Report and Written Opinion," PCT/US08/06008, United States Patent & Trademark Office, Aug. 20, 2008.
Young, Lee W., International Search Report and Written Opinion, Date of Mailing: Dec. 2, 2008, International Application No. PCT/US08/77741.
Young, Lee W., International Search Report and Written Opinion, Date of Mailing: Jan. 12, 2009, International Application No. PCT/US08/70149.
Zhang et al., "Docking in Metal-Organic Frameworks," Science 325:855-859 (2009).
Zhao et al., "Rigid-Strut-Containing Crown Ethers and [2]Catenanes for Incorporation into Metal-Organic Frameworks," Chem. Eur. J. 15:13356-13380 (2009).
Zhao, Wei. The First Office Action for Chinese Application No. 200880003157.2. The State Intellectual Property Office of the People's Republic of China. Issue Date: Aug. 5, 2011.
Zhofu et al., "A Nearly Planar Water Sheet Sandwiched between Strontium—Imidazolium Carboxylate Coordination Polymers," Inorg. Chem. 44:5200-5202 (2005).

\* cited by examiner

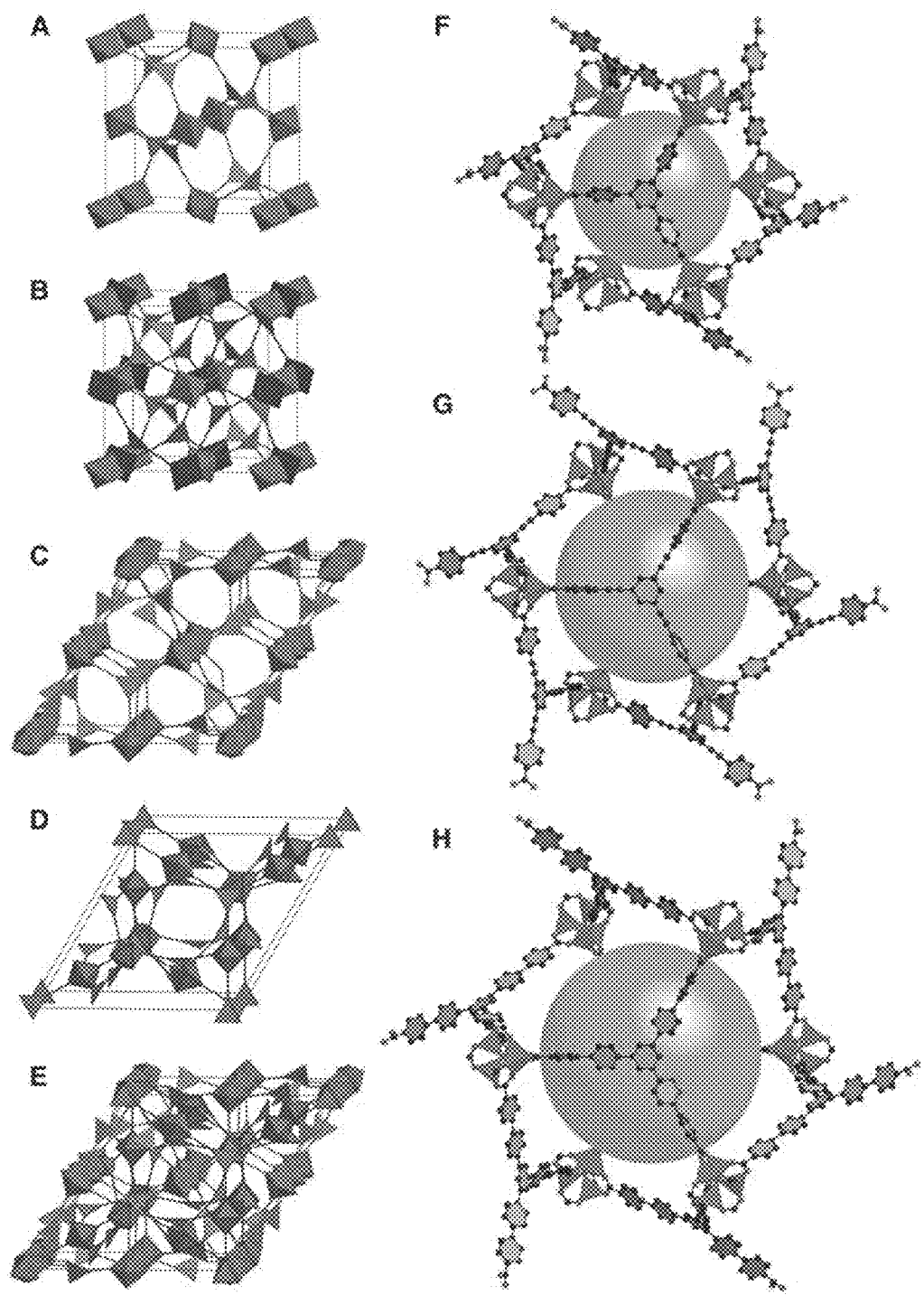
FIGURE 1A-H

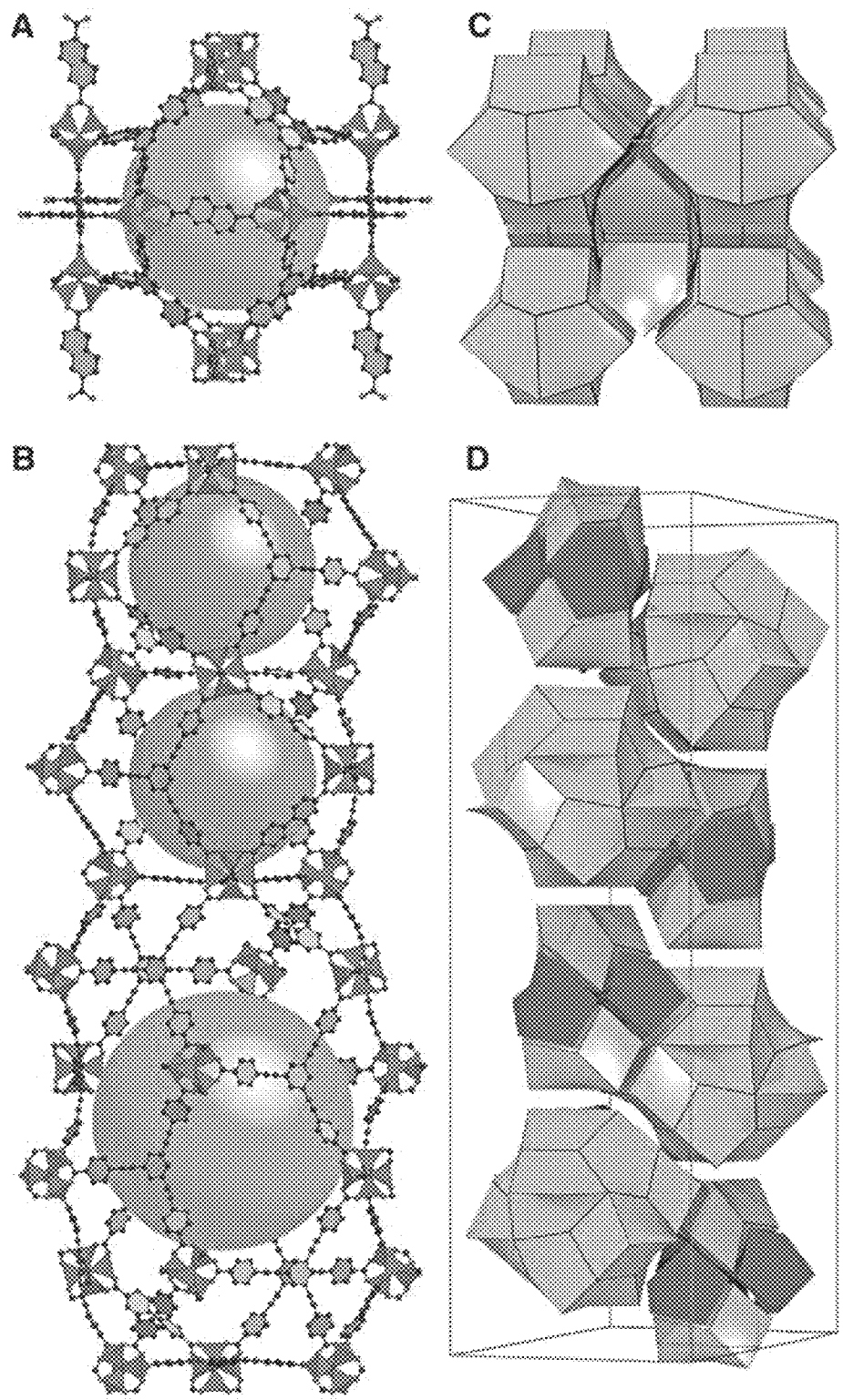
FIGURE 2A-D

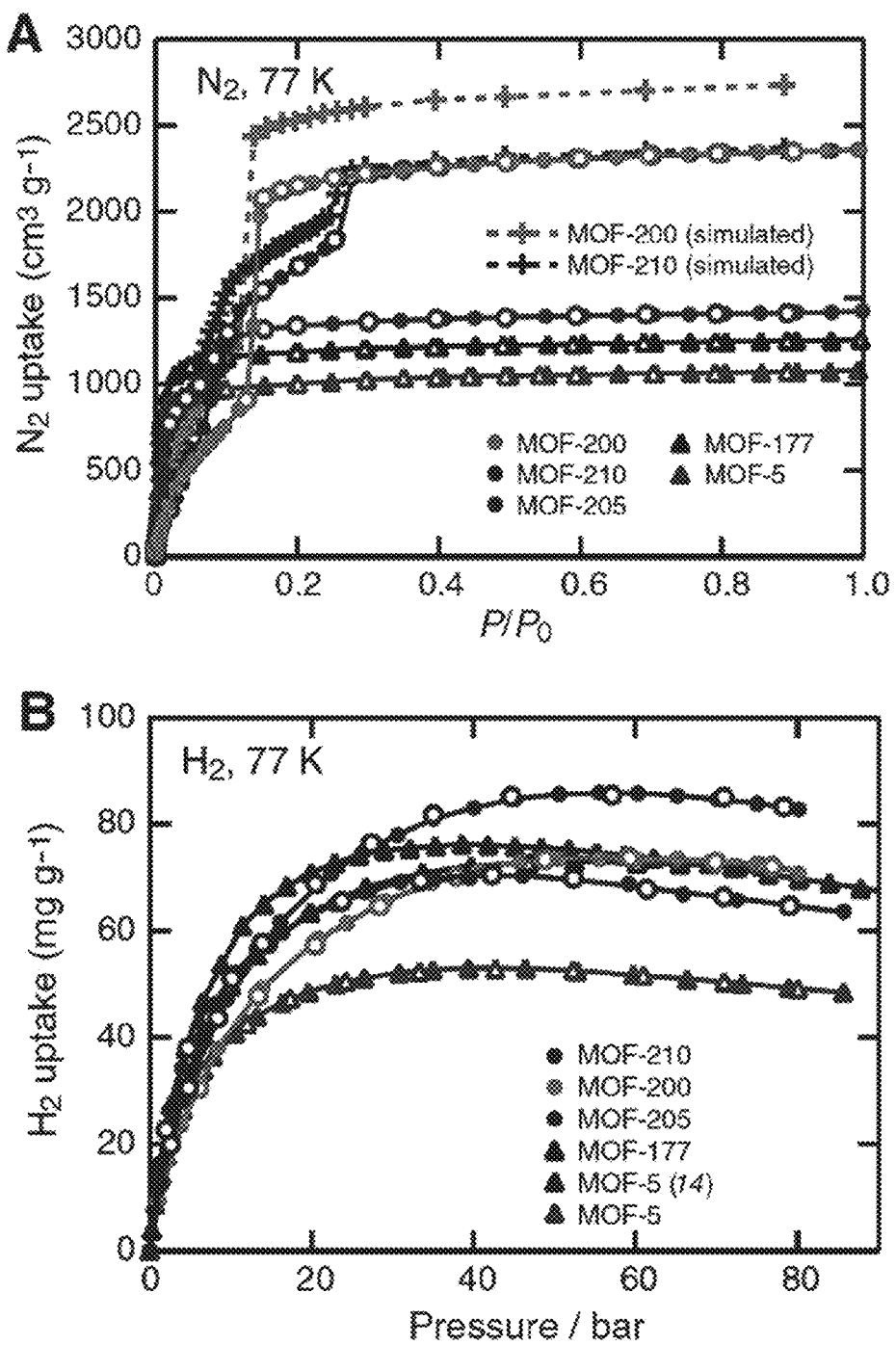
FIGURE 3A-B

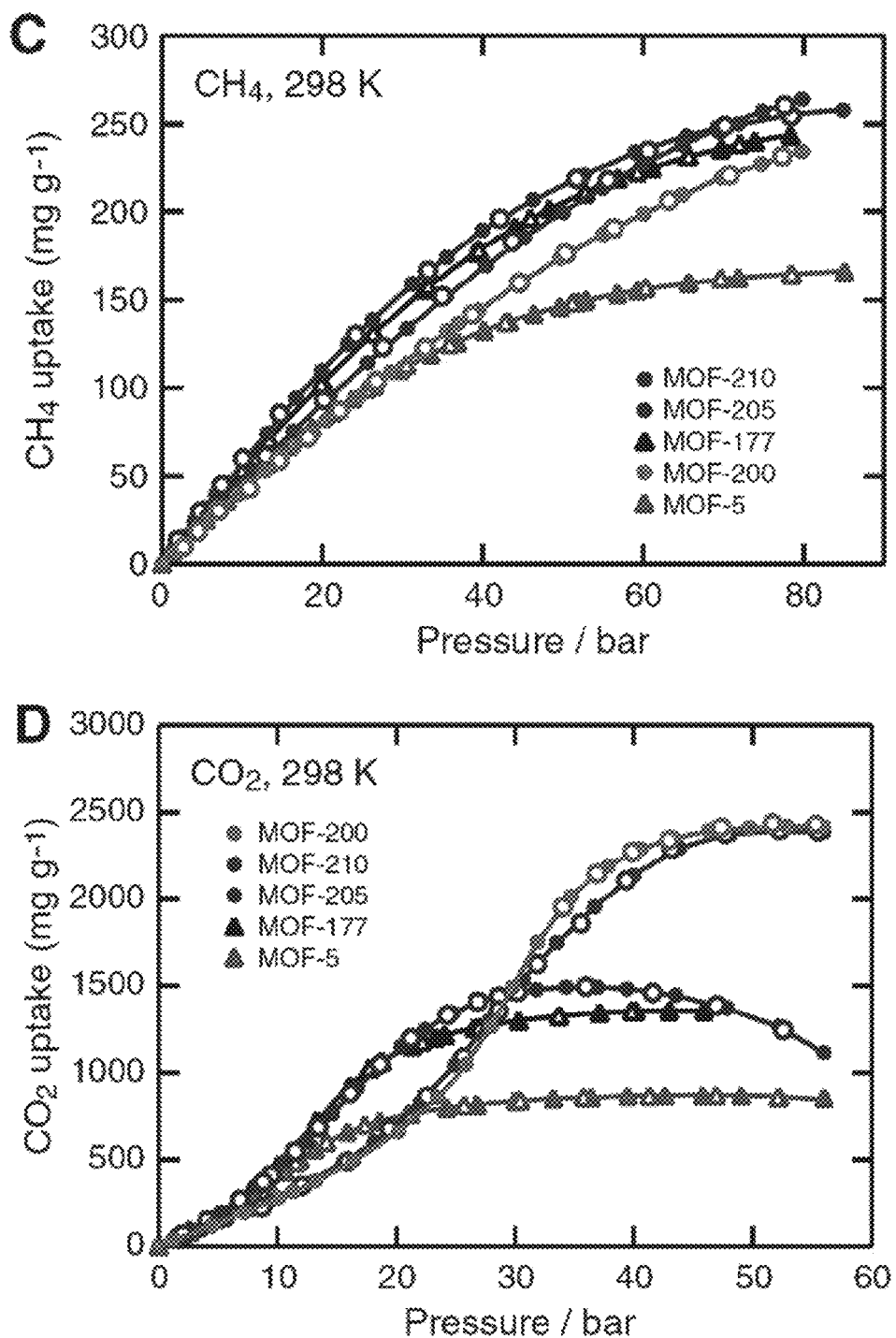
FIGURE 3C-D

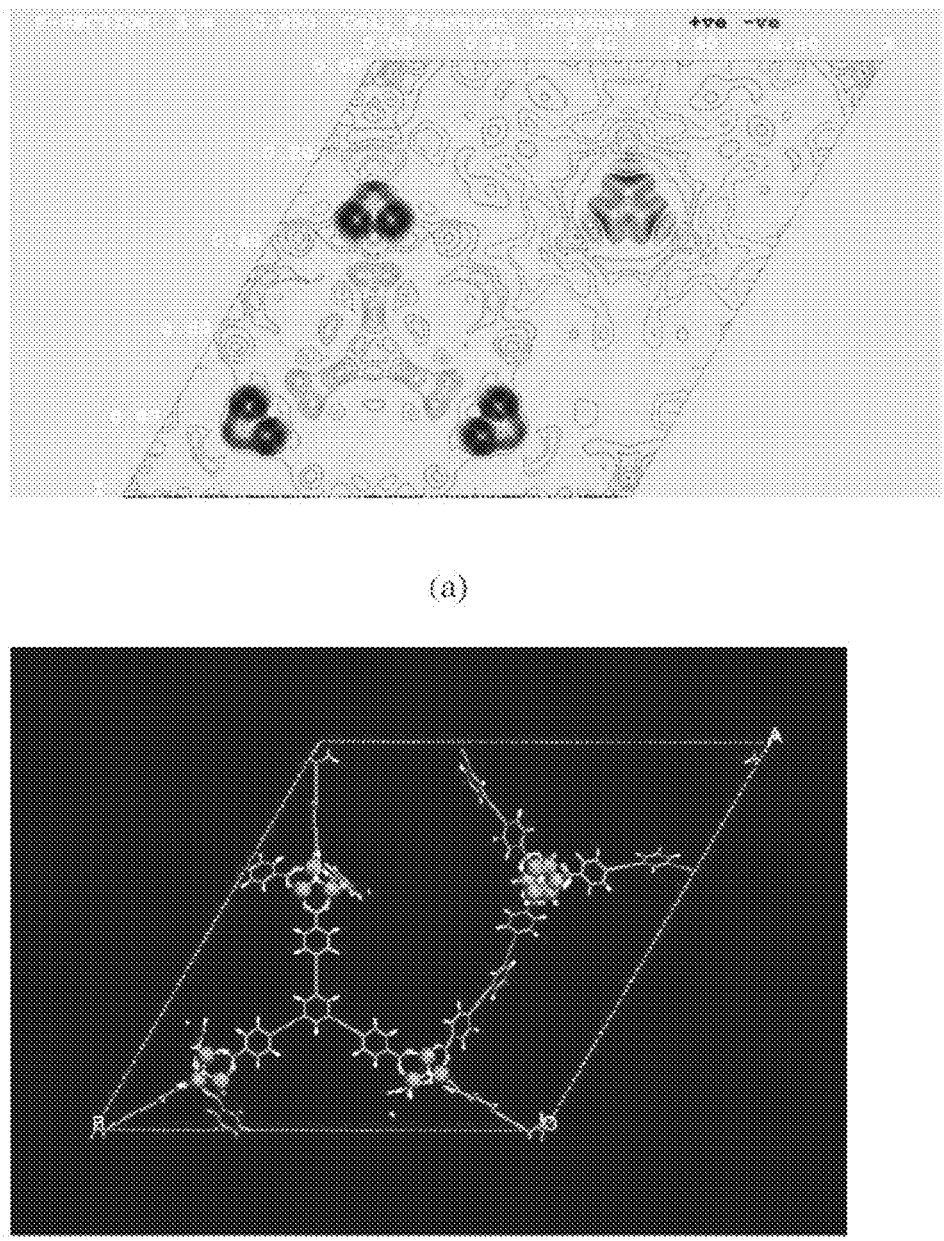
FIGURE 4A-B

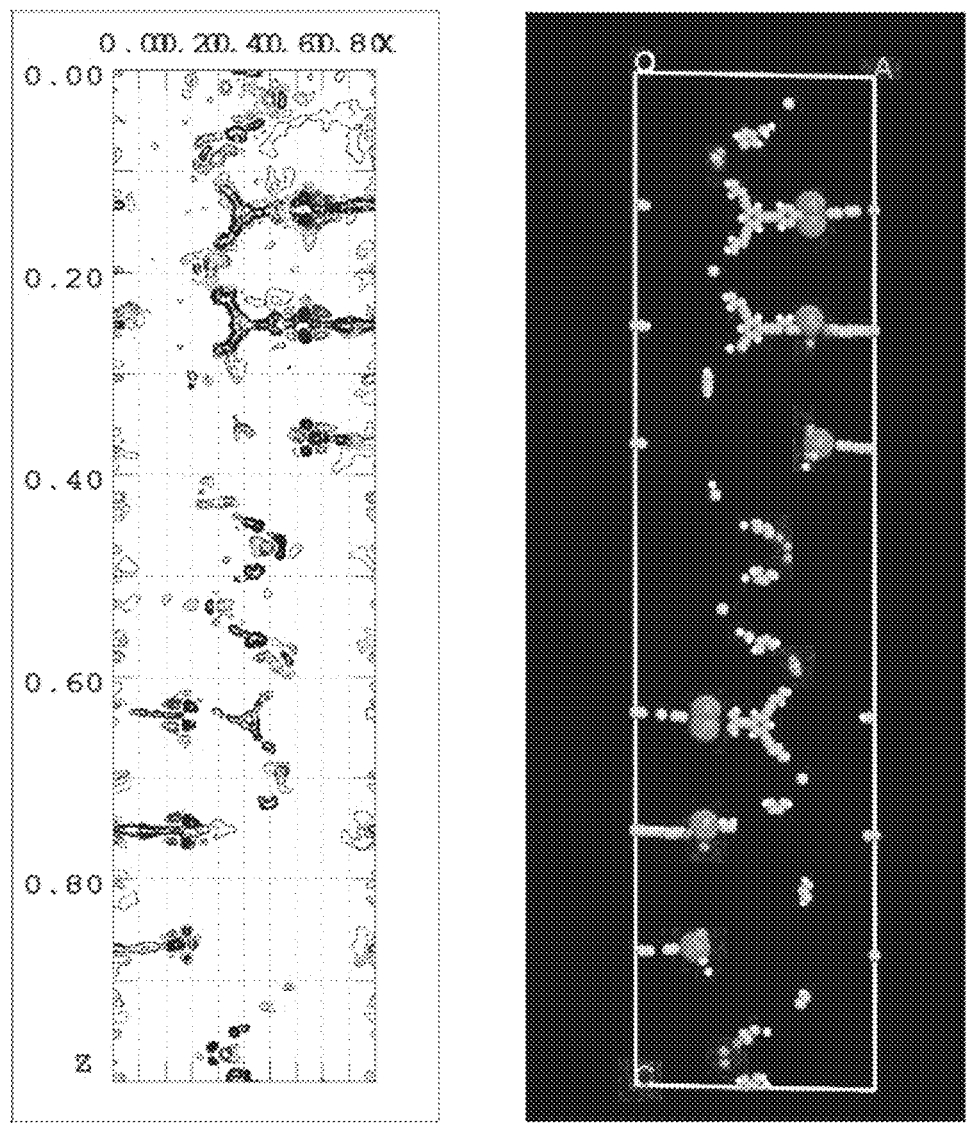
FIGURE 8A-B

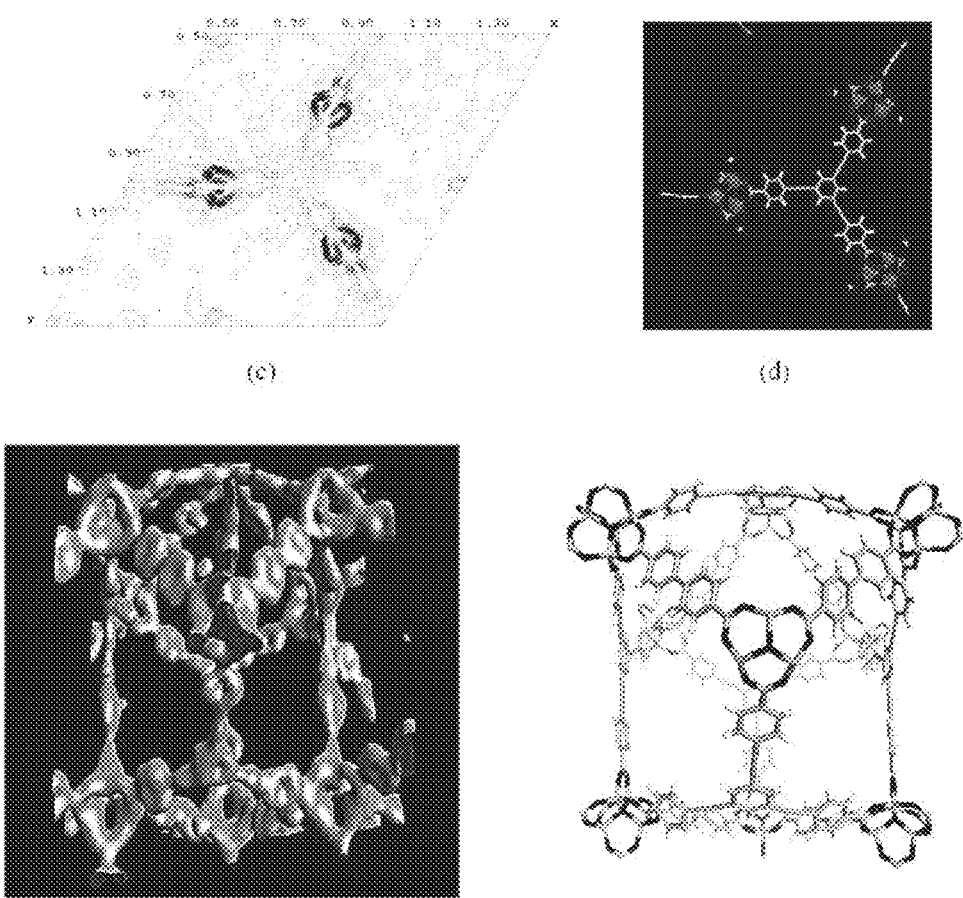
FIGURE 8C-F

OPEN METAL ORGANIC FRAMEWORKS WITH EXCEPTIONAL SURFACE AREA AND HIGH GAS STORAGE CAPACITY

CROSS REFERENCE TO RELATED APPLICATIONS

This application is a U.S. National Stage Filing under 35 U.S.C. §371 and claims priority to International Application No. PCT/US10/50170, filed Sep. 24, 2010, which application claims priority under 35 U.S.C. §119 from Provisional Application Ser. No. 61/246,065, filed Sep. 25, 2009, the disclosures of which are incorporated herein by reference.

STATEMENT REGARDING FEDERALLY SPONSORED RESEARCH

This invention was made with Government support under Grant No. HDTRA1-08-1-0023, awarded by the United States Department of Defense, Defense Threat Reduction Agency. The Government has certain rights in this invention.

TECHNICAL FIELD

The disclosure provides organic frameworks for gas separation and storage.

BACKGROUND

One of the challenges in the field of porous materials is to implement high storage capacity. Such materials are quite important because of the environmental concern in the earth. From the discovery of metal-organic frameworks (MOFs), researchers have sought and developed frameworks with reported high surface area materials whose apparent surface areas approach 6000 square meter per gram.

SUMMARY

The disclosure provides a metal-organic framework (MOF) comprising a plurality of metal clusters, each metal cluster comprising one or more metal ions; and a plurality of at least one first multidentate aromatic tritopic linking ligand that connects adjacent metal clusters, the plurality of multidentate linking ligands having a sufficient number of accessible sites for atomic or molecular adsorption such that the surface area of the metal-organic framework is greater than about 5500 $m^2/g$. In one embodiment, the metal-organic framework further comprises at least one second linking ligand different than the first linking ligand. In yet another embodiment, the metal cluster comprises 3 or more metal ions. In one embodiment, the plurality of multidentate linking ligands have a sufficient number of accessible sites for atomic or molecular adsorption that the surface area is greater than 6,000 $m^2/g$. In another embodiment, the plurality of multidentate linking ligands have a sufficient number of accessible sites for atomic or molecular adsorption that the surface area is greater than about 6,500 $m^2/g$. In one embodiment, the plurality of multidentate linking ligands have a sufficient number of accessible sites for atomic or molecular adsorption that the surface area is greater than about 10,000 $m^2/g$. In yet another embodiment, each ligand of the plurality of multidentate ligand includes 2 or more carboxylates. In one embodiment, the metal ion is selected from the group consisting of $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Cr^{3+}$, $Mo^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^{2+}$, $Ni^+$, $Pd^{2+}$, $Pd^+$, $Pt^{2+}$, $Pt^+$, $Cu^{2+}$, $Cu^+$, $Au^+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, $Cd^{2+}$, $Mn^{2+}$, $Tb^{3+}$, $Gd^{3+}$, $Ce^{3+}$, $La^{3+}$, $Cr^{4+}$ and combinations thereof. In yet another embodiment, the first linking ligand comprises the structure of formula I:

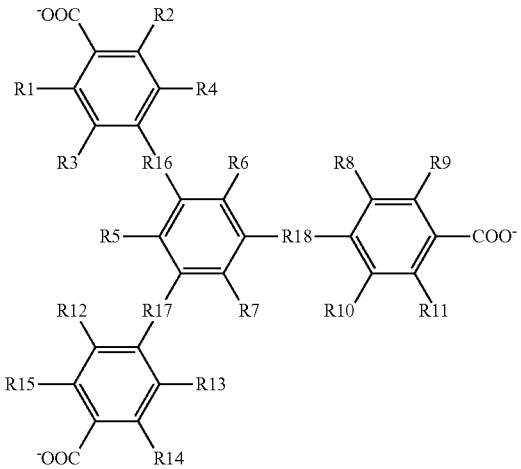

Formula I wherein R1-R15 are each individually selected from: alkyl, aryl, alkoxy, akenes, alkynes, phenyl, substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorous-containing groups, carboxylic acids, or esters, H, $NH_2$, CN, OH, =O, =S, Cl, I, F,

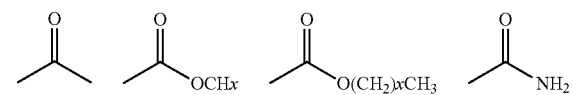

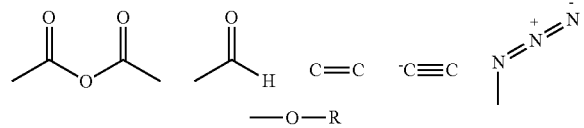

wherein X=1, 2, or 3; wherein R16, R17 and R18 may or may not be present, if present R16, R17 and R18 are selected from an alkyl or cycloalkyl group, comprising 1 to 20 carbon atoms, an aryl group comprising 1 to 5 phenyl rings, an alkyl or aryl amine comprising alkyl or cycloalkyl groups having from 1 to 20 carbon atoms or aryl groups comprising 1 to 5 phenyl rings, or —C≡C—. In certain embodiments, the R group is imine functionalized to promote chelating of a post-synthesis metal. In yet another embodiment, the first linking ligand comprises the structure of Formula II:

Formula II

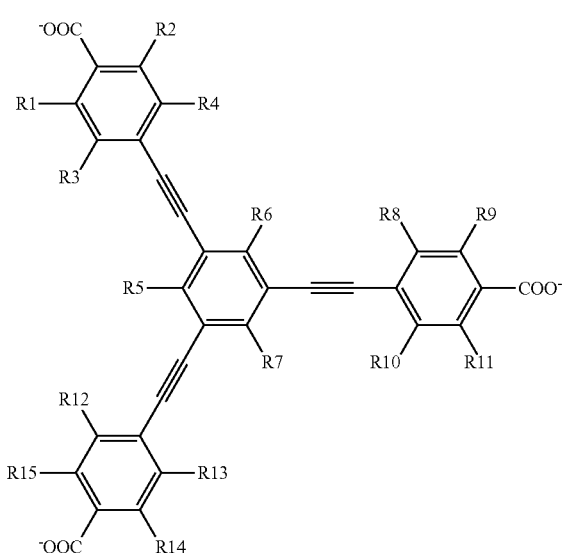

wherein R1-R15 are each individually selected from: alkyl, aryl, alkoxy, akenes, alkynes, phenyl, substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorous-containing groups, carboxylic acids, or esters, H, $NH_2$, CN, OH, =O, =S, Cl, I, F,

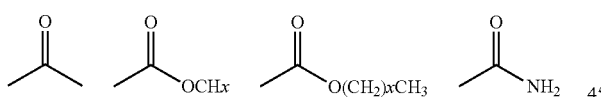

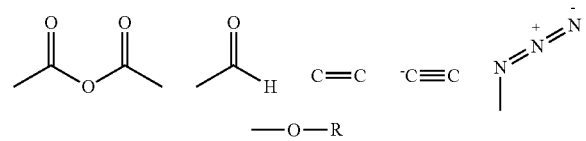

wherein X=1, 2, or 3. In one embodiment, the first linking ligand comprises the structure of Formula III:

Formula III

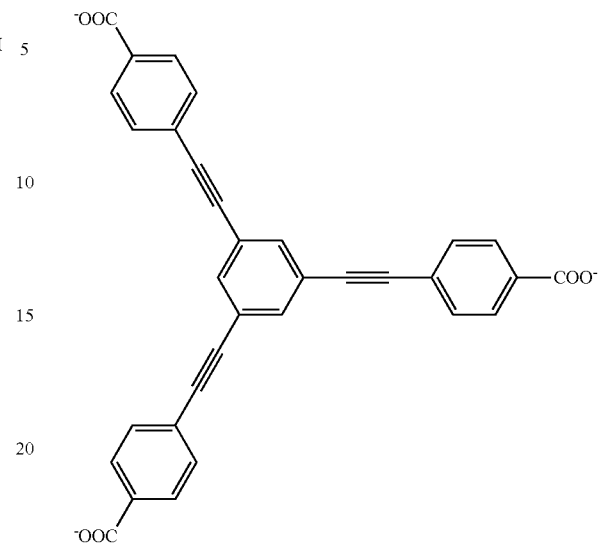

4,4',4''-(benzene-1,3,5-triyl-tris(ethyne-2,1-diyl)) tribenzoate (BTE)

In another embodiment, the first linking ligand comprises the structure of Formula IV:

Formula IV

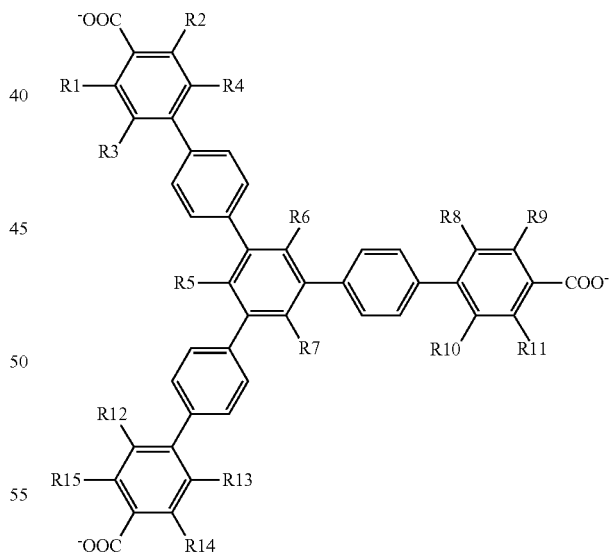

wherein R1-R15 are each individually selected from: alkyl, aryl, alkoxy, akenes, alkynes, phenyl, substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorous-containing groups, carboxylic acids, or esters, H, $NH_2$, CN, OH, =O, =S, Cl, I, F,

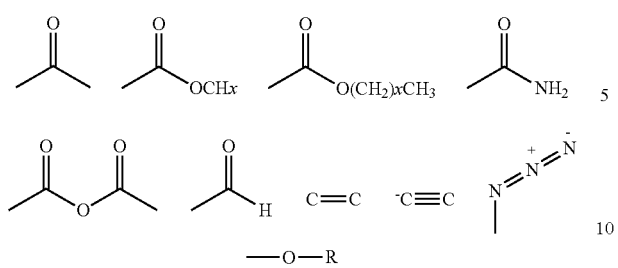
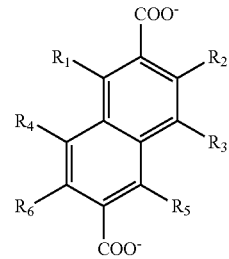

wherein X=1, 2, or 3. In yet another embodiment, the first linking ligand comprises the structure of Formula V:

Formula V

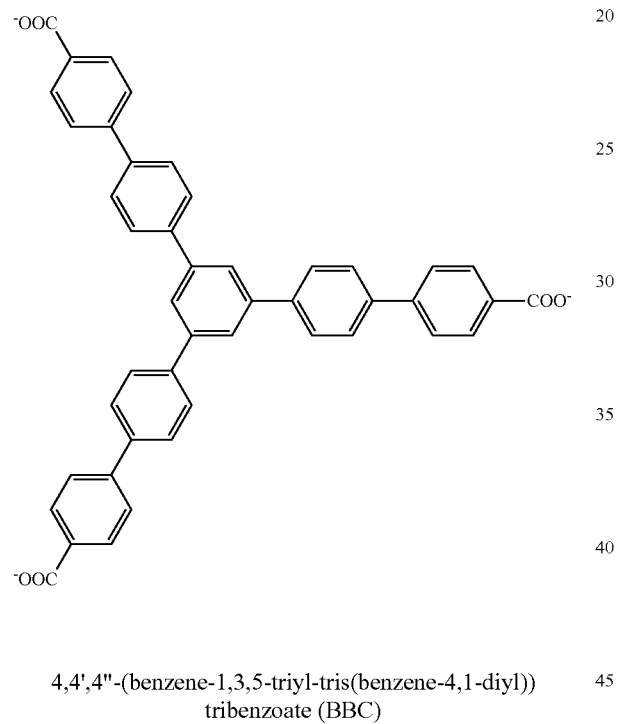

4,4',4''-(benzene-1,3,5-triyl-tris(benzene-4,1-diyl)) tribenzoate (BBC)

In other embodiments, comprising a second linking ligand, second linking ligand comprises a structure of Formula VI or VII:

Formula VI

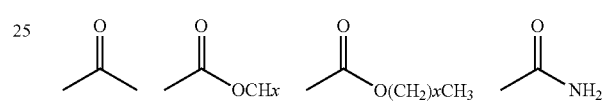

Formula VII wherein R1-R8 are each individually selected from: alkyl, aryl, alkoxy, akenes, alkynes, phenyl, substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorous-containing groups, carboxylic acids, or esters, H, NH$_2$, CN, OH, =O, =S, Cl, I, F,

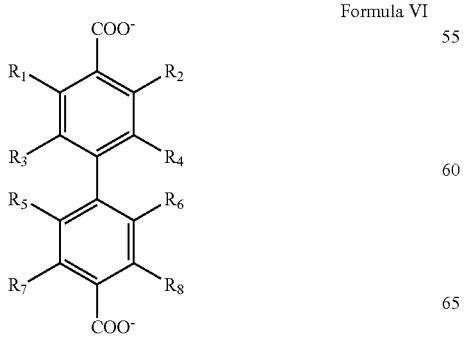

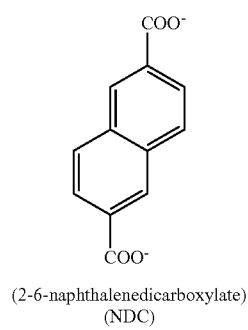

wherein X=1, 2, or 3. In further embodiments, the second linking ligand comprises the structure of Formula VIII and IX:

Formula VIII (2-6-naphthalenedicarboxylate) (NDC)

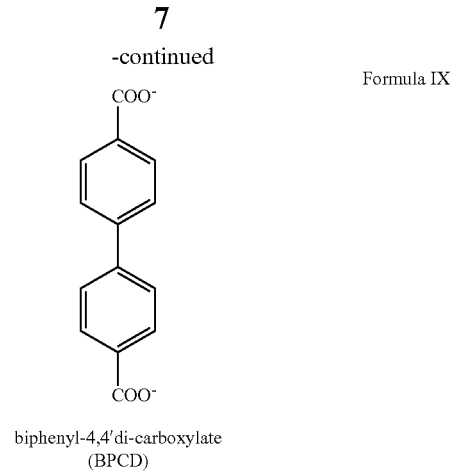

Formula IX biphenyl-4,4'di-carboxylate (BPCD)

In some embodiments, wherein the first linking ligand comprises the structure of Formula I lacking R16, R17 and R18 the second linking ligand comprises a structure of Formula VI, VII, VIII or IX.

The disclosure also provides a method of forming a metal-organic framework (MOF), the method comprising: combining a solution comprising a solvent and metal ions selected from the group consisting Group 1 through 16 metals including actinides, and lanthanides, and combinations thereof with at least a first multidentate linking ligand comprising the general formula of I-V such that the surface area of the metal-organic framework is greater than 5500 m²/g.

The disclosure also provides methods of gas storage and separation comprising contacting a MOF of the disclosure with a fluid wherein an analyte in the fluid interacts and is absorbed into the MOF.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A-H shows connectivity of pyr and qom (6,3)-coordinated nets. For pyr (A), pairs of pyr nets can naturally interpenetrate (B). In contrast, qom is not self-dual (C to E); the connectivity of the net of the dual tiling for qom (D) is very different from the original (C). Crystal structures of MOF-177 (F), MOF-180 (G), and MOF-200 (H) are found in qom net (C). The ball is placed in the structure for clarity and to indicate space in the cage. Zn, tetrahedral; O; and C atoms are depicted. Hydrogen atoms are omitted for clarity.

FIG. 2A-D shows crystal structures of MOF-205 (A) and MOF-210 (B). The balls are placed in the structure for clarity and to indicate space in the cage. Atom are the same as in FIG. 1. Tiling of (C) ith-d and (D) toz nets.

FIG. 3A-D shows gas uptake results. (A) Low-pressure $N_2$ isotherms of MOF-5, -177, -200, -205, and -210 at 77 K. Simulated isotherms of MOF-200 and -210 were overlaid. $P/P_0$, relative pressure. High-pressure $H_2$ isotherms were measured at 77 K (B), and (C) $CH_4$ and (D) $CO_2$ isotherms were measured at 298 K of the same MOFs.

FIG. 4A-B are selected electron density maps calculated by WinGX FOURIER MAP with $F_0$ coefficients. Sections at (A) z=0.25 are displayed by WinGX CONTOUR with a contouring level of 0.15 e$^-$/Å$^3$. Black contours are for positive, and light gray for negative contours. A model structure is also displayed with a unit cell content of z=0~0.25 in (B).

FIG. 8A-F are selected electron density maps calculated by WinGX FOURIER MAP with $F_0$ coefficients. Sections at (a) y=0.011, and (c) z=0.137 are displayed by WinGX CONTOUR with a contouring level of 0.40 e$^-$/Å$^3$. Black contours are for positive, and light gray for negative contours. Structural models at (b) y=0.~0.03 and (d) z=0.12~0.14 are also displayed for comparison with the electron density map. A three-dimensional electron density map in (e) and its corresponding structure in (f) show also BPDC linkers are participating in building MOF-210 framework; the packing range is 0.22~1.00 for x, −0.02~0.80 for y, and 0.05~0.22 for z. The electron density map was drawn by MCE2005.

DETAILED DESCRIPTION

Figure 5:
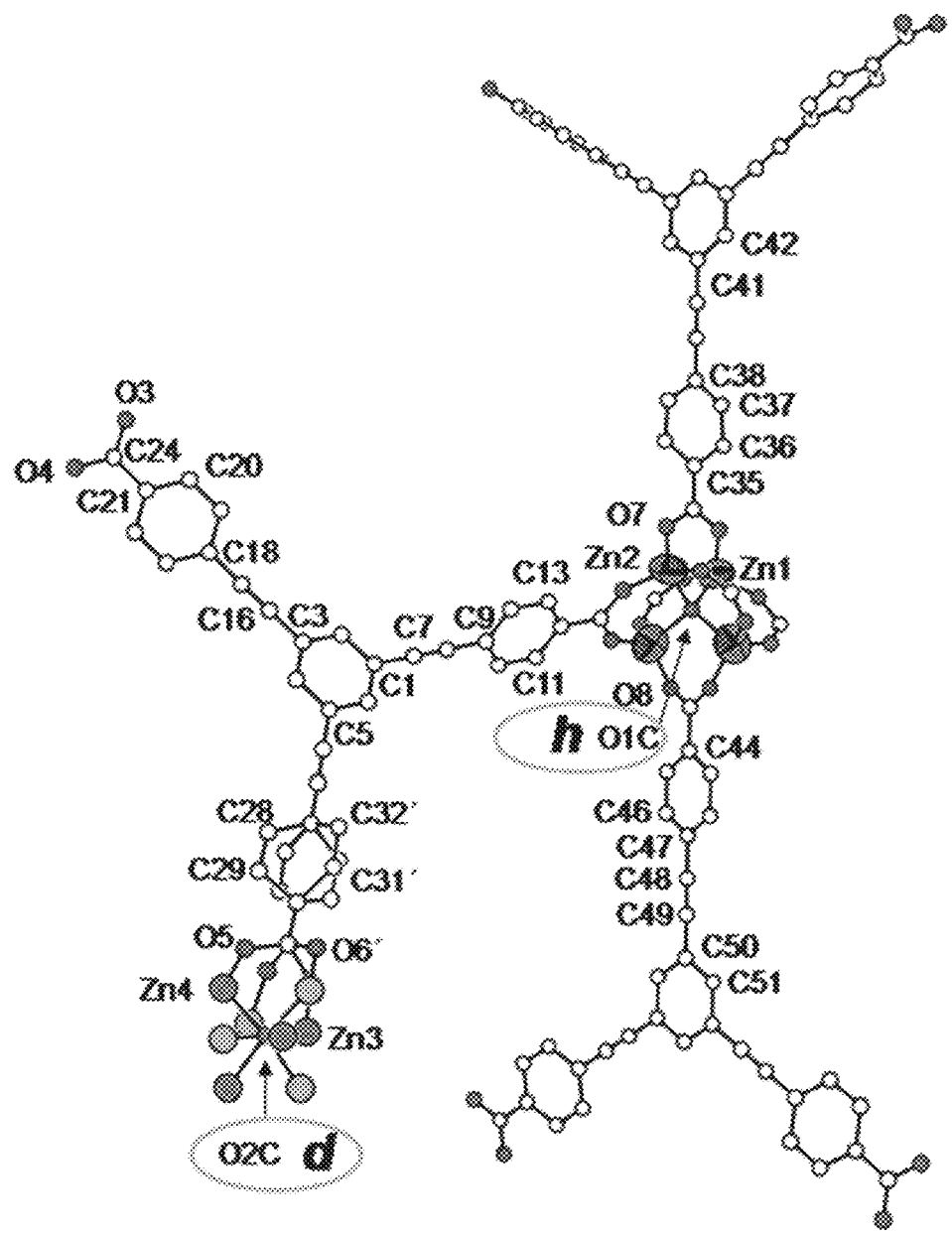
FIG. 5 shows a fragment structure of MOF-180 displayed by ORTEP. Selected atoms in the asymmetric unit are labeled. A benzene ring (C27~C32) is disordered over two sites at general positions while a $Zn_4O$ unit is disordered at a special position, d. According to these disorders, the carboxylate oxygen atoms, O5 and O6 are also disordered over two sites. Thermal ellipsoids for Zn atoms are displayed with 20% probability. Hydrogen atoms are not shown for simplicity.

As used herein and in the appended claims, the singular forms "a," "and," and "the" include plural referents unless the context clearly dictates otherwise. Thus, for example, reference to "a framework" includes a plurality of such frameworks and reference to "the metal" includes reference to one or more metals and equivalents thereof known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

Recently metal-organic frameworks (MOFs) have merged as an important class of porous materials for their well-characterized structures in terms of atomic connectivity and chemical composition. First example of the rigid framework is MOF-2 (Zn(BDC), BDC=1,4-benzenedicarboxylate) having square channels. The isotherm shape, typical Type I without hysteresis, demonstrates the existence of microporous structures even after removal of guest species. Within a decade from this discovery, researchers have been exploring high surface area MOFs, whose apparent surface areas exceed 5000 m² g⁻¹. The apparent surface area of MOFs can be estimated by use of the free volume ($V_{free}$) and density of MOFs ($d_{MOF}$). Since the pore volume of MOF per gram is described as $V_{free}$ [%]/100 $d_{MOF}$ [g cm⁻³], weight of N₂ adsorbed in the pore should be calculated, assuming that adsorbed N₂ behaves as a liquid in the micropore and its density ($d_{LN2}$) is 0.806 g cm⁻³. Assuming that a cross sectional area of N₂ molecule is 16.2 Å², Langmuir surface area for 1 mole of N₂ is theoretically 97524 m². By combining two relationships, one can obtain following simple equation.

$$S = \frac{V_{free}}{d_{MOF}} \times \frac{1}{100} \times \frac{d_{LN2}}{MW_{N2}} \times 97524 \approx 28 \times \frac{V_{free}}{d_{MOF}} \quad (1)$$

where $MW_{N2}$ is molecular weight of N₂. This equation implies that one can deliver highly porous MOFs whose apparent surface areas reach 10000 m² g⁻¹, if $V_{free}$ and $d_{MOF}$ are 90% and 0.25 g cm⁻³, respectively. Although it appears that the apparent surface area may not be equal to a real accessible surface based on simulation calculations, the pursuit of highly porous crystalline materials is still one of the biggest challenges in the field of material science.

The disclosure provides two strategies and resulting compositions that have allowed the realization of crystalline materials with high storage space; (i) isoreticular expansion of the framework and (ii) insertion of secondary organic link for the framework reinforcement. The disclosure demonstrates the methodology and provides, as examples, three MOFs whose porosity is maintained even after complete guest removal. The maximum nitrogen uptake capacities at 77 Kelvin in these exemplary frameworks, named MOF-200, 205 and 210, are 2340, 1410 and 2330 cubic centimeter per gram, respectively. These apparent surface areas of 10400, 6170, and 10400 square meter per gram can be derived from a cross sectional area of nitrogen (16.2 square angstrom per molecule), which have never been observed in crystalline materials yet.

The disclosure provides a composition comprising a metal linked to one or more other metals by a linking substructure. The metals are linked to the linking substructure by a linking cluster, typically be a condensation reaction. As depicted herein, most linking clusters are depicted as a carboxylate group at ends of the linking substructure. One of skill in the art will recognize that upon condensation with a metal, the linking cluster will form a bond between the linking substructure and the metal through, for example, an oxygen atom. Other linking clusters will be readily apparent and are described herein.

The linking substructure used in the methods and compositions of the disclosure comprise compounds that increase the distance between metal atoms while limiting fragility and maintaining stability. By increasing the distance between metals the pores size of a particular MOF is increased. In some embodiments, heterogeneous linking substructures are used.

As used herein, a "core" refers to a repeating unit or units found in a framework. Such a framework can comprise a homogenous repeating core or a heterogeneous repeating core structure. A core comprises a transition metal or cluster of transitions metals and a linking substructure. A plurality of cores linked together defines a framework.

The term "cluster" refers to identifiable associations of 2 or more atoms. Such associations are typically established by some type of bond—ionic, covalent, van der Waals, and the like.

A "linking cluster" refers to a one or more reactive species capable of condensation comprising an atom capable of forming a bond between a linking moiety substructure and a metal group or between a linking moiety and another linking moiety. Examples of such species are selected from the group consisting of a boron, oxygen, carbon, nitrogen, and phosphorous atom. In some embodiments, the linking cluster may comprise one or more different reactive species capable of forming a link with a bridging oxygen atom. For example, a linking cluster can comprise $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, $CH(SH)_2$, $C(SH)_3$, $CH(NH_2)_2$, $C(NH_2)_3$, $CH(OH)_2$, $C(OH)_3$, $CH(CN)_2$, and $C(CN)_3$, wherein R is an alkyl group having from 1 to 5 carbon atoms, or an aryl group comprising 1 to 2 phenyl rings and $CH(SH)_2$, $C(SH)_3$, $CH(NH_2)_2$, $C(NH_2)_3$, $CH(OH)_2$, $C(OH)_3$, $CH(CN)_2$, and $C(CN)_3$. Typically ligands for MOFs contain carboxylic acid functional groups.

A "linking moiety" refers to a mono-dentate or polydentate compound that bind a transition metal or a plurality of transition metals, respectively. Generally a linking moiety comprises a substructure of an alkyl or cycloalkyl group, comprising 1 to 20 carbon atoms, an aryl group comprising 1 to 5 phenyl rings, or an alkyl or aryl amine comprising alkyl or cycloalkyl groups having from 1 to 20 carbon atoms or aryl groups comprising 1 to 5 phenyl rings, and in which linking cluster(s) are covalently bound to the substructure. A cycloalkyl or aryl substructure may comprise 1 to 5 rings that comprise either of all carbon or a mixture of carbon with nitrogen, oxygen, sulfur, boron, phosphorus, silicon and/or aluminum atoms making up the ring. Typically the linking moiety will comprise a substructure having one or more carboxylic acid linking clusters covalently attached.

As used herein, a line in a chemical formula with an atom on one end and nothing on the other end means that the formula refers to a chemical fragment that is bonded to another entity on the end without an atom attached. Sometimes for emphasis, a wavy line will intersect the line.

In one embodiment, a linking moiety substructure for use in the compositions and methods of the disclosure comprises:

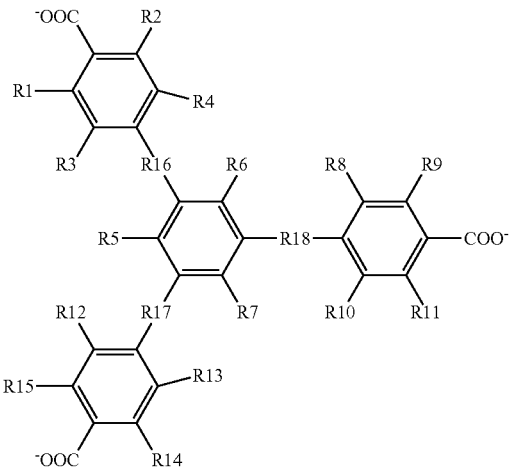

Formula I wherein R1-R15 are each individually selected from: alkyl, aryl, alkoxy, akenes, alkynes, phenyl, substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorous-containing groups, carboxylic acids, or esters, H, $NH_2$, CN, OH, =O, =S, Cl, I, F,

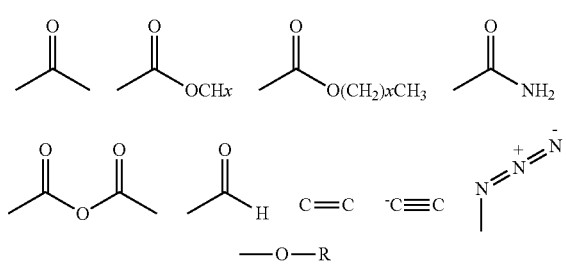

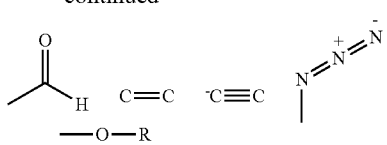

wherein X=1, 2, or 3.

In another embodiment, the linking moiety has the general structure of Formula III:

wherein X=1, 2, or 3; wherein R16, R17 and R18 may or may not be present, if present R16, R17 and R18 are selected from an alkyl or cycloalkyl group, comprising 1 to 20 carbon atoms, an aryl group comprising 1 to 5 phenyl rings, an alkyl or aryl amine comprising alkyl or cycloalkyl groups having from 1 to 20 carbon atoms or aryl groups comprising 1 to 5 phenyl rings, or —C≡C—. In certain embodiments, the R group is imine functionalized to promote chelating of a post-synthesis metal.

In one embodiment, the linking moiety has the general structure of Formula II:

Formula II

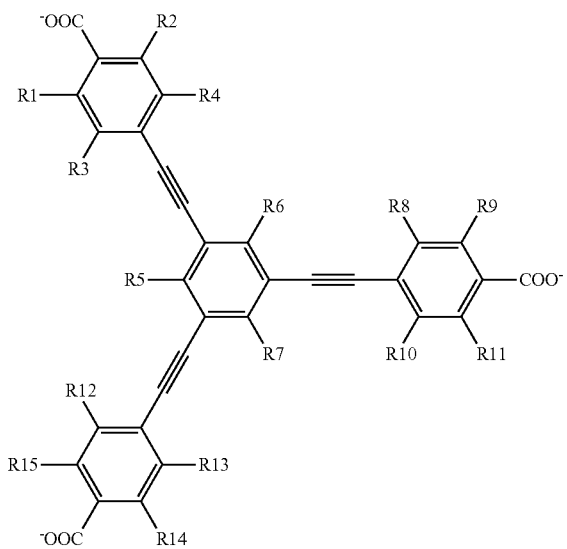

wherein R1-R15 are each individually selected from: alkyl, aryl, alkoxy, akenes, alkynes, phenyl, substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorous-containing groups, carboxylic acids, or esters, H, NH$_2$, CN, OH, =O, =S, Cl, I, F,

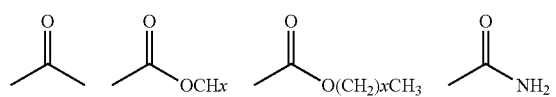

Formula III

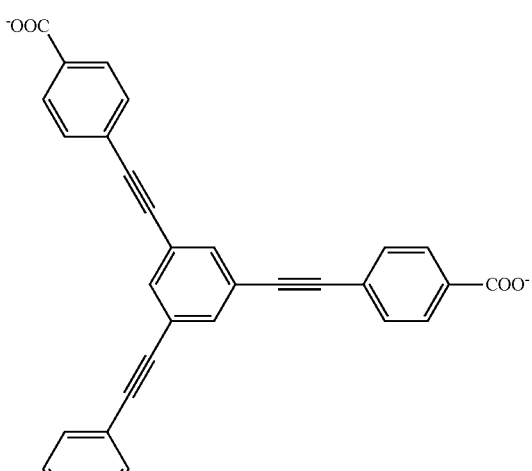

4,4′,4″-(benzene-1,3,5-triyl-tris(ethyne-2,1-diyl))tribenzoate (BTE)

In another embodiment, the linking moiety has the general structure of Formula IV:

Formula IV

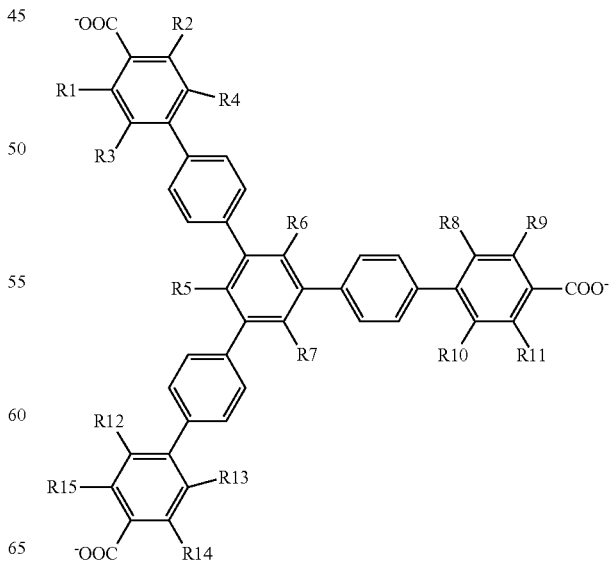

wherein R1-R15 are each individually selected from: alkyl, aryl, alkoxy, akenes, alkynes, phenyl, substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorous-containing groups, carboxylic acids, or esters, H, NH$_2$, CN, OH, =O, =S, Cl, I, F,

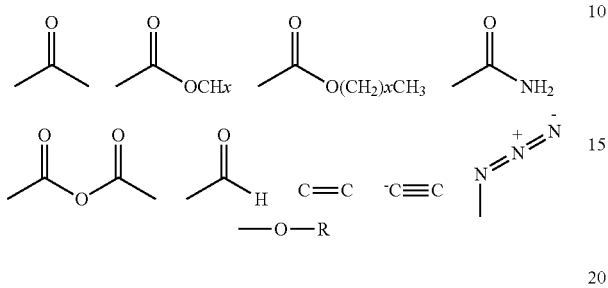

wherein X=1, 2, or 3.

In another embodiment, the linking moiety has the general structure of Formula V:

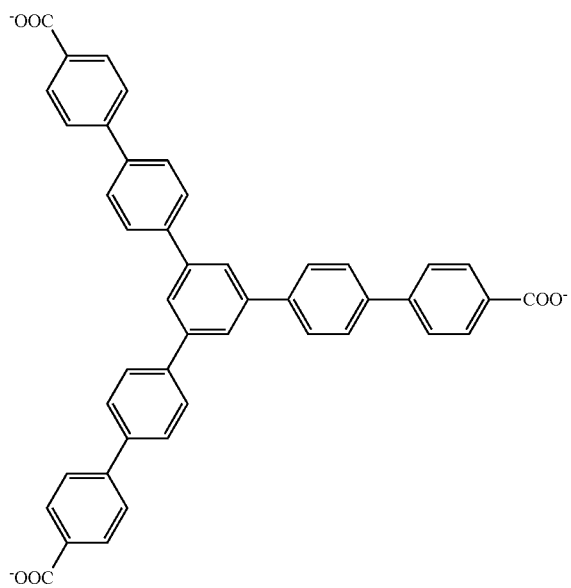

Formula V 4,4',4''-(benzene-1,3,5-triyl-tris(benzene-4,1-diyl))tribenzoate (BBC)

In each of the foregoing the carboxylic acid linking cluster can under condensation with a metal to for a framework. Metal ions that can be used in the synthesis of frameworks of the disclosure include Li$^+$, Na$^+$, Rb$^+$, Mg$^{2+}$, Ca$^{2+}$, Sr$^{2+}$, Ba$^{2+}$, Sc$^{3+}$, Ti$^{4+}$, Zr$^{4+}$, Ta$^{3+}$, Cr$^{3+}$, Mo$^{3+}$, W$^{3+}$, Mn$^{3+}$, Fe$^{3+}$, Fe$^{2+}$, Ru$^{3+}$, Ru$^{2+}$, Os$^{3+}$, Os$^{2+}$, Co$^{3+}$, Co$^{2+}$, Ni$^{2+}$, Ni$^+$, Pd$^{2+}$, Pd$^+$, Pt$^{2+}$, Pt$^+$, Cu$^{2+}$, Cu$^+$, Au$^+$, Zn$^{2+}$, Al$^{3+}$, Ga$^{3+}$, In$^{3+}$, Si$^{4+}$, Si$^{2+}$, Ge$^{4+}$, Ge$^{2+}$, Sn$^{4+}$, Sn$^{2+}$, Bi$^{5+}$, Bi$^{3+}$, Cd$^{2+}$, Mn$^{2+}$, Tb$^{3+}$, Gd$^{3+}$, Ce$^{3+}$, La$^{3+}$, Cr$^{4+}$ and combinations thereof, along with corresponding metal salt counteranions.

In certain embodiments, the framework comprises heterogeneous linking moieties. In such instances, one linking moiety is selected from Formulas I-V above and a second moiety is selected from a structure having the general formula of VI or VII:

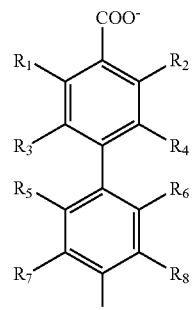

Formula VI

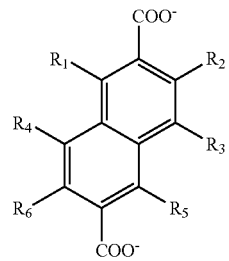

Formula VII wherein R1-R8 are each individually selected from: alkyl, aryl, alkoxy, akenes, alkynes, phenyl, substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorous-containing groups, carboxylic acids, or esters, H, NH$_2$, CN, OH, =O, =S, Cl, I, F,

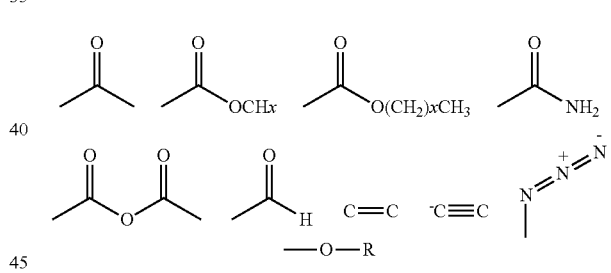

wherein X=1, 2, or 3.

In one embodiment, the heterogenous linking moieties are selected from a first linking moiety of Formula I-V and a second linking moiety selected from Formula VIII and IX:

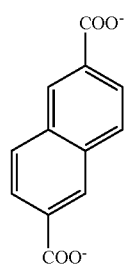

Formula VIII (2-6-naphthalenedicarboxylate) (NDC)

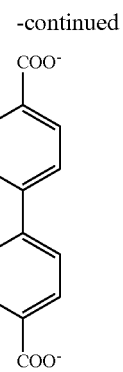

biphenyl-4,4'di-carboxylate
(BPCD)

Formula IX

In one embodiment, a linking moiety comprising formula I lacking R16, R17 and R18 is used as a linking moiety in combination with a second linking moiety having a structure of Formula VI, VII, VIII or IX.

As mentioned above, the linking moieties can be reacted with a metal, metal salt or ion to form a metal organic framework having a porosity and surface area that exceeds previous MOF porosity and surface area (e.g., MOF-177).

The preparation of the frameworks of the disclosure can be carried out in either an aqueous or non-aqueous system. The solvent may be polar or non-polar as the case may be. The solvent can comprise the templating agent or the optional ligand containing a monodentate functional group. Examples of non-aqueous solvents include n-alkanes, such as pentane, hexane, benzene, toluene, xylene, chlorobenzene, nitrobenzene, cyanobenzene, aniline, naphthalene, naphthas, n-alcohols such as methanol, ethanol, n-propanol, isopropanol, acetone, 1,3-dichloroethane, methylene chloride, chloroform, carbon tetrachloride, tetrahydrofuran, dimethylformamide, dimethylsulfoxide, N-methylpyrollidone, dimethylacetamide, diethylformamide, thiophene, pyridine, ethanolamine, triethylamine, ethlenediamine, and the like. Those skilled in the art will be readily able to determine an appropriate solvent based on the starting reactants and the choice of solvent is not believed to be crucial in obtaining the materials of the disclosure.

Templating agents can be used in the methods of the disclosure. Templating agents employed in the disclosure are added to the reaction mixture for the purpose of occupying the pores in the resulting crystalline base frameworks. In some variations of the disclosure, space-filling agents, adsorbed chemical species and guest species increase the surface area of the metal-organic framework. Suitable space-filling agents include, for example, a component selected from the group consisting of: (i) alkyl amines and their corresponding alkyl ammonium salts, containing linear, branched, or cyclic aliphatic groups, having from 1 to 20 carbon atoms; (ii) aryl amines and their corresponding aryl ammonium salts having from 1 to 5 phenyl rings; (iii) alkyl phosphonium salts, containing linear, branched, or cyclic aliphatic groups, having from 1 to 20 carbon atoms; (iv) aryl phosphonium salts, having from 1 to 5 phenyl rings; (v) alkyl organic acids and their corresponding salts, containing linear, branched, or cyclic aliphatic groups, having from 1 to 20 carbon atoms; (vi) aryl organic acids and their corresponding salts, having from 1 to 5 phenyl rings; (vii) aliphatic alcohols, containing linear, branched, or cyclic aliphatic groups, having from 1 to 20 carbon atoms; or (viii) aryl alcohols having from 1 to 5 phenyl rings.

Crystallization can be carried out by leaving the solution at room temperature or in isothermal oven for up to 300° C.; adding a diluted base to the solution to initiate the crystallization; diffusing a diluted base into the solution to initiate the crystallization; and/or transferring the solution to a closed vessel and heating to a predetermined temperature.

For example, in certain embodiments, a $Zn_4O(CO_2)_6$-containing compound such as $Zn_4O(O_2CR)_6$, wherein R can be alkyl, aryl, or —$N(R_1)(R_2)$, wherein $R_1$ and $R_2$ can be —H or any alkyl group can be reacted with a linking moiety of Formula I-V to form a metal organic framework comprising a surface area of about 10,400 m²/g and a pore volume of about 3.59 cm³/g and an RCSR code of qom and a crystal density of between about 0.20 and 0.39 g/cm³. As described more fully below, these MOFs can be utilized for gas storage and separation or they may be further functionalize (using post synthesis reactions) to obtain yet further structures useful in gas separation, storage, sensing and catalysis.

In another embodiment, a $Zn_4O(CO_2)_6$-containing compound such as $Zn_4O(O_2CR)_6$, wherein R can be alkyl, aryl, or —$N(R_1)(R_2)$, wherein $R_1$ and $R_2$ can be —H or any alkyl group can be reacted with heterogenous linking moieties wherein a first linking moiety comprises a Formula I-IV or V and a second linking moiety comprises Formula VI-VIII or IX to form a metal organic framework comprising a surface area of between about 6,100 and about 10,400 m²/g, a pore volume of about 2.1 to 3.6 cm³/g, an RCSR code of ith-d or toz and a crystal density of between about 0.20 and 0.39 g/cm³. As described more fully below, these MOFs can be utilized for gas storage and separation or they may be further functionalize (using post synthesis reactions) to obtain yet further structures useful in gas separation, storage, sensing and catalysis.

Scheme 1, below, provides examples of certain MOFs generated by the methods of the disclosure utilizing a metal and a linking moiety selected from formula I-IX or combinations thereof.

For example, the MOFs generated by Scheme I above having the characteristics set forth in Table I:

TABLE 1

Porosity data of highly porous MOFs.

| Compound | RCSR code | Linker | Void volume (%) | Crystal density (g cm⁻³) | $A_{BET}$ (m² g⁻¹) | $A_{Lang}$ (m² g⁻¹) | $A_{geo}$* (m² g⁻¹) | $V_p$ (cm³ g⁻¹) |
|---|---|---|---|---|---|---|---|---|
| MOF-5 | pcu | BDC | 79 | 0.59 | 3800 | 4400 | 3390 | 1.55 |
| MOF-177 | qom | BTB | 83 | 0.43 | 4500 | 5340 | 4740 | 1.89 |
| MOF-180 | qom | BTE | 89 | 0.25 | ND | ND | 6080 | ND |

TABLE 1-continued

Porosity data of highly porous MOFs.

| Compound | RCSR code | Linker | Void volume (%) | Crystal density (g cm$^{-3}$) | $A_{BET}$ (m$^2$g$^{-1}$) | $A_{Lang}$ (m$^2$g$^{-1}$) | $A_{geo}$* (m$^2$g$^{-1}$) | $V_p$ (cm$^3$g$^{-1}$) |
|---|---|---|---|---|---|---|---|---|
| MOF-200 | qom | BBC | 90 | 0.22 | 4530 | 10400 | 6400 | 3.59 |
| MOF-205 | ith-d | BTB, NDC | 85 | 0.38 | 4460 | 6170 | 4680 | 2.16 |
| MOF-210 | toz | BTE, BPDC | 89 | 0.25 | 6240 | 10400 | 5850 | 3.60 |
| UMCM-2 | umt | BTB, T2DC | 83 | 0.40 | 5200 | 6060 | 4360 | 2.32 |
| MIL-101c | mtn-e | BDC | 83 | 0.44 | 4230 | 5900 | 2880 | 2.15 |

$A_{BET}$, $A_{Lang}$, and $A_{geo}$ are the BET, Langmuir, and geometric surface areas, respectively.
$V_p$ is the measured pore volume.
ND, no data;
H$_2$T2DC, thieno[3,2-b]thiophene-2,5-dicarboxylic acid.

As described herein and above, the linking moieties may be tailored to comprise a reactive side group for post framework synthesis and reaction. All the aforementioned organic links that possess appropriate reactive functionalities can be chemically transformed by a suitable reactant post framework synthesis to further functionalize the pores. By modifying the organic links within the framework post-synthetically, access to functional groups that were previously inaccessible or accessible only through great difficulty and/or cost is possible and facile. Post framework reactants include all known organic transformations and their respective reactants; rings of 1-20 carbons with functional groups including atoms such as N, S, O and all metals that may chelate to and added functional group or a combination of previously existing an newly added functional groups. All reactions that result in tethering an organometallic complex to the framework for use, for example, as a heterogenous catalysts are contemplated.

Examples of post framework reactants include, but are not limited to, heterocyclic compounds. In one embodiment, the post framework reactant can be a saturated or unsaturated heterocycle. The term "heterocycle" used alone or as a suffix or prefix, refers to a ring-containing structure or molecule having one or more multivalent heteroatoms, independently selected from N, O and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings share two atoms therebetween. Heterocycle may have aromatic character or may not have aromatic character. The terms "heterocyclic group", "heterocyclic moiety", "heterocyclic", or "heterocyclo" used alone or as a suffix or prefix, refers to a radical derived from a heterocycle by removing one or more hydrogens therefrom. The term "heterocyclyl" used alone or as a suffix or prefix, refers a monovalent radical derived from a heterocycle by removing one hydrogen therefrom. The term "heteroaryl" used alone or as a suffix or prefix, refers to a heterocyclyl having aromatic character. Heterocycle includes, for example, monocyclic heterocycles such as: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide. For example, heterocycles useful in the methods of the disclosure include:

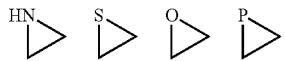

In addition, heterocycle includes aromatic heterocycles (heteroaryl groups), for example, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

Additionally, heterocycle encompass polycyclic heterocycles, for example, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine.

In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

The ultrahigh surface areas exhibited by the MOFs described herein (e.g., MOF-180, MOF-200, -205 and -210 are near the ultimate limit for solid materials. To appreciate this, it is useful to note that all these compounds have a volume specific surface area in the range of 1000 to 2000 m$^2$/cm$^3$=1×10$^9$ to 2×10$^9$ m$^{-1}$, and for a cube of edge d the external surface area/volume is 6d$^2$/d$^3$=6/d. Thus, for a monodisperse powder of cubic nanoparticles to have external surface that is equal to that of these MOFs the cube edge would have to be only 3 to 6 nm, which is a size far too small to practically realize in stable dry powders and therefore impossible to access the full surface area of such particles.

Natural gas is an important fuel gas and it is used extensively as a basic raw material in the petrochemical and other chemical process industries. The composition of natural gas varies widely from field to field. Many natural gas reservoirs contain relatively low percentages of hydrocarbons (less than 40%, for example) and high percentages of acid gases, principally carbon dioxide, but also hydrogen sulfide, carbonyl sulfide, carbon disulfide and various mercaptans. Removal of acid gases from natural gas produced in remote locations is desirable to provide conditioned or sweet, dry natural gas either for delivery to a pipeline, natural gas liquids recovery, helium recovery, conversion to liquefied natural gas (LNG), or for subsequent nitrogen rejection. $CO_2$ is corrosive in the presence of water, and it can form dry ice, hydrates and can cause freeze-up problems in pipelines and in cryogenic equipment often used in processing natural gas. Also, by not contributing to the heating value, $CO_2$ merely adds to the cost of gas transmission.

An important aspect of any natural gas treating process is economics. Natural gas is typically treated in high volumes, making even slight differences in capital and operating costs of the treating unit significant factors in the selection of process technology. Some natural gas resources are now uneconomical to produce because of processing costs. There is a continuing need for improved natural gas treating processes that have high reliability and represent simplicity of operation.

In addition, removal of carbon dioxide from the flue exhaust of power plants, currently a major source of anthropogenic carbon dioxide, is commonly accomplished by chilling and pressurizing the exhaust or by passing the fumes through a fluidized bed of aqueous amine solution, both of which are costly and inefficient. Other methods based on chemisorption of carbon dioxide on oxide surfaces or adsorption within porous silicates, carbon, and membranes have been pursued as means for carbon dioxide uptake. However, in order for an effective adsorption medium to have long term viability in carbon dioxide removal it should combine two features: (i) a periodic structure for which carbon dioxide uptake and release is fully reversible, and (ii) a flexibility with which chemical functionalization and molecular level fine-tuning can be achieved for optimized uptake capacities.

A number of processes for the recovery or removal of carbon dioxide from gas steams have been proposed and practiced on a commercial scale. The processes vary widely, but generally involve some form of solvent absorption, adsorption on a porous adsorbent, distillation, or diffusion through a semipermeable membrane.

Accordingly, the MOFs of the disclosure can be used for gas separation, storage, chemical separation and storage, catalysis and as sensors. The disclosure accordingly provides devices for the sorptive uptake of a chemical species. The device includes a sorbent comprising a framework provided herein or obtained by the methods of the disclosure. The uptake can be reversible or non-reversible. In some embodiments, the sorbent is included in discrete sorptive particles. The sorptive particles may be embedded into or fixed to a solid or liquid- and/or gas-permeable three-dimensional support. The MOFs of the disclosure comprise exception porosity for the reversible uptake or storage of liquids or gases and wherein the sorptive particles can reversibly adsorb or absorb the liquid or gas.

In some embodiments, a device provided herein comprises a storage unit for the storage of chemical species such as ammonia, carbon dioxide, carbon monoxide, hydrogen, amines, methane, oxygen, argon, nitrogen, argon, organic dyes, polycyclic organic molecules, and combinations thereof.

Also provided are methods for the sorptive uptake of a chemical species. The method includes contacting the chemical species with a sorbent that comprises a framework provided herein. The uptake of the chemical species may include storage of the chemical species. In some embodiments, the chemical species is stored under conditions suitable for use as an energy source.

Also provided are methods for the sorptive uptake of a chemical species which includes contacting the chemical species with a device provided described herein.

The following examples are intended to illustrate but not limit the disclosure. While they are typical of those that might be used, other procedures known to those skilled in the art may alternatively be used.

EXAMPLES

In the pursuit of MOFs with ultrahigh porosity, the octahedral $Zn_4O(CO_2)_6$ has been used as a building unit in producing structures exhibiting exceptional porosity (Scheme 1). Joining such units by 4,4',4"-benzene-1,3,5-triyl-tribenzoate (BTB) and/or 1,4-benzenedicarboxylate (BDC) linkers produces MOF-5, UMCM-2, and MOF-177, which heretofore showed the highest BET surface area and pore volume among MOFs (Table 1).

The disclosure expanded the links and use various combination of links to develop porosity that extendd the porosity of known MOFs.

The disclosure expanded the porosity of the MOFs using links comprising 4,4',4"-[benzene-1,3,5-triyl-tris(ethyne-2,1-diyl)]tribenzoate (BTE) and 4,4',4"-[benzene-1,3,5-triyl-tris(benzene-4,1-diyl)]tribenzoate (BBC) to give MOF-180 and MOF-200, respectively, and used mixed 4,4',4"-benzene-1,3,5-triyl-tribenzoate (BTB)/2,6-naphthalenedicarboxylate (NDC) and BTE/biphenyl-4,4'-dicarboxylate (BPDC) links to obtain MOF-205 and 210 (Scheme 1 and Table 1).

Derivative of aromatic tritopic linkers were used to extend MOF-177. The derivative comprises extended "arms" from the central aromatic ring extending the pores size (FIG. 1). The resulting framework in which alternating octahedral $Zn_4O(CO_2)_6$ and triangular BTE and BBC units produce one of the most porous structures yet reported.

An isoreticular non-interpenetrating expansion of MOF-177was targeted by using BTE or BBC to make the highly porous materials MOF-180 and -200 (FIG. 1, G and H). The unit cell volumes of MOF-180 and -200 are respectively 1.9 and 2.6 times greater than that of MOF-177, with void volumes of 89 and 90% of the crystal volume (Table 1). The cage sizes for MOF-180 and -200 are 15 by 23 and 18 by 28 Å, respectively, which is on the border of micropores and mesopores.

The bulk density for MOF-200 is 0.22 g $cm^{-3}$, implying that the qom net is advantageous to reduce the dead space and increase the gas storage capacity per unit volume in a closed tank. This density is the lowest for MOF structures, and of any other crystals at room temperature except for those of the least dense covalent organic frameworks.

On the basis of the effective use of the qom net for the successful synthesis of the non-interpenetrating MOF-180 and MOF-200, the development of other MOFs of nets without self-dual tilings were attempted by mixing organic links of mixed connectivity. Both tritopic $H_3BTB$ and ditopic $H_2NDC$ were used in a reaction with Zn ions to produce $Zn_4O(CO_2)_6$ units and make MOF-205 (FIG. 2A).

The MOF-205 structure belongs to a cubic space group Pm 3n and consists of one type of $Zn_4O(CO_2)_6$ octahedral unit whose vertices are connected to four BTB and two NDC links. The topology of MOF-205 (ith-d) is of considerable intrinsic interest; all the rings of the underlying net are 5-rings, and it forms a face transitive tiling of dodecahedra

[5¹²] and tetrahedral [5⁴] in the ratio 1:3 (FIG. 2C). The dual structure (ith) is an edge-transitive net with tetrahedral and icosahedral vertices and very different from the original net.

Attempts at isoreticular expansion of MOF-205 by use of the linkers BTE and BPDC produced a different but related material (termed MOF-210) (FIG. 2B). MOF-210 was prepared from a solvothermal reaction of $H_3BTE$, $H_2BPDC$, and zinc(II) nitrate hexahydrate. Rather than the 12-face tile of ith-d, the new topology has 30-face tiles, and the full tiling consists of $[4^6.5^{24}]$, $[4^3.5^{6}]$, and $[5^4]$ in the ratio 1:2:3 (FIG. 2D). The difference in the link length ratio (for example, 0.76 for MOF-210 and 0.79 for UMCM-2) may be important. The dimension of the largest cage in MOF-210 is 26.9 by 48.3 Å, which comprises 18 $Zn_4O$ units with 14 BTE and 6 BPDC links. The estimated bulk density (void space) is 0.25 g cm$^{-3}$ (89%), which is almost the same as that for MOF-180.

Considering the bulk density and void space calculated from the crystal structure analyses, MOF-200 and -210 are promising candidates to realize ultrahigh surface area. Before gas adsorption measurements, grand canonical Monte Carlo (GCMC) simulations were performed to calculate nitrogen adsorption isotherms. Predicted isotherms (FIG. 3A) show unusual steps attributed to the micropore filling at $P/P_0=0.12$ and 0.26 (for MOF-200 and -210, respectively), and total nitrogen uptakes in MOF-200 and -210 reaching 2650 and 2300 cm$^3$ g$^{-1}$, respectively. The BET and Langmuir surface areas determined from these calculated isotherms are respectively 6260 and 12,040 for MOF-200 and 6580 and 10,450 m$^2$ g$^{-1}$ for MOF-210; these are much higher than values reported previously for other porous crystals.

To assess the architectural stability and porosity of these low-density MOFs, and to confirm the calculations, nitrogen adsorption isotherms were measured on the guest free samples of MOF-200, -205, and -210. Preliminary trials revealed that the solvent exchange followed by pore evacuation under vacuum was not effective to activate MOF-200 and -210 without losing the porosity. Thus, these crystals were fully exchanged with liquid $CO_2$, they were kept under supercritical $CO_2$ atmosphere, and then their pores were bled of $CO_2$ in order to yield activated samples. Successful guest removal was confirmed by powder x-ray diffraction measurements and elemental analyses. As shown in FIG. 3A, all MOF samples show distinctive steps ($P/P_0=0.14$, 0.09, and 0.27 for MOF-200, -205, and -210, respectively), and the profiles for MOF-200 and -210 are nearly the same as the predicted isotherms. The maximum nitrogen uptake capacities at 77 K in MOF-200, -205, and -210 are 2340, 1410, and 2330 cm$^3$ g$^{-1}$, respectively.

These uptake values in MOF-200 and -210 are well beyond those observed for other crystalline porous solids. Further, the measured values are near the values predicted on the basis of the structure, indicating that these materials are well activated. Because of the successful sample activation, extremely high BET (and Langmuir) surface areas were obtained: 4530 (10,400), 4460 (6,170), and 6240 (10,400) m$^2$ g$^{-1}$ for MOF-200, -205, and -210, respectively. The BET surface area of MOF-210 is the highest reported for crystalline materials. It has recently been shown that the BET method applied to nitrogen adsorption isotherms provides physically meaningful values for the surface areas of MOFs.

Given the exceptional properties of such materials, it is expected that MOFs with ultrahigh surface area would exhibit exceptional gas storage capacity. Accordingly, this series of MOFs was subjected to high-pressure hydrogen (77 K) and methane (298 K) adsorption so as to examine their potential utility in the storage of gaseous fuels (FIG. 3, B and C, and table 13). In hydrogen isotherms, these MOFs reach saturation uptakes, and the saturation pressure increases with an increase in the cavity size. The surface excess hydrogen uptake in MOF-210 (86 mg g$^{-1}$) is higher than those in MOF-5, MOF-177, UMCM-2, and NOTT-112). The total uptake that a material can store is more relevant to the practicability of using $H_2$ as a fuel, but it cannot be measured experimentally. Therefore, this value was estimated using the pore volume and the density of hydrogen at 77 K. The calculated gravimetric hydrogen density in MOF-210 (176 mg g$^{-1}$) exceeds that of typical alternative fuels (methanol and ethanol) and hydrocarbons (pentane and hexane). MOF-200 and -205 also show large total hydrogen uptake (163 and 123 mg g$^{-1}$, respectively); again, these values are higher than MOF-177.

Methane uptake was measured at 298 K and up to 80 bar (FIG. 3C); under the present experimental conditions, all isotherms were not saturated. Although the excess methane uptake in MOF-200, -205, and -210 (234, 258, and 264 mg g$^{-1}$ at 80 bar, respectively) were smaller than that in PCN-14 (253 mg g–1 at 290 K and 35 bar, respectively), the calculated total uptakes (446, 394, and 476 mg g$^{-1}$ for MOF-200, -205, and -210, respectively) were more than 50% greater than those of PCN-14. Moreover, the corresponding volumetric methane densities in the present MOFs are respectively 2, 3, and 2.5 times greater than volumetric bulk density (grams per liter) of methane at the same temperature and pressure (table 13). Because the isotherms are nearly linear up to 80 bar, these materials can deliver most of the sorbed methane in the pressure range between 10 to 200 bar.

Large storage volumes should also be desirable for short-term $CO_2$ storage. High-pressure $CO_2$ isotherms for all three MOFs were collected and are presented in FIG. 3D. These MOFs show sigmoidal isotherms, and the pressure for the steep rise reflects the pore size of the MOFs. An isotherm for MOF-205 is saturated at a pressure of 37 bar, whereas the saturation pressure for MOF-200 and -210 are ~50 bar. In contrast to hydrogen and methane uptakes, the amounts of excess $CO_2$ uptake are directly related to the total pore volume. The $CO_2$ uptake value of 2400 mg g$^{-1}$ in both MOF-200 and -210 exceeds those of any other porous material, such as MOF-177 and MIL-101c(Cr) (1470 and 1760 mg g$^{-1}$, respectively).

Chemicals used in this work: 2,6-Naphthalendicarboxylic acid ($H_2NDC$), biphenyl-4,4'-dicarboxylic acid ($H_2BPDC$), zinc(II) nitrate hexahydrate ($Zn(NO_3)_2.6H_2O$), and anhydrous acetone were purchased from Sigma-Aldrich Co. and N,N-dimethylformamide (DMF) and 1-methyl-2-pyrrolidinone (NMP) were purchased from Fisher Scientific International Inc. Zinc(II) nitrate tetrahydrate ($Zn(NO_3)_2.4H_2O$) was purchased from EM Science. Pyridine was purchased from Daejung Chemicals & Metals Co., Ltd. All starting materials except for N,N-diethylformamide (DEF, BASF) were used without further purifications. DEF was treated by addition of charcoal carbon (ca. 0.5 g, Acros, CAS No.: 7440-44-0) into 1 L and stirred 12 h at room temperature. The black suspension solution was filtered through a silica-gel column (ca. 350 g, Silica gel 60, 230-400 mesh, EMD Chemicals) to remove carbon powder. 1,3,5-Tris(4'-carboxyphenyl)benzene ($H_3BTB$) was prepared according to published procedures.

Syntheses of Organic Linkers: A. 4,4',4"-(Benzene-1,3,5-triyltris(ethyne-2,1-diyl))tribenzoic acid ($H_3BTE$) Trimethyl 4,4',4"-(benzene-1,3,5-triyltris(ethyne-2,1-diyl))tribenzoate. A mixture of methyl 4-iodobenzoate (2.29 g, 8.75 mmol), $Pd(PPh_3)_2Cl_2$ (154 mg, 0.22 mmol) and CuI (209 mg, 1.10 mmol) in $NEt_3$ (30 mL) was added to 1,3,5-triethynylbenzene (365 mg, 2.43 mmol) in $NEt_3$ (10 mL). The mixture was stirred for 20 h at room temperature under argon atmosphere.

The solution was evaporated and the residue was dissolved in $CH_2Cl_2$. The organic layer was washed by brine, dried over $MgSO_4$, filtered and concentrated. Purification of the crude product by flash column chromatography on silica gel ($CH_2Cl_2$) provided trimethyl 4,4',4"-(benzene-1,3,5-triyltris (ethyne-2,1-diyl))tribenzoate as a pale yellow powder (788 mg, 59%): mp 177° C.; $^1$H-NMR ($CDCl_3$, 400 MHz) δ 8.05 (d, 6H, J=8.4 Hz), 7.70 (s, 3H), 7.60 (d, 6H, J=8.4 Hz), 3.94 (s, 9H); $^{13}$C-NMR ($CDCl_3$, 100 MHz) δ 166.5, 134.6, 131.6, 130.0 129.6, 127.3, 123.8, 90.3, 90.0, 52.3; FT-IR (KBr, 4000-400 cm$^{-1}$) 3428 (br), 2951 (w), 2372 (w), 1724 (s), 1604 (S), 1435 (m), 1403 (w), 1274 (s), 1175 (m), 1105 (s), 1017 (w), 857 (w), 768 (s).

4,4',4"-(Benzene-1,3,5-triyltris(ethyne-2,1-diyl))tribenzoic acid. A mixture of trimethyl 4,4',4"-(benzene-1,3,5-triyl-tris(ethyne-2,1-diyl))tribenzoate (773 mg, 1.40 mmol), $LiOH.H_2O$ (881 mg, 21.0 mmol), tetrahydrofuran (THF, 25 mL) and water (5 mL) was stirred for 16 h at room temperature. The reaction mixture was concentrated. The residue was acidified with cold 3 M HCl (1 M=1 mol dm$^{-3}$) and cooled in an ice bath. The precipitate was filtered and washed with cold 3 M HCl. The ivory solid was dried. The dried solid was taken up in THF and filtered to remove insoluble inorganic salt. The solution was dried over $MgSO_4$, filtered concentrated and dried under vacuum to give an ivory solid (693 mg, 97%): mp 352° C.; $^1$H-NMR (DMSO-d6, 400 MHz) δ 8.01 (d, 6H, J=8.0 Hz), 7.88 (s, 3H), 7.72 (d, 6H, J=8.0 Hz); $^{13}$C-NMR (DMSO-d6, 100 MHz) δ 166.6, 134.5, 131.8, 131.0 129.6, 126.0, 123.4, 90.3, 89.8; FT-IR (KBr, 4000-400 cm$^{-1}$) 3428 (br), 2994 (br), 2658 (w), 2534 (w), 2376 (w), 1687 (s), 1604 (s), 1518 (s), 1312 (s), 1277 (s), 1173 (w), 1105 (w), 856 (m), 768 (s); MALDI-TOF MS (m/z) [M]+ 510.0935 (found), 510.1103 (calcd. for $C_{33}H_{18}O_6$).

B. 4,4',4"-(Benzene-1,3,5-triyl-tris(benzene-4,1-diyl)) tribenzoic acid ($H_3BBC$) Trimethyl 4,4',4"-(benzene-1,3,5-triyl-tris(benzene-4,1-diyl))tribenzoate. Anhydrous 1,2-dimethoxyethane (150 mL) was placed in a two-neck 250-mL round bottom flask equipped with a magnetic stirring bar and a reflux condenser under nitrogen atmosphere. 4-Methoxy-carbonylphenylboronic acid (2.98 g, 16.6 mmol), CsF (5.03 g, 33.1 mmol), $Pd(PPh_3)_4$ (574 mg, 0.50 mmol), and 1,3,5-tris(4-bromo-phenyl) benzene (2.00 g, 3.68 mmol) were added to the flask, and the reaction mixture was refluxed for 48 h under nitrogen atmosphere. The solution was cooled to room temperature and evaporated under vacuum. The residue was dissolved in $CHCl_3$, washed with water and dried over $MgSO_4$. The solvent was evaporated under vacuum. Further purification was achieved by dissolving the product in 50 mL of diethyl ether and the solution was heated for 20 min and placed in the refrigerator for 1 h. The white product was collected by filtration and dried in vacuum overnight (2.1 g, 80%): mp 218° C.; $^1$H-NMR ($CDCl_3$, 400 MHz) δ 8.17 (d, 6H, J=8.0 Hz), 7.93 (s, 3H), 7.86 (d, 6H, J=8.4 Hz), 7.80 (d, 6H, J=8.4 Hz), 7.77 (d, 6H, J=8.4 Hz), 3.90 (s, 9H); $^{13}$C-NMR ($CDCl_3$, 100 MHz) δ 167.4, 145.4, 142.3, 141.1, 139.7, 130.6, 129.5, 128.3, 128.2, 127.4, 125.6, 52.6; FT-IR (KBr, 4000-400 cm$^{-1}$) 3428 (br), 2947 (w), 1932 (w), 1719 (s), 1607 (m), 1434 (m), 1277 (s), 1180 (s), 1110 (s), 1004 (m), 824 (s), 772 (s).

4,4',4"-(Benzene-1,3,5-triyl-tris(benzene-4,1-diyl)) tribenzoic acid. Trimethyl 4,4',4"-(benzene-1,3,5-triyl-tris (benzene-4,1-diyl))tribenzoate (2.00 g, 2.82 mmol), 2.2 g of NaOH, THF, water, and methanol (200, 80, and 50 mL, respectively) were mixed in a 1 L round bottom flask equipped with a magnetic stirring bar, and the mixture was stirred for 2 days at room temperature. The solution was evaporated under vacuum. The residue was acidified with 3 M HCl. The white solid was collected by filtration, washed with methylene chloride and methanol and dried in vacuum overnight (1.80 g, 96%): mp 326° C.; $^1$H-NMR (DMSO-d6, 400 MHz) δ 13.07 (br, 3H) 8.07 (d, 6H, J=8.0 Hz), 8.06 (s, 3H), 8.05 (d, 6H, J=8.0 Hz), 7.91 (d, 6H, J=7.6 Hz), 7.89 (d, 6H, J=7.2 Hz); $^{13}$C-NMR (DMSO-d6, 100 MHz) δ 168.0, 144.6, 141.9, 140.7, 139.2, 130.9, 130.6, 128.8, 128.4, 127.6, 125.3; FT-IR (KBr, 4000-400 cm$^{-1}$) 3448 (br), 3029 (br), 2661 (w), 2536 (w), 1925 (w), 1686 (s), 1606 (s), 1419 (m), 1276 (m), 1177 (m), 1118 (m), 1003 (m), 824 (s), 773 (s); MALDI-TOF MS (m/z) [M]+ 666.2976 (found), 666.2042 (calcd. for $C_{45}H_{30}O_6$).

Analytical techniques: Single-crystal X-ray diffraction data for MOF-200 were collected at 100 K using a Bruker Platinum 200 diffractometer with synchrotron radiation (λ=0.77490 Å) at Beamline 11.3.1 at the Advanced Light Source (ALS), Lawrence Berkeley National Laboratory. Single-crystal X-ray diffraction data for MOF-205 and MOF-210 were collected at 100 K using synchrotron radiation (λ=0.90000 Å (MOF-205), and 1.10000 Å (MOF-210), respectively) at beamlines 4A HFMX, and 6B MX-I. The diffraction data for MOF-180 were collected at 258 K on a Bruker APEX CCD diffractometer with CuKα (λ=1.54178 Å).

Powder X-ray diffraction data were collected using a Bruker D8 Discover θ-2θ diffractometer in reflectance Bragg-Brentano geometry at 40 kV, 40 mA (1,600 W) for CuKα1 radiation (λ=1.5406 Å). TGA was carried out using a TA Q500 and a Scinco TGA-S1000 thermal analysis system. Fourier transform infrared spectra (FT-IR) of samples prepared as KBr pellets were measured using a Nicolet FT-IR Impact 400 system and a JASCO FT/IR-4000 spectrophotometer.

Synthesis and Characterization of MOFs:

MOF-180. A solid mixture of $H_3BTE$ (7.5 mg, 0.015 mmol) and $Zn(NO_3)_2.6H_2O$ (75 mg, 0.25 mmol) was dissolved in a mixture of DMF/NMP (2.0/2.0 mL) in an 8-mL glass vial. The clear reaction solution was heated in an isotherm oven at 85° C. for 96 h resulting in colorless polyhedral crystals, which were isolated by washing with a mixture of DMF and NMP (3×4 mL) and dried in air. Yield: 5.2 mg, 27% based on 1 mol of $H_3BTE$. Elemental microanalysis for $Zn_4O(BTE)_2(H_2O)_3.H2O=C_{66}H_{32}O_{14}Zn_4$, calculated (%): C, 60.49; H, 2.46; N, 0.00. Found (%): C, 60.98; H, 2.54; N, 0.06. FT-IR (KBr, 4000-400 cm−1): 3422 (br, w), 1604 (s), 1534 (s), 1413 (vs), 1176 (w), 1016 (w), 875 (w), 859 (m), 779 (s), 743 (w), 698 (w), 677 (w), 609 (w), 523 (w), 446 (w), 405 (w).

MOF-200. A solid mixture of H3BBC (22.0 mg, 0.033 mmol) and $Zn(NO_3)_2.6H_2O$ (98.2 mg, 0.33 mmol) was dissolved in a mixture of DEF/NMP (4.0/4.0 mL) in a 20-mL glass vial. The clear reaction solution was heated in an isotherm oven at 85° C. for 24 h resulting in colorless trigonal prismatic crystals, which were isolated by washing with a mixture of DEF and NMP (3×4 mL) and dried in air. Yield: 30 mg, 29% based on 1 mol of $H_3BBC$. Elemental microanalysis for $Zn_4O(BBC)_2(H_2O)_3.H_2O=C_{90}H_{62}O_{17}Zn_4$, calculated (%): C, 64.46; H, 3.73; N, 0.00. Found (%): C, 64.42; H, 3.57; N, 0.00. FT-IR (KBr, 4000-400 cm−1): 1928 (w), 1800 (w), 1709 (m), 1612 (vs), 1566 (s), 1525 (s), 1408 (vs), 1184 (m), 1108 (w), 1006 (m), 869 (w), 828 (s), 787 (s), 706 (w), 655 (m), 558 (w), 512 (w).

MOF-200 (large scale synthesis). A solid mixture of $H_3BBC$ (200 mg, 0.30 mmol) and $Zn(NO_3)_2.6H_2O$ (950 mg, 3.19 mmol) was dissolved in a mixture of DEF/NMP (80/80 mL) in a 500-mL Nalgene® high-density polyethylene (HDPE) container. Reaction solution was sonicated for 1 h prior to heating, and then placed in an isothermal oven at 82° C. for 48 h to give the crystals of MOF-200 (150-170 mg, 44-50% yield based on 1 mol of H$_3$BBC).

MOF-205. A solid mixture of H$_3$BTB (12.8 mg, 0.029 mmol), and H$_2$NDC (10.5 mg, 0.049 mmol), and Zn (NO$_3$)$_2$·6H$_2$O (42.5 mg, 0.14 mmol) was dissolved in a mixture of DMF/EtOH (3.0/0.3 mL) in a 4-mL vial. The vial was capped and heated in an isothermal oven at 95° C. for 24 h to give colorless truncated-octahedral crystals. The reaction mixture was allowed to cool naturally to room temperature and the crystals were washed with DMF and dried in air. Yield: 21 mg, 68% based on 1 mol of H3BTB. Elemental microanalysis for MOF-205, Zn4O(BTB)4/3(NDC)≡C$_{48}$H$_{26}$O$_{13}$Zn$_4$, calculated (%): C, 53.78; H, 2.48; N, 0.00. Found (%): C, 53.58; H, 2.29; N, <0.1. FT-IR (KBr, 4000-400 cm$^{-1}$): 3335 (s, br), 1584 (vs), 1541 (vs), 1406 (vs), 1186 (m), 1141 (w), 1108 (w), 1015 (w), 921 (w), 854 (m), 779 (vs), 704 (m), 672 (w), 560 (w), 475 (m), 457 (m), 442 (m), 419 (w).

MOF-210. A solid mixture of H$_3$BTE (8.3 mg, 0.016 mmol), H$_2$BPDC (15.7 mg, 0.065 mmol), and Zn(NO$_3$)$_2$·6H$_2$O (42.5 mg, 0.14 mmol) was dissolved in a mixture of DMF/NMP (5.0/5.0 mL) in a 20-mL vial. The vial was capped and heated in an isothermal oven at 95° C. for 72 h to give colorless polyhedral crystals. The reaction mixture was allowed to cool naturally to room temperature and the crystals were washed with DMF and dried in air. Yield: 13 mg, 68% based on 1 mol of H3BTE. Elemental microanalysis for MOF-210, Zn$_4$O(BTE)$_{4/3}$(BPDC)≡C$_{58}$H$_{28}$O$_{13}$Zn$_4$, calculated based on framework only (%): C, 53.78; H, 2.48; N, 0.00. Found (%): C, 53.58; H, 2.29; N, <0.1. FT-IR (KBr, 4000-400 cm$^{-1}$): 3338 (s, br), 2206 (w), 1934 (w), 1654 (w), 1604 (vs), 1579 (vs), 1533 (vs), 1407 (vs), 1175 (m), 1098 (w), 1015 (w), 960 (w), 859 (m), 770 (s), 744 (w), 699 (w), 679 (w), 607 (w), 526 (w), 471 (w), 456 (m), 439 (m), 419 (m).

Single Crystal X-Ray Diffraction Analyses.

MOF-180. A colorless polyhedral crystal was sealed in a capillary, and its diffraction data set was collected at 258 K on a Bruker APEX CCD diffractometer with CuKα radiation (λ=1.54178 Å). Bruker SMART program was used for data collection, and SAINT was used for cell refinement, and reduction. Absorption correction was applied using SADABS. XPREP suggested a trigonal space group, P$\bar{3}$1c (No. 163) with a CFOM of 7.99. Since the space group is the same as MOF-177 (Zn$_4$O(BTB)$_2$), it is expected that the atomic connectivity of MOF-180 is also similar with that of MOF-177 (the qom net). Due to the weak diffraction intensities and low resolution (2.23 Å), only the Zn ions could be found. However, this resolution was sufficient for dissolving the Zn . . . Zn separation in a Zn$_4$O unit (about 3.2 Å) although it was not for other bonds involving light atoms such as CO and CC as well as ZnO bonds (~2.0 Å). In more detail, direct methods by XS in SHELX-TL software package suggested two unique Zn atoms (Zn1 and Zn2) belonging to one of two independent Zn$_4$O units in the asymmetric unit. The symmetry generated Zn atoms formed a tetrahedral arrangement with inter-atomic distances of about 3.4 Å. The third Zn atom examination on the electron density maps by WinGX (S13) indicated that a moiety of large electron densities was present around a special position (0.3333, 0.6667, 0.2500), which was ascribed to the other Zn$_4$O unit showing a disorder over two sites. Two oxygen atoms (O1C and O2C) were generated at the centers of the two Zn4O moieties; O1C and O2C sit on Wyckoff positions h and d, respectively. All the Zn atoms were refined anisotropically with application of restrains on interatomic distances and thermal parameters (DFIX and ISOR instructions in XL). Because of the very low and diffuse residual electron densities, it was not possible to identify the C and O atoms of the organic linkers. However, it was clear that noticeable electron densities were joining Zn$_4$O moieties and they corresponded to the BTE linkers (FIG. 4). Therefore, using the geometric information of a qom net, a model structure was built by incorporation of a BTE fragment into the crystal lattice using Materials Studio. The final structural model was obtained by Materials Studio Forcite calculations; both the positions of Zn$_4$O units and the unit cell parameters were not optimized. Due to the disordered one of two Zn$_4$O units, the bond geometry involving Zn and O atoms were deviated significantly from the ideal values, and therefore, the disordered Zn sites were finally adjusted manually using Materials Studio Visualizer. A part of the extended structure is in FIG. 5, and crystal and refinement data are given in Table 2. Crystallographic data for MOFS 180 has been deposited into the Cambridge Crystallographic Data Centre under deposition number CCDC 775690.

TABLE 2

Crystal data and structure refinement for MOF-180. The marked (*) results are based on Zn$_4$O moieties only.

| | |
|---|---|
| Empirical formula | C66H30O13Zn4 |
| Formula weight | 1292.38 |
| Temperature | 258(2) K |
| Wavelength | 1.54178 Å |
| Crystal system | Trigonal |
| Space group | P(-3)1c |
| Unit cell dimensions | a = 45.846(16) Å   α = 90° |
| | b = 45.846(16) Å   β = 90° |
| | c = 37.106(25) Å   γ = 120° |
| Volume | 67541(57) Å$^3$ |
| Z | 8 |
| Density (calculated) | 0.254 Mg/m$^3$ |
| Absorption coefficient | 0.415 mm$^{-1}$ |
| F(000) | 5200 |
| Crystal size | 0.25 × 0.25 × 0.25 mm$^3$ |
| Theta range for data collection | 1.11 to 20.20° |
| Index ranges | -20 <= h <= 20, -20 <= k <= 20, -16 <= l <= 16 |
| Reflections collected | 31726 |
| Independent reflections | 2136 [R(int) = 0.0798] |
| Completeness to theta = 20.20° | 99.8% |
| Absorption correction | SADABS |
| Refinement method | Full-matrix least-squares on F$^2$ |
| *Data/restraints/parameters | 2136/37/32 |
| *Goodness-of-fit on F$^2$ | 6.501 |
| *Final R indices [I > 2sigma(I)] | R1 = 0.5843, wR2 = 0.8725 |
| *R indices (all data) | R1 = 0.6190, wR2 = 0.8965 |
| *Largest diff. peak and hole | 1.105 and -0.319 e · Å$^{-3}$ |

Figure 6:
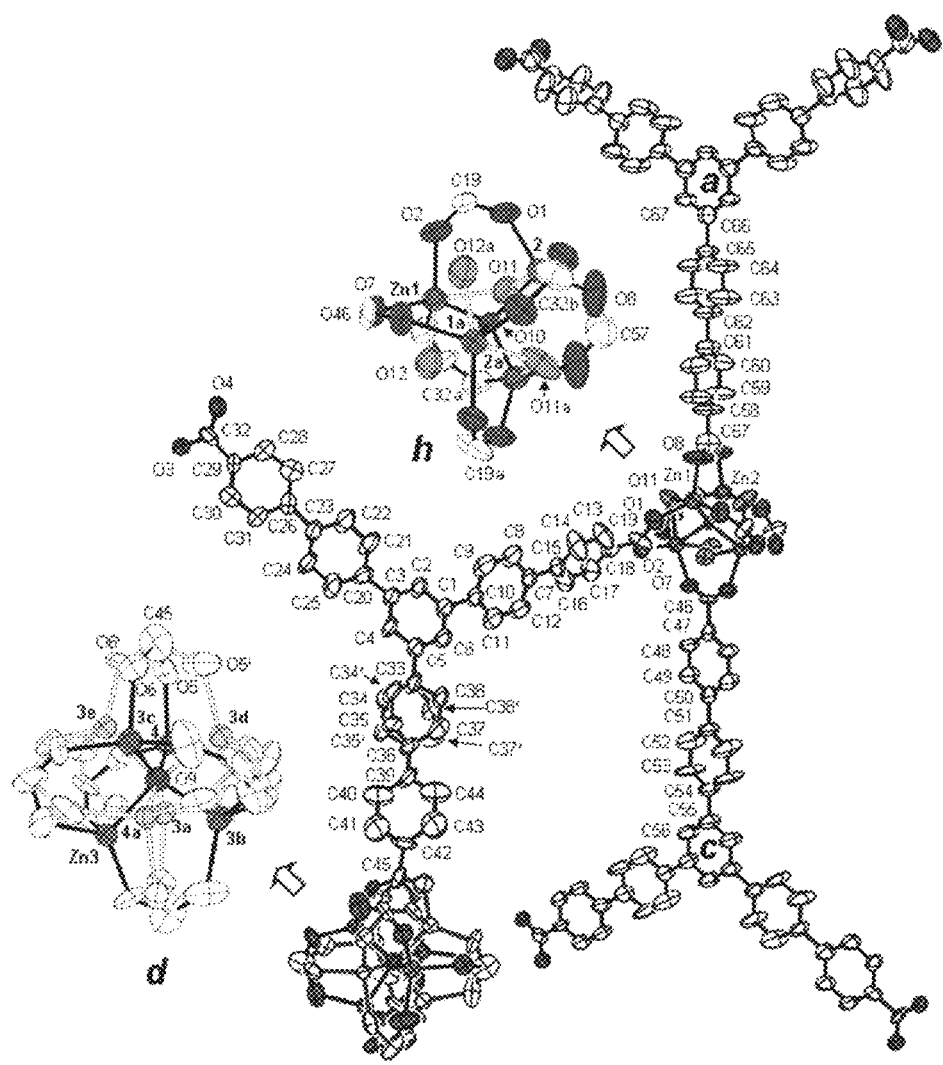
FIG. 6 is an ORTEP drawing (20% probability) of a fragment in MOF-200 is displayed with selected atomic labels. Two BBC and two $Zn_4O$ moieties lie at Wyckoff positions, a, c, d, and h. A $Zn_4O$ moiety at h has two $\mu$-$H_2Os$ and two dangling $H_2O$ which are displayed as pink ellipsoids. The other $Zn_4O$ moiety at d is disordered over two sites, which gives two sets of half-occupied Zn atoms denoted with blue filled sapheres, respectively.

MOF-200. Intensity data were collected at Beamline 11.3.1 at the Advanced Light Source (ALS), Lawrence Berkeley National Laboratory through the SCrALS (Service Crystallography at Advanced Light Source) program. The diffraction data set from a colorless trigonal prismatic crystal sealed in a capillary was collected at 100 K on a Bruker Platinum 200 diffractometer with synchrotron radiation (λ=0.77490 Å). Bruker APEX-2 program was used for data collection, and SAINT was used for cell refinement, and reduction. Absorption correction was applied using SADABS. Crystal structure was solved using SHELX-TL software package with a trigonal space group, P$\bar{3}$1c (No. 163). An initial model for MOF-200 was obtained by direct methods using XS, and improved by subsequent refinements using XL. Direct methods using a default TREF instruction in XS produced four Zn atoms and many electron density peaks that were difficult to extract ligand. Among four Zn atoms, two Zn atoms, Zn3 and Zn4 showed a statistical disorder over two sites. After fixing their site occupancy factors, and removing all other non-Zn atoms, phase expansion using a TEXP instruction with 2347 E0>1.5 was conducted to obtain an improved framework structure. There were three independent BBC links in the asymmetric unit. One lies at a general position and other two at special positions (Wyckoff positions, a and c, respectively) as shown in FIG. 6). Two independent $Zn_4O$ units were also found at special positions (Wyckoff positions, d and h, respectively). While a Zn4O unit at an h position is ordered, the other one at a d position was disordered over two sites. The latter case required one of three carboxylate groups in the ordered BBC to be present over two positions with a half occupancy. One of the benzene rings of the BBC was also statistically disordered over two sites. Due to tendencies of dynamic disorder of all BBC links, restraints by AFIX, SADI and FLAT instructions were applied to maintain ideal geometry of their aromatic rings. For C43 and C44 atoms, EADP instructions were applied to avoid eccentric thermal ellipsoids. All hydrogen except for coordinating water molecules were placed in calculated positions and refined by applying a riding model. Without including solvent molecules, the refinement converged to R1=0.1924, and wR2=0.4783 for 12,945 reflections of I>2σ(I). The large volume fraction of disordered solvents was calculated by PALTON SOLO CALC to 88444.1 Å3 which corresponds to 89.2% of the unit cell volume. PALTON SQUEEZE routine calculated that 10711 electrons per unit cell were attributed to the disordered solvents. With a modified reflection data excluding the solvent contribution, the final refinement process converged to R1=0.0686, wR2=0.1855 (I>2σ(I)). A part of the extended structure is in FIG. 6, and crystal and refinement data are given in Table 3. Crystallographic data for MOF-200 has been deposited into the Cambridge Crystallographic Data Centre under deposition number CCDC 775691.

TABLE 3

Crystal data and structure refinement for MOF-200.

| | |
|---|---|
| Empirical formula | C90H60O16Zn4 |
| Formula weight | 1658.86 |
| Temperature | 100(2) K |
| Wavelength | 0.77490 Å |
| Crystal system | Trigonal |
| Space group | P$\bar{3}$1c |
| Unit cell dimensions | a = 52.022(3) Å  α = 90° |
| | b = 52.022(3) Å  β = 90° |
| | c = 42.316(5) Å  γ = 120° |
| Volume | 99176(14) Å$^3$ |
| Z | 8 |
| Density (calculated) | 0.222 Mg/m$^3$ |
| Absorption coefficient | 0.202 mm$^{-1}$ |
| F(000) | 6784 |
| Crystal size | 0.30 × 0.30 × 0.20 mm$^3$ |
| Theta range for data collection | 2.15 to 18.14° |
| Index ranges | −41 <= h <= 41, −41 <= k <= 41, −33 <= l <= 33 |
| Reflections collected | 377015 |
| Independent reflections | 17914 [R(int) = 0.1164] |
| Completeness to theta = 18.14° | 99.5% |
| Max. and min. transmission | 0.9607 and 0.9419 |
| Refinement method | Full-matrix least-squares on F$^2$ |
| Data/restraints/parameters | 17914/387/615 |
| Goodness-of-fit on F$^2$ | 1.051 |
| Final R indices [I > 2sigma(I)] | R1 = 0.0686, wR2 = 0.1855 |
| R indices (all data) | R1 = 0.0914, wR2 = 0.2005 |
| Largest diff. peak and hole | 0.253 and −0.321 e · Å$^{-3}$ |

Figure 7:
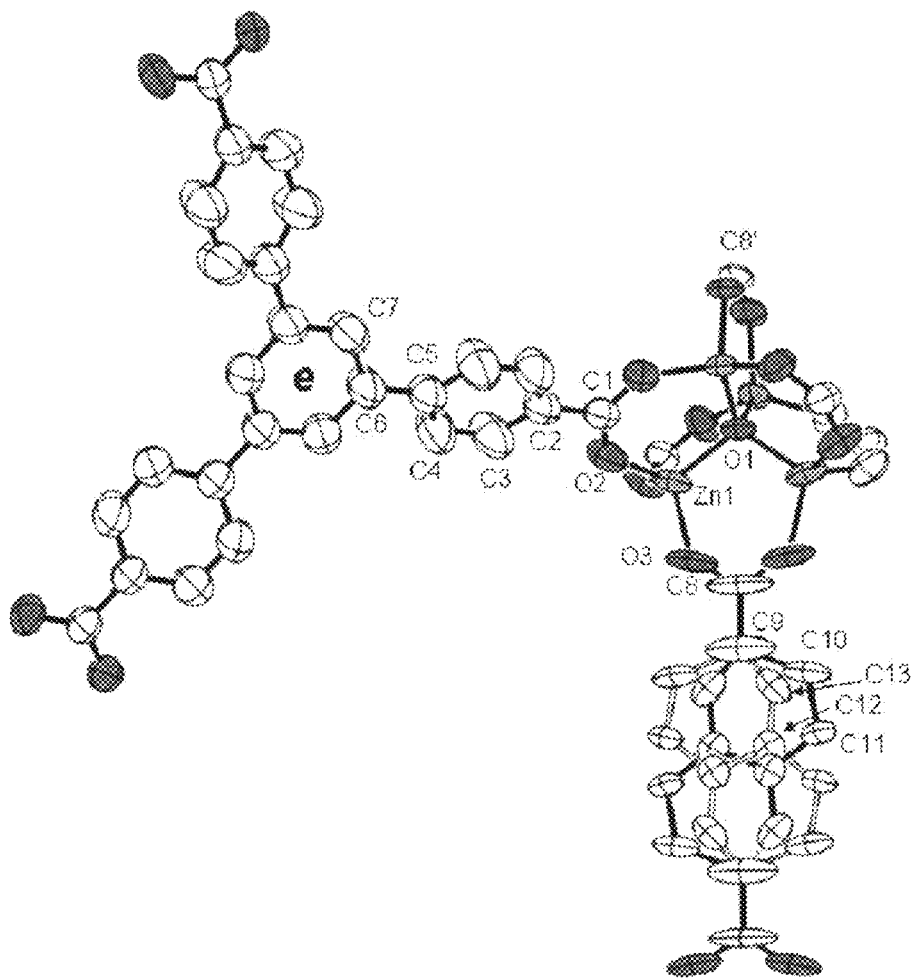
FIG. 7 is an ORTEP drawing (50% probability) of a fragment in MOF-205 is displayed with selected atomic labels. The labeled atoms constitute an asymmetric unit. A tripodal ligand, BTB sits on a special position having site symmetry of 32 (Wyckoff position, e at the center of BTB). The central oxo anion, O1 is also located at a special position (Wyckoff d position, $\bar{4}$ m2 site symmetry). The linear linker, NDC is disordered over two sites due to the crystallographic site symmetry, mm2 (Wyckoff position, h). Hydrogen atoms are omitted for simplicity. Six points of extension for the inorganic SBU are composed of two NDC carboxylate C atoms (C8 and C8') and the others belonging to four BTB linkers.

MOF-205. The diffraction data set from a colorless truncated octahedral crystal measuring 0.30×0.30×0.30 mm$^3$ mounted was collected at 100 K on a ADSC Quantum 210 CCD diffractometer with synchrotron radiation (λ=0.90000 Å) at Macromolecular Crystallography Wiggler Beamline 4A HFMX, Pohang Accelerator Laboratory (PAL), Pohang, Korea. ADSC Quantum-210 ADX program (Ver. 1.96) was used for data collection. HKL2000 (Ver. 0.98.699) (S18) was used for cell refinement, reduction, and absorption correction. Crystal structure was solved using SHELX-TL software package with a cubic space group, Pm$\bar{3}$n (No. 223). An initial model for MOF-205 was obtained by direct methods using XS, and improved by subsequent refinements using XL. Most non-hydrogen atoms in the framework were easily identified except for a disordered 2,6-naphthalenedicarboxylate (NDC) around a special position (Wyckoff position, h). Before resolving the disorder, other atoms were refined anisotropically to suppress noisy electron densities. As the molecular symmetry of NDC (C2h point group or m/2 if NDC is flat) is lower than the site symmetry (mm2) in the lattice, geometric restraints with DFIX were applied to prevent severe distortion of the naphthalene moiety. In NDC, two terminal carboxylate groups are parallel, but their C atoms not aligned in the same line. This required also a disordered model for the carboxylate. However, further resolution was not been applied, and instead, we have prepared an ordered carboxylate model for simplicity. As it is, the C8 and O3 atoms in the carboxylate have elongated ellipsoids normal to a crystallographic 2-fold rotation axis as shown in FIG. 7. All phenyl groups were refined with restrained models by applying DFIX and FLAT instructions. Hydrogen atoms were placed in calculated positions and refined by applying a riding model. As usually observed in highly porous and symmetric MOF structures, it was very difficult to find occluded solvent molecules from diffuse electron densities. Without including solvent molecules, the refinement converged to R1=0.1271, and wR2=0.3973 for 4,318 reflections of I>2σ(I). The large volume fraction of disordered solvent was calculated by PALTON SOLO CALC) to 23281.0 Å3 which corresponds to 83.3% of the unit cell volume. PALTON SQUEEZE routine calculated that 4551 electrons per unit cell were attributed to the disordered solvents. With a modified reflection data excluding the solvent contribution, the final refinement process converged to R1=0.0516, wR2=0.1579 (I>2σ(I)). A part of the extended structure is displayed in FIG. 7, and crystal and refinement data are given in Table 4. Crystallographic data for MOF-205 has been deposited into the Cambridge Crystallographic Data Centre under deposition number CCDC 775692.

TABLE 4

Crystal data and structure refinement for MOF-205.

| | |
|---|---|
| Empirical formula | C48H26O13Zn4 |
| Formula weight | 1072.17 |
| Temperature | 100(2) K |
| Wavelength | 0.90000 Å |
| Crystal system | Cubic |
| Space group | Pm$\bar{3}$n |
| Unit cell dimensions | a = 30.353(4) Å  α = 90° |
| | b = 30.353(4) Å  β = 90° |
| | c = 30.353(4) Å  γ = 90° |
| Volume | 27964(6) Å$^3$ |
| Z | 6 |
| Density (calculated) | 0.382 Mg/m$^3$ |
| Absorption coefficient | 0.524 mm$^{-1}$ |
| F(000) | 3228 |
| Crystal size | 0.30 × 0.30 × 0.30 mm$^3$ |
| Theta range for data collection | 1.70 to 32.37° |
| Index ranges | 0 <= h <= 36, −36 <= k <= 36, −36 <= l <= 36 |
| Reflections collected | 79057 |
| Independent reflections | 4318 [R(int) = 0.0982] |
| Completeness to theta = 32.37° | 98.5% |
| Absorption correction | multi-scan |

TABLE 4-continued

Crystal data and structure refinement for MOF-205.

| | |
|---|---|
| Refinement method | Full-matrix least-squares on $F^2$ |
| Data/restraints/parameters | 4318/65/99 |
| Goodness-of-fit on $F^2$ | 1.111 |
| Final R indices [I > 2σ(I)] | R1 = 0.0516, wR2 = 0.1579 |
| R indices (all data) | R1 = 0.0583, wR2 = 0.1623 |
| Largest diff. peak and hole | 0.378 and −0.574 e · Å$^{-3}$ |

Figure 9:
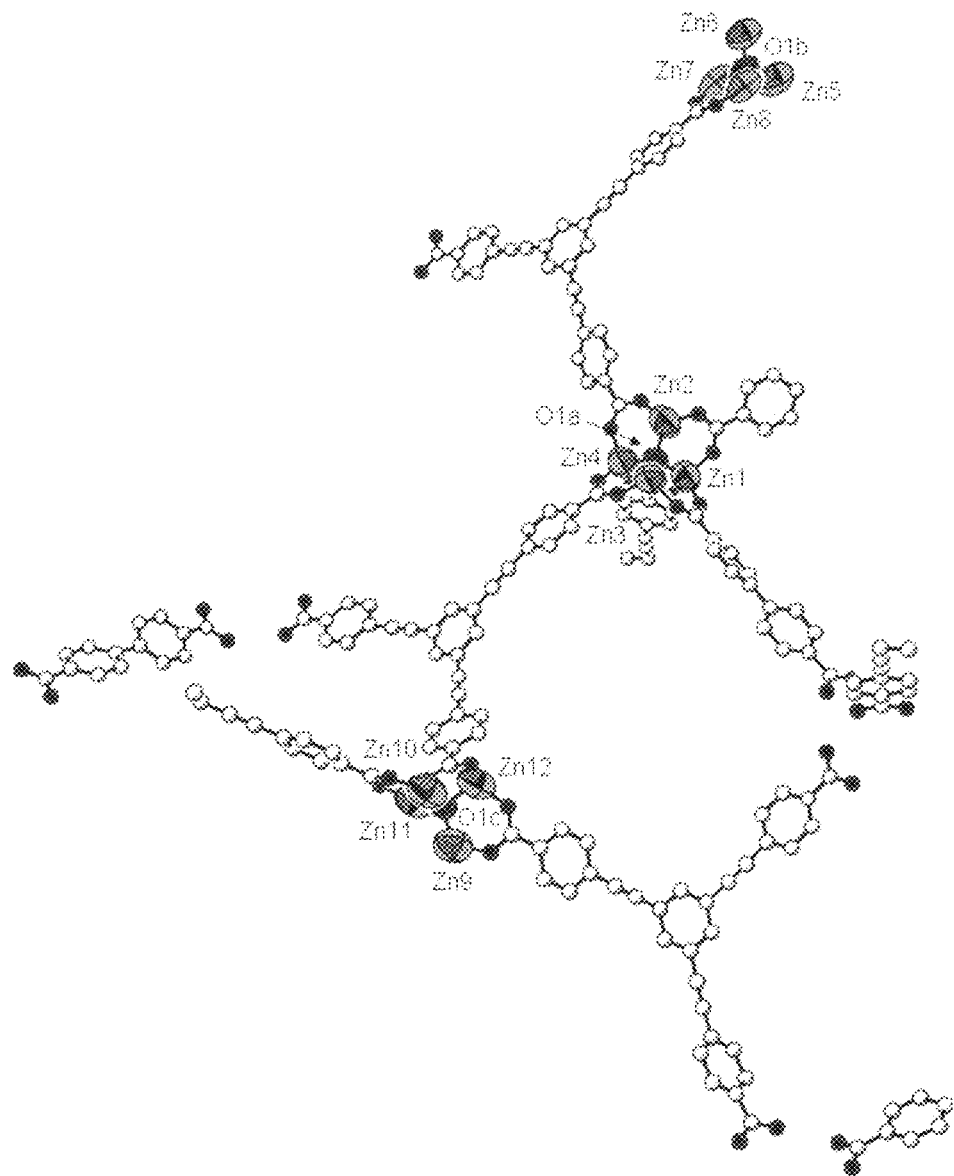
FIG. 9 is an ORTEP drawing of the asymmetric unit for MOF-210. Thermal ellipsoids are displayed with 20% probability.
Figure 10:
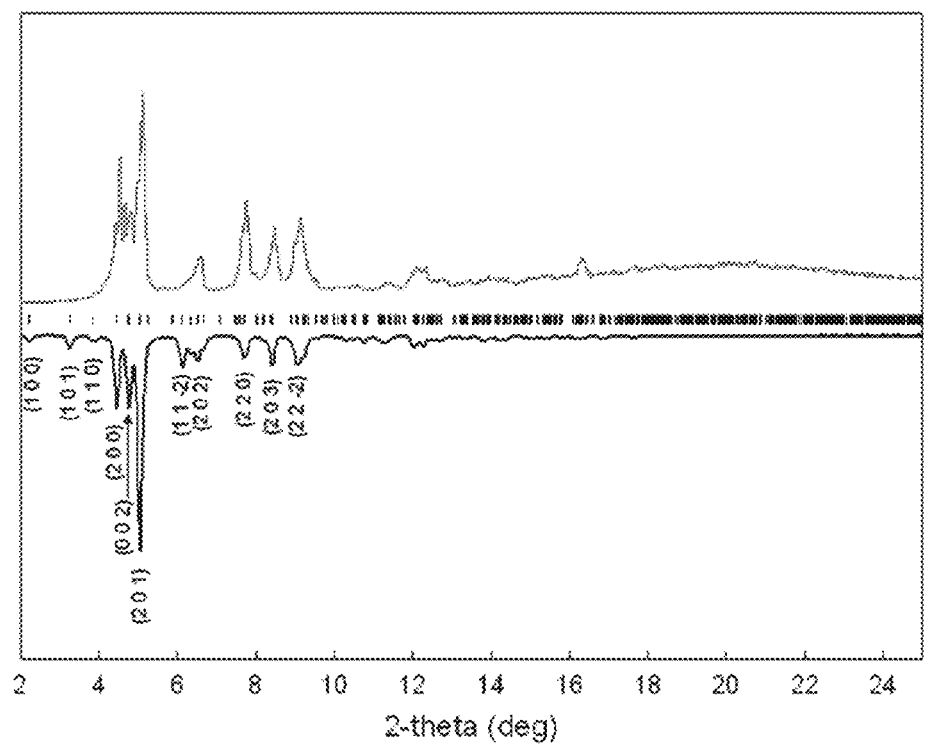
FIG. 10 is a comparison of the experimental PXRD patterns of MOF-180: (Top) MOF-180 as-prepared and simulated pattern (bottom) from a modeling structure.
Figure 11:
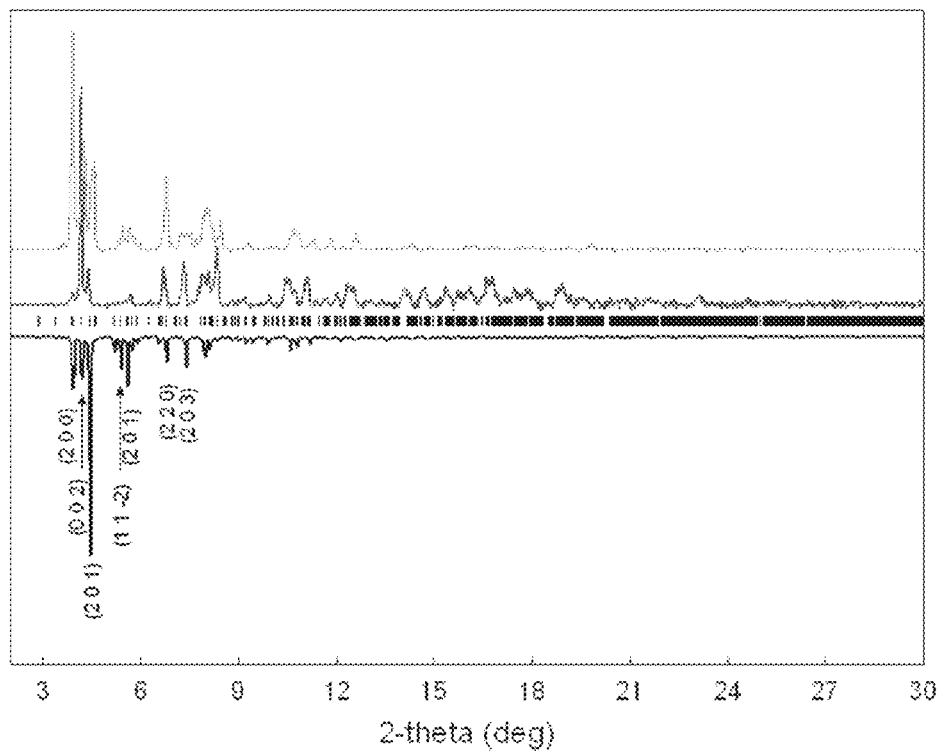
FIG. 11 is a comparison of the experimental PXRD patterns of MOF-200: as-prepared (middle line), evacuated after activated (top line), and simulated pattern (bottom line) from single-crystal X-ray data.
Figure 12:
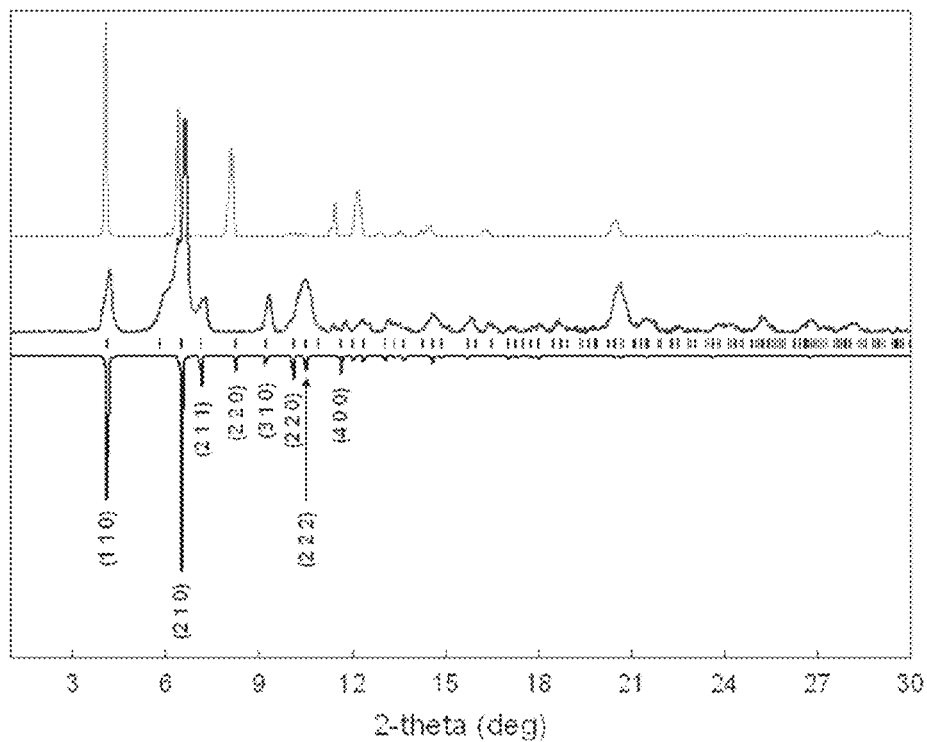
FIG. 12 is a comparison of the XRD patterns of MOF-205; as-prepared (middle line), activated (top line) and simulated (bottom line) from single-crystal X-ray data.
Figure 13:
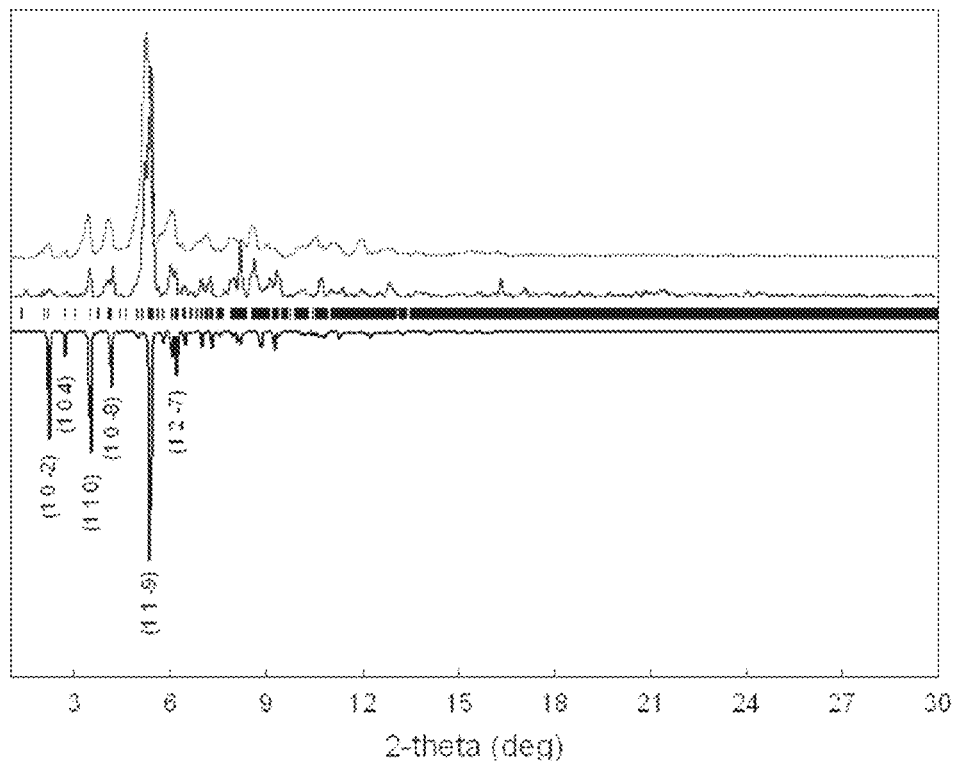
FIG. 13 is a comparison of the XRD patterns of MOF-210; as-prepared (middle line), activated (top line) and simulated (bottom line) from single-crystal X-ray data.
Figure 14:
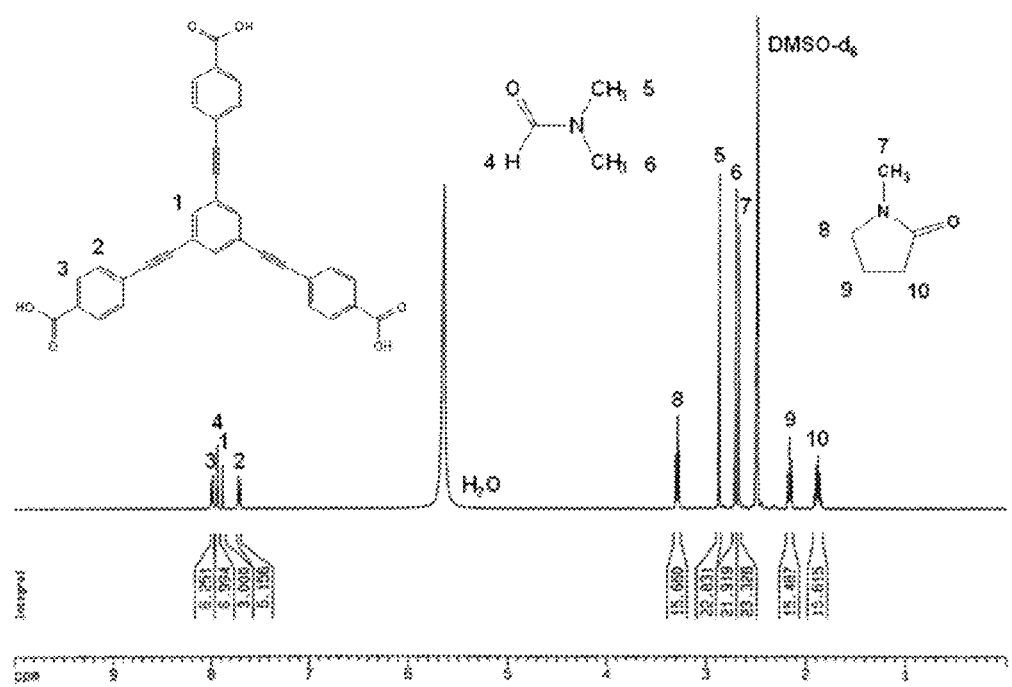
FIG. 14 is a $^1$H-NMR spectrum for as-prepared MOF-180 after digesting in DCl/DMSO-$d_6$ solution. The integration value of 26.8 at peaks 1 to 3 is attributed to 15 aromatic protons of $H_3$BTE. Comparing to the integration of BTE, 7.4 DMF (peaks 4 to 6, 51.7 H) and 7.8 NMP (peaks 7 to 10, 70.1 H) were also observed. From the molar ratio, the empirical formula has been estimated to be $Zn_4O(BTE)_2 \cdot (DMF)_{14.8}(NMP)_{15.6}$.
Figure 15:
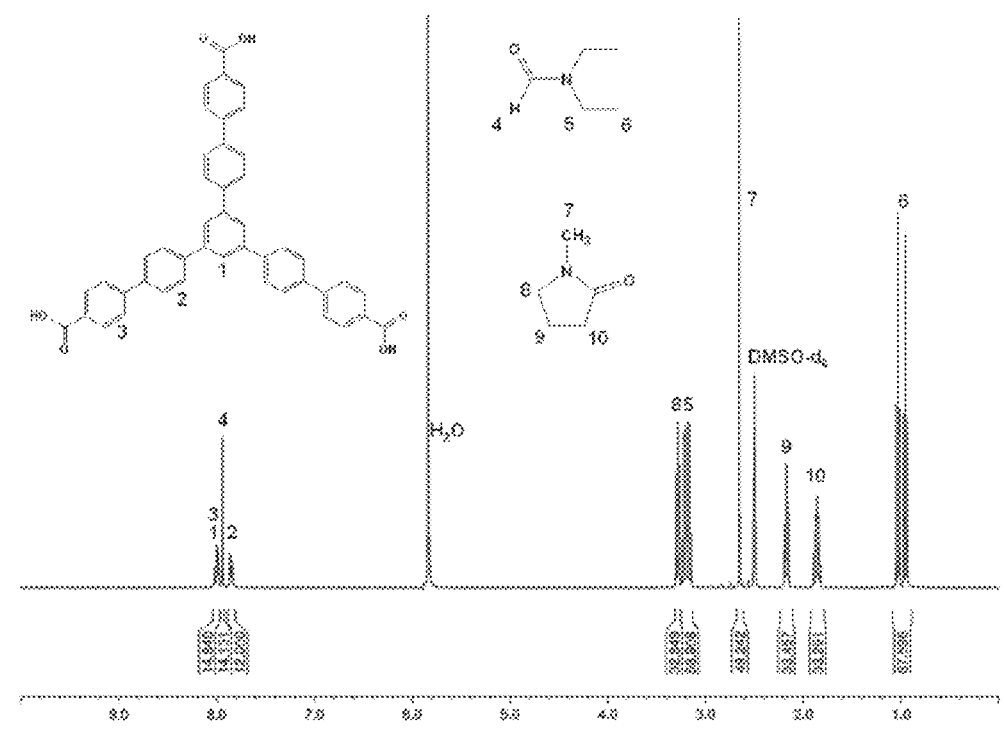
FIG. 15 is a $^1$H-NMR spectrum for as-prepared MOF-200 after digesting in DCl/DMSO-$d_6$ solution. The integration value of 26.8 at peaks 1 to 3 is attributed to 27 aromatic protons of H$_3$BBC. Comparing to the integration of BBC, 14.7 DEF (peaks 4 to 6, 160.6 H) and 16.6 NMP (peaks 7 to 10, 148.8 H) were also observed. From the molar ratio, the empirical formula has been estimated to be Zn$_4$O(BBC)$_2$(H$_2$O)$_3$·(DEF)$_{29.4}$(NMP)$_{33.2}$.
Figure 16:
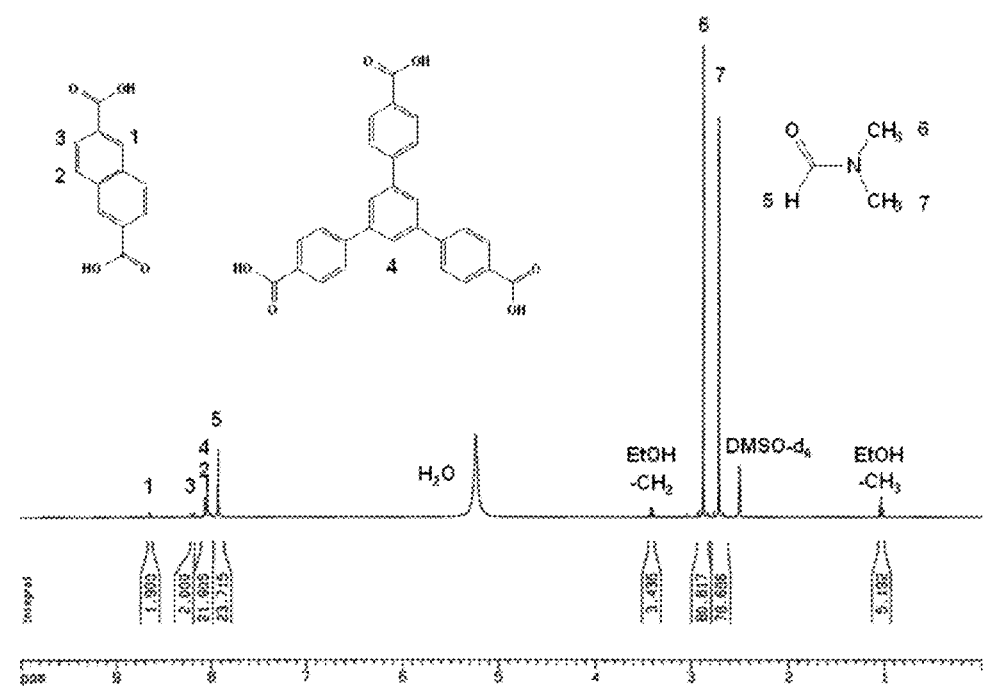
FIG. 16 is a $^1$H-NMR spectrum for as-prepared MOF-205 after digesting in DCl/DMSO-d$_6$ solution. The integration value of 25.8 at peaks 1 to 4 is attributed to 26 aromatic protons, which corresponds to 20 and 6 H of 4/3 H$_3$BTB and 1 H$_2$NDC, respectively. Comparing to the integration of BTB/NDC, 26.4 DMF (peaks 5 to 7, 183.3 H) and 1.7 EtOH (8.69 H) were also observed. From the molar ratio, the empirical formula has been estimated to be Zn$_4$O(BTB)$_{4/3}$(NDC).(DMF)$_{26.4}$(EtOH)$_{1.7}$.
Figure 17:
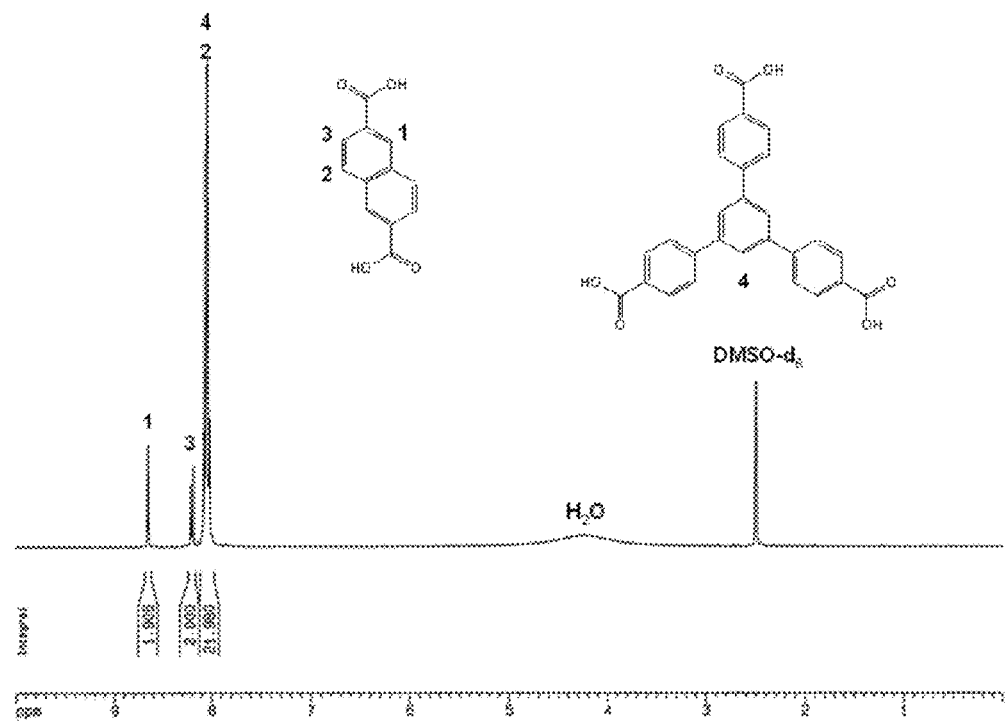
FIG. 17 is a $^1$H-NMR spectrum for guest-free MOF-205 after digesting in DCl/DMSO-d$_6$ solution. From the integration of peaks 1 and 3 (3.906 H), integration for H$_3$BTB (peak 4, aromatic proton only) is estimated to be 19.98 when the integration of peak 2 is 2 H. Based on the ratio of the integration of the peaks (19.98:5.906=4/3 BTB:NDC), the empirical formula has been estimated to be Zn$_4$O(BTB)$_{4/3}$(NDC).
Figure 18:
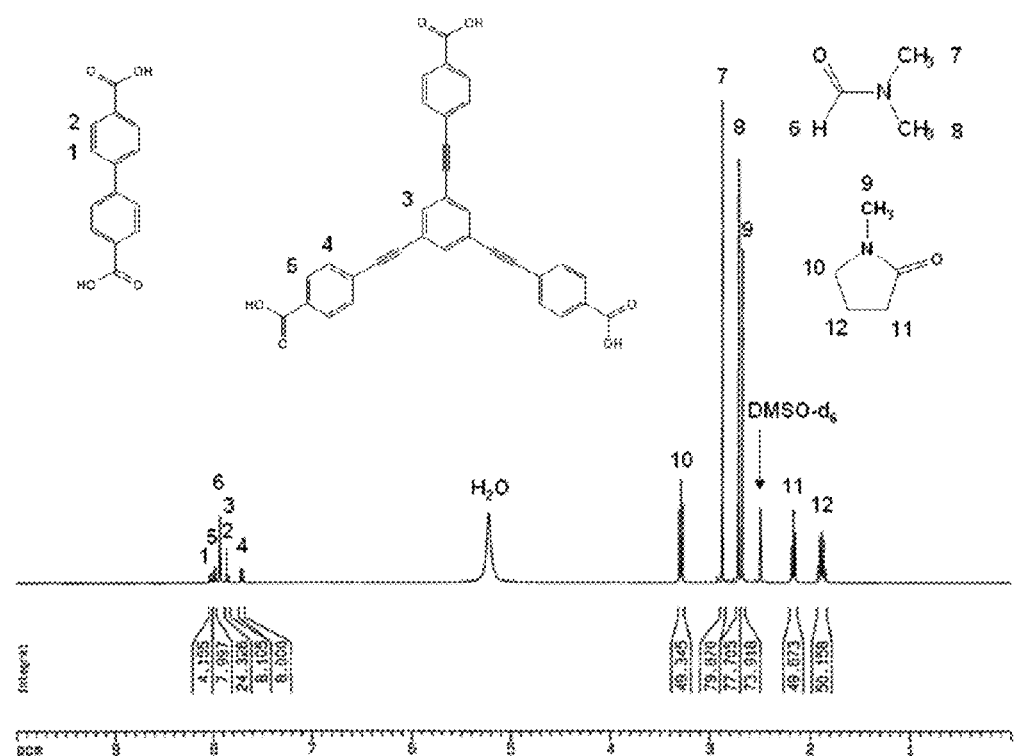
FIG. 18 is a $^1$H-NMR spectrum for as-prepared MOF-210 after digesting in DCl/DMSO-d$_6$ solution. The integration value 28.3 at peaks 1 to 5 is attributed to 28 aromatic protons, which corresponds to 20 and 8 H of 4/3 H3BTE and 1 H$_2$BPDC, respectively. Comparing to the integration of BTE/NDC, 25.7 DMF (peaks 6 to 8, 180 H) and 24.6 NMP (peaks 9 to 11, 221 H) were also observed. From the molar ratio, the empirical formula has been estimated to be Zn$_4$O(BTE)$_{4/3}$(BPDC)·(DMF)$_{25.7}$(NMP)$_{24.6}$.
Figure 19:
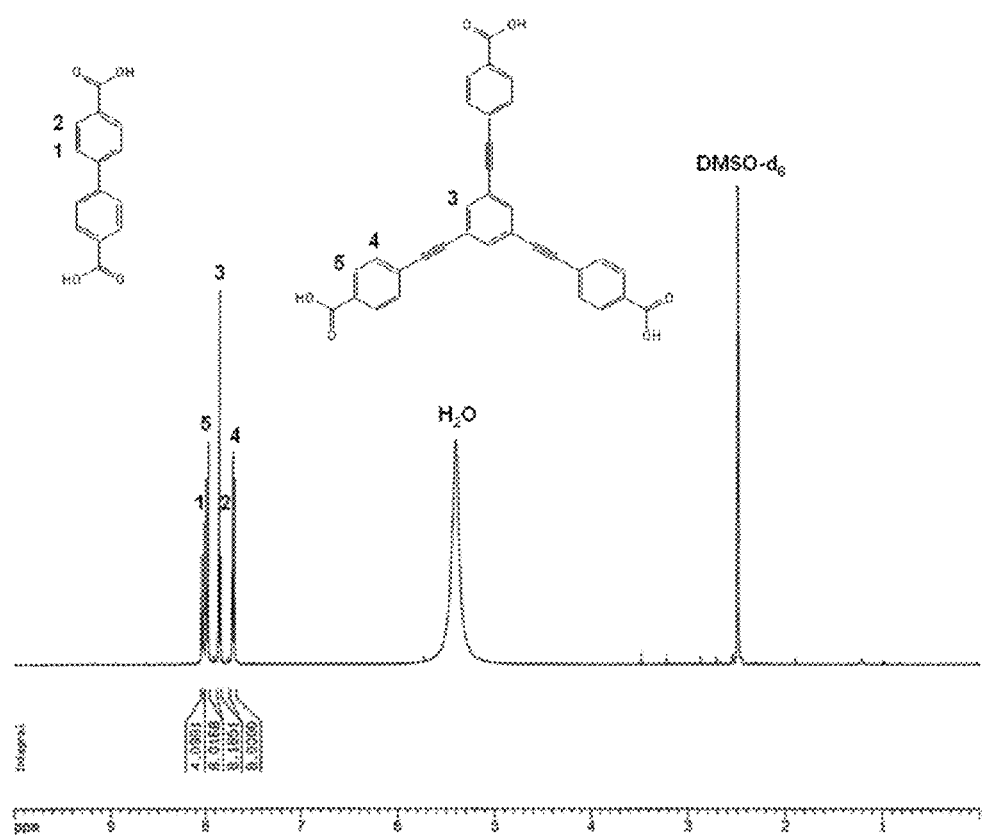
FIG. 19 is a $^1$H-NMR spectrum for guest-free MOF-210 after digesting in DCl/DMSO-d$_6$ solution. Based on the ratio of the integration of the peaks (20.1:8.2=4/3 BTE:BPDC), the empirical formula has been estimated to be Zn$_4$O(BTE)$_{4/3}$(BPDC).
Figure 20:
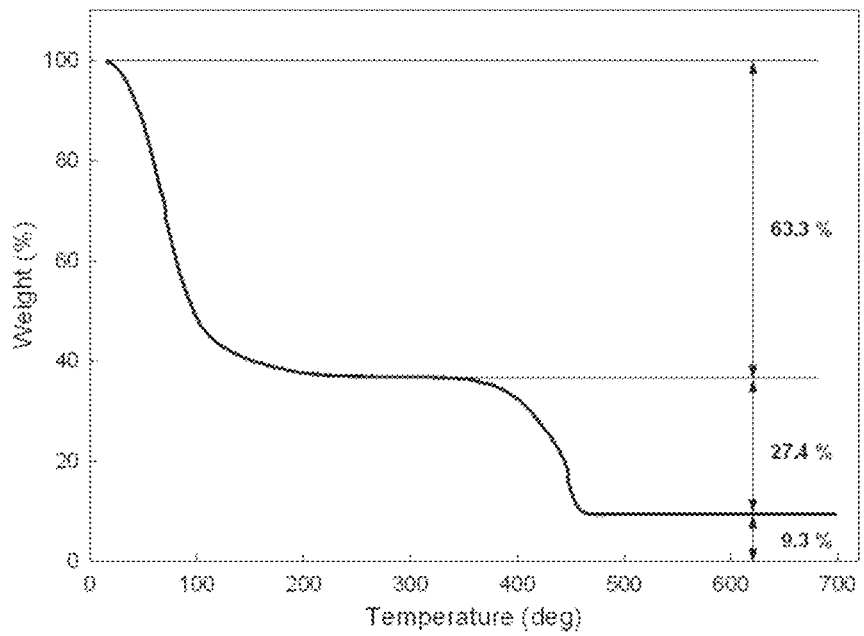
FIG. 20 is a TGA trace for as-prepared MOF-180.
Figure 21:
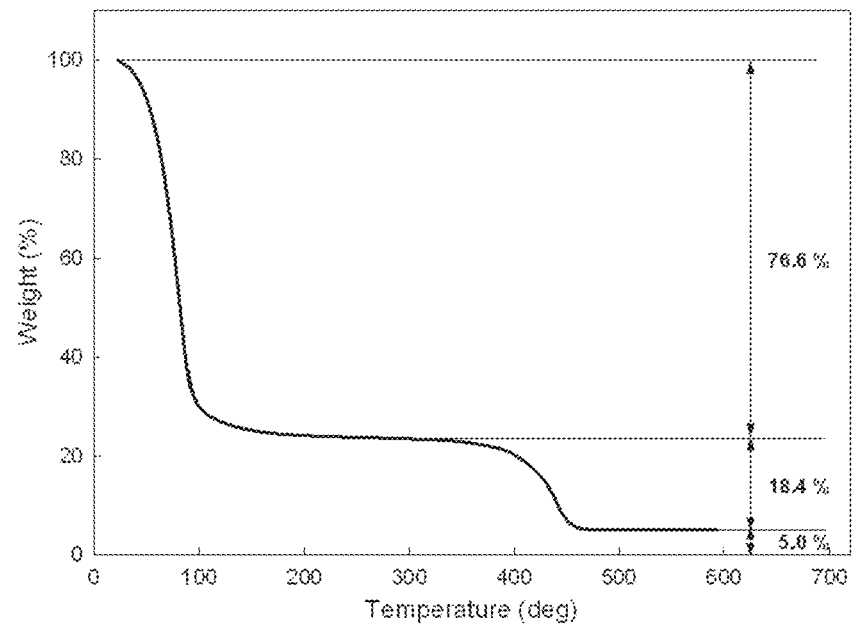
FIG. 21 is a TGA trace for as-prepared MOF-200.
Figure 22:
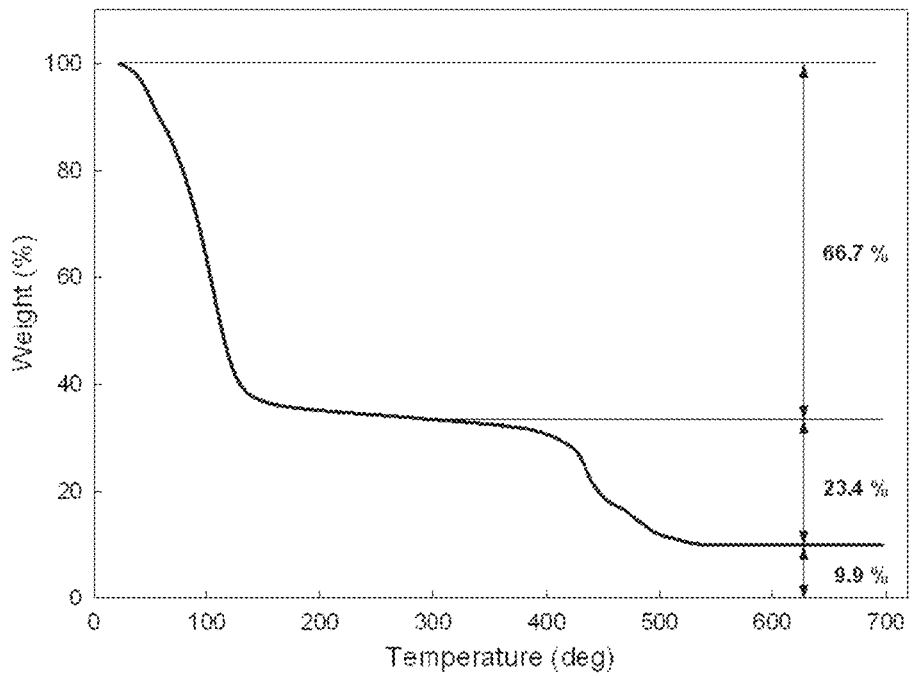
FIG. 22 is a TGA trace for as-prepared MOF-205.
Figure 23:
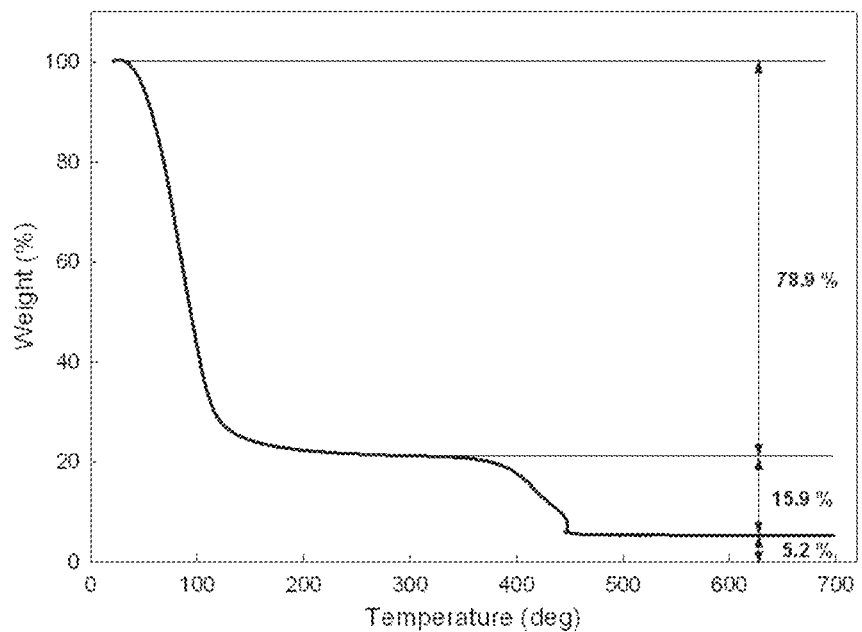
FIG. 23 is a TGA trace for as-prepared MOF-210.

MOF-210. The diffraction data set from a fragment cut from a twinned crystal measuring 0.35×0.30×0.25 mm$^3$ mounted was collected at 100 K with synchrotron radiation (λ=1.10000 Å) on a 6B MX-I ADSC Quantum-210 detector with a silicon (111) doublecrystal monochromator at the Pohang Accelerator Laboratory, Korea. The ADSC Quantum-210 ADX program (Ver. 1.96) was used for data collection, and HKL2000 (Ver. 0.98.699) was used for cell refinement, reduction, and absorption correction. Although we mounted more than twenty crystals, the best data has only a low resolution of 1.9 Å, a combinational approach using X-ray crystallography and a structural modeling has been applied to build the structure of MOF-210 similarly to the case of MOF-180. The Zn atoms were found with a trigonal space group, R$\bar{3}$ (No. 148), by direct methods using XS in the SHEX-TL program package. Three sets of tetrahedrally-arranged Zn4 clusters were identified and refined anisotropically. The central oxygen atoms were introduced in the center of four Zn atoms per each Zn4 unit. With bond distance restraints using SADI instructions, the geometries of Zn$_4$O clusters were maintained during refinements. Three central oxygen atoms were also refined anisotropically. At this stage, some oxygen atoms coordinated to Zn atoms were shown in the difference Fourier map. However, incorporation of those atoms could not contribute for the expansion of the structural model. The R1 value was converged to 0.4698 for 9129 observed reflections (I>2σ(I)) among 14547 unique reflections. The BTE and BPDC organic linkers were inserted based on both electron density-map analyses and with consideration on the Zn$_4$O . . . Zn$_4$O distances (FIG. 8). Four independent Zn$_4$O clusters in an asymmetric unit require four BTE and three BPDC links which could be generated using a Materials Studio modeling program. The structural model was finally optimized by the geometry optimization using Materials Studio Forcite routine with fixing both Zn$_4$O positions and unit cell parameters. The final coordinates were generated in a SHELX ins-file, and further refinements were tried to investigate whether the model would give reduced R-values. However, the refinement processes diverged due to distortion of organic moieties; therefore, refinements with a 'DMAP 0 0' instruction were performed to generate a CIF-file. PLATON ADSYMM indicated the presence of pseudo-symmetry and suggested R$\bar{3}$c (No. 167) with 88% probability. In fact, the structure could be also solved with R$\bar{3}$c, which gave the same framework connectivity as that for the lower space group, R3. However, PLATON ADSYMM EXACT calculation supports R3, and there were many reflections that violated systematic absence conditions in R$\bar{3}$c; 224 reflections (average I, 90.0; average I/σ(I), 20.9) violated a reflection condition for the c-glide plane n R$\bar{3}$c. A part of the extended structure is shown in FIG. 9, and crystal and refinement data are shown in Table 5. Crystallographic data for MOF-205 has been deposited into the Cambridge Crystallographic Data Centre under deposition number CCDC 775693.

TABLE 5

Crystal data and structure refinement for MOF-210. The marked (*) results are based on Zn$_4$O moieties only.

| | |
|---|---|
| Empirical formula | C58H28O13Zn4 |
| Formula weight | 1194.28 |
| Temperature | 100(2) K |
| Wavelength | 1.10000 Å |
| Crystal system | Trigonal |
| Space group | R$\bar{3}$ |
| Unit cell dimensions | a = 50.745(1) Å  α = 90° |
| | b = 50.745(1) Å  β = 90° |
| | c = 194.256(5) Å  γ = 120° |
| Volume | 433203(16) Å$^3$ |
| Z | 54 |
| Density (calculated) | 0.247 Mg/m$^3$ |
| Absorption coefficient | 0.428 mm$^{-1}$ |
| F(000) | 32400 |
| Crystal size | 0.35 × 0.30 × 0.25 mm$^3$ |
| Theta range for data collection | 1.08 to 16.80° |
| Index ranges | 0 <= h <= 26, −22 <= k <= 0, |
| | −101 <= l <= 101 |
| Reflections collected | 14547 |
| Independent reflections | 14547 [R(int) = 0.0000] |
| Completeness to theta = 16.80° | 99.3% |
| Refinement method | Full-matrix least-squares on $F^2$ |
| *Data/restraints/parameters | 14547/81/767 |
| *Goodness-of-fit on $F^2$ | 4.458 |
| *Final R indices [I > 2sigma(I)] | R1 = 0.4698, wR2 = 0.8118 |
| *R indices (all data) | R1 = 0.5127, wR2 = 0.8305 |
| *Largest diff. peak and hole | 0.438 and −0.325 e · Å$^{-3}$ |

Thermal Gravimetric Analyses.

MOF-180 and 200 samples were heated at a constant rate of 5° C. min$^{-1}$ up to 700° C. on a TA Instruments Q-500 series thermal gravimetric analyzer in ambient atmosphere. MOF-205 and 210 samples were heated at a constant rate of 5° C. min$^{-1}$ up to 700° C. in ambient atmosphere on a Scinco TGA-S1000 apparatus. When the samples contain guest molecules, two distinguishable weight losses were observed before the final plateau. The first large decrease in weight % is due to the evaporation of occluded guest molecules. The weight loss probably due to the framework destruction was observed at between 300 to 500° C. In the case of mixed link MOFs, there were small shoulder traces in the TGA curve because of the difference in the decomposition temperature of the links. The estimation on the guest contents based on the TAG analysis was in good agreement with the results obtained by the $^1$H-NMR experiments.

Grand Canonical Monte Carlo Simulations & Geometric Area Calculations.

Atomistic grand canonical Monte Carlo (GCMC) simulations were performed to obtain nitrogen isotherms in MOF-200 and MOF-210. Prior to GCMC simulations density functional theory (DFT) calculations were performed for each MOF to derive partial charges of the MOF atoms which are needed to calculate the electrostatic interaction energy between atoms during the GCMC simulations.

Figure 24:
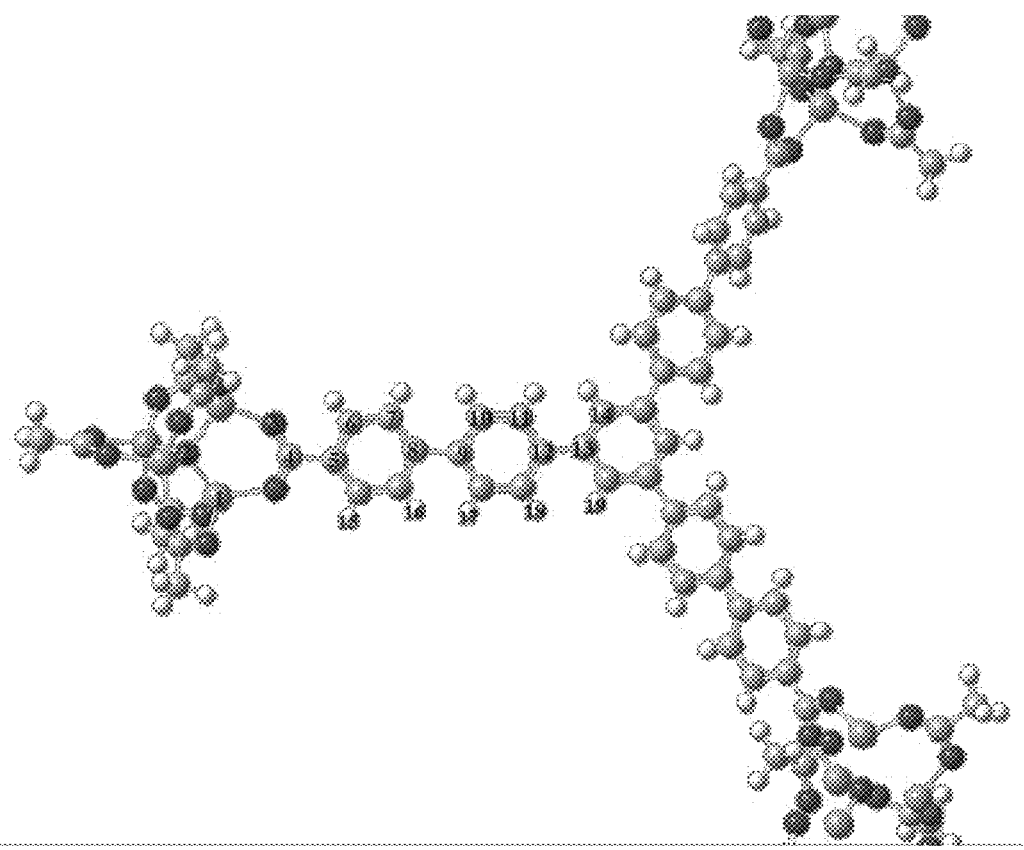
FIG. 24 shows a cluster used for deriving partial charges on MOF-200 atoms.
Figure 25:
FIG. 25 shows a cluster used for deriving partial charges on MOF-210 atoms.
Figure 26:
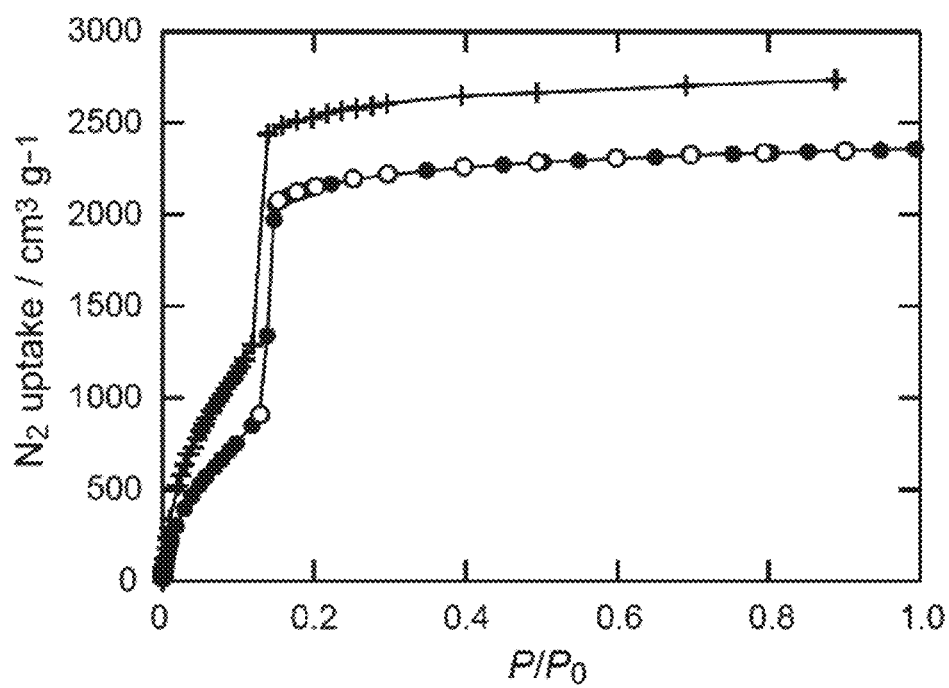
FIG. 26 shows simulated N$_2$ isotherm for MOF-200 (+). Experimental data were overlaid (circles).
Figure 27:
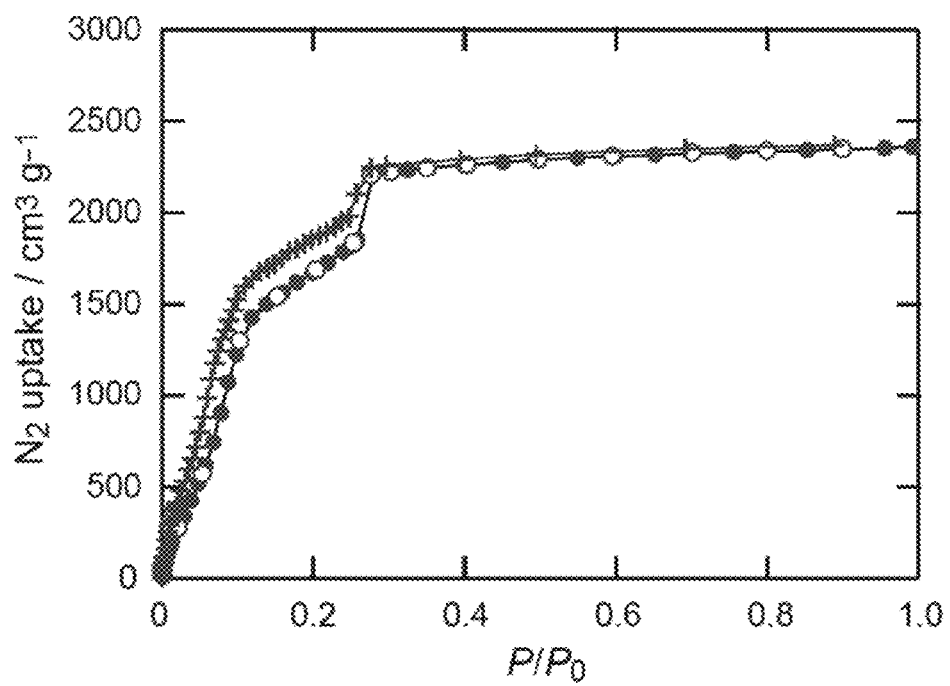
FIG. 27 shows simulated N$_2$ isotherm for MOF-210 (+). Experimental data were overlaid (circles).
Figure 28:
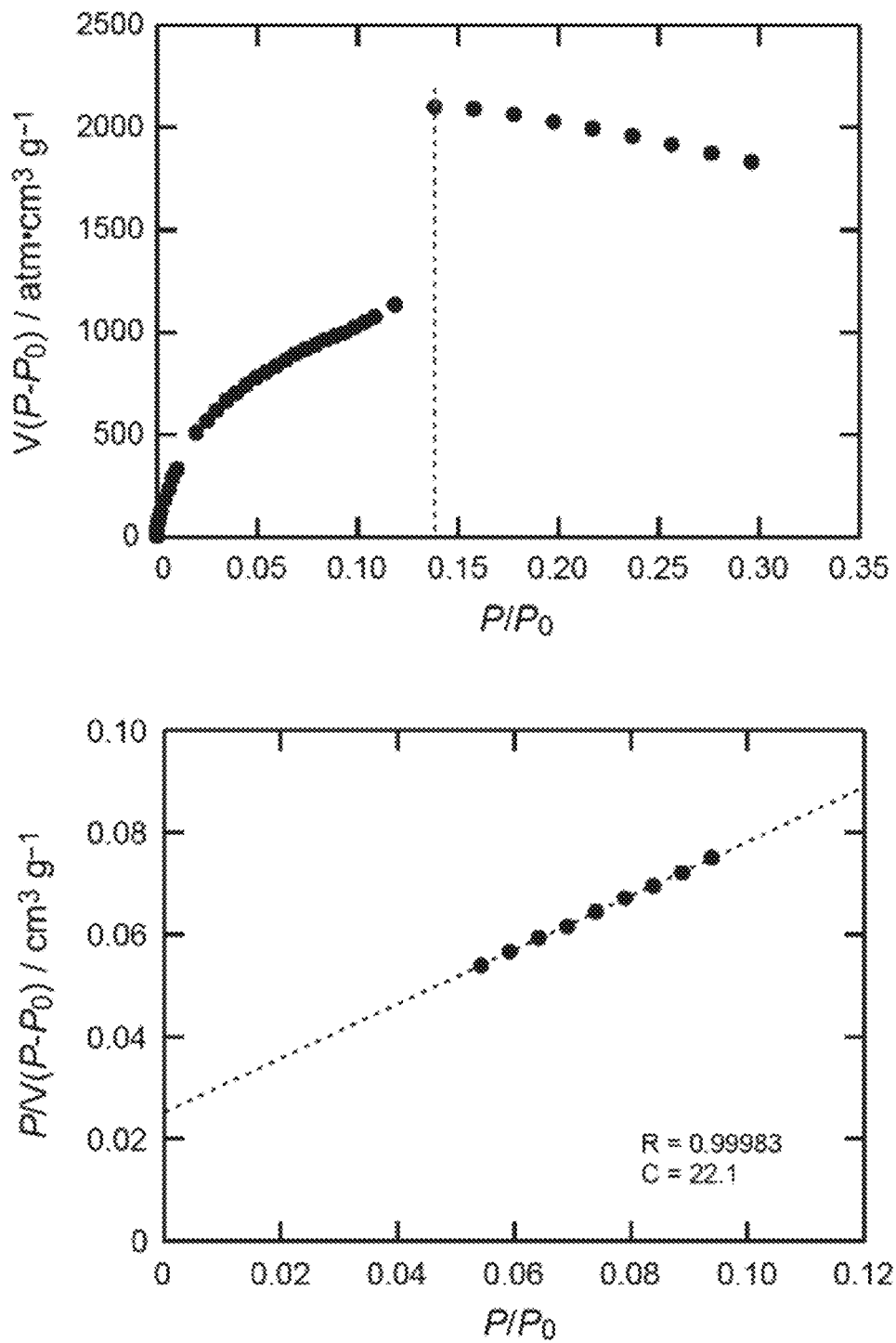
FIG. 28 shows V(P$_0$–P) vs. P/P$_0$ for simulated MOF-200 isotherm (top). Only the range below P/P$_0$=0.14 satisfies the first consistency criterion for applying the BET theory. (Bottom) Plot of the linear region for the BET equation.
Figure 29:
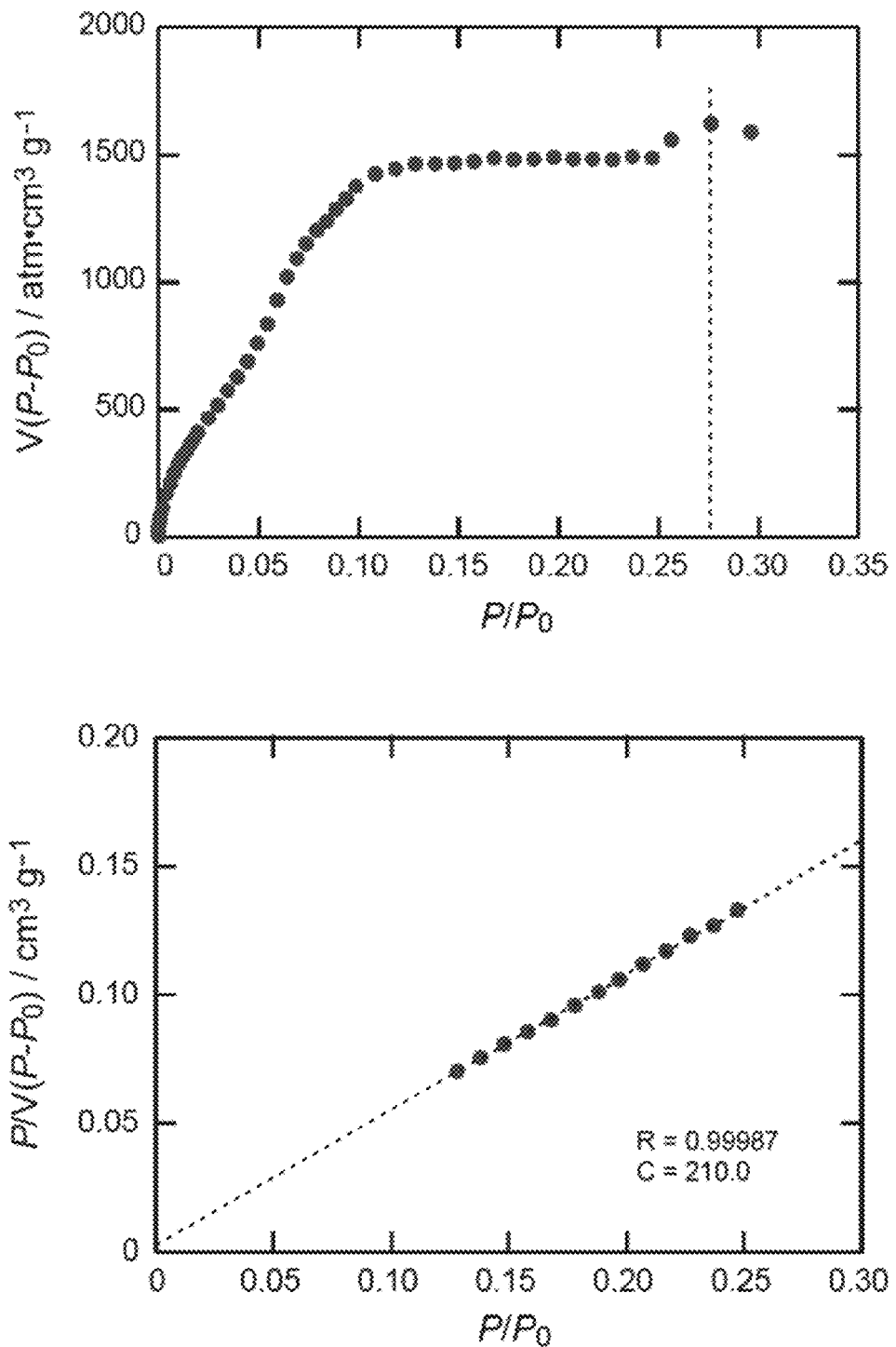
FIG. 29 shows V(P$_0$–P) vs. P/P$_0$ for simulated MOF-210 isotherm (top). Only the range below P/P$_0$=0.27 satisfies the first consistency criterion for applying the BET theory. (Bottom) Plot of the linear region for the BET equation.
Figure 30:
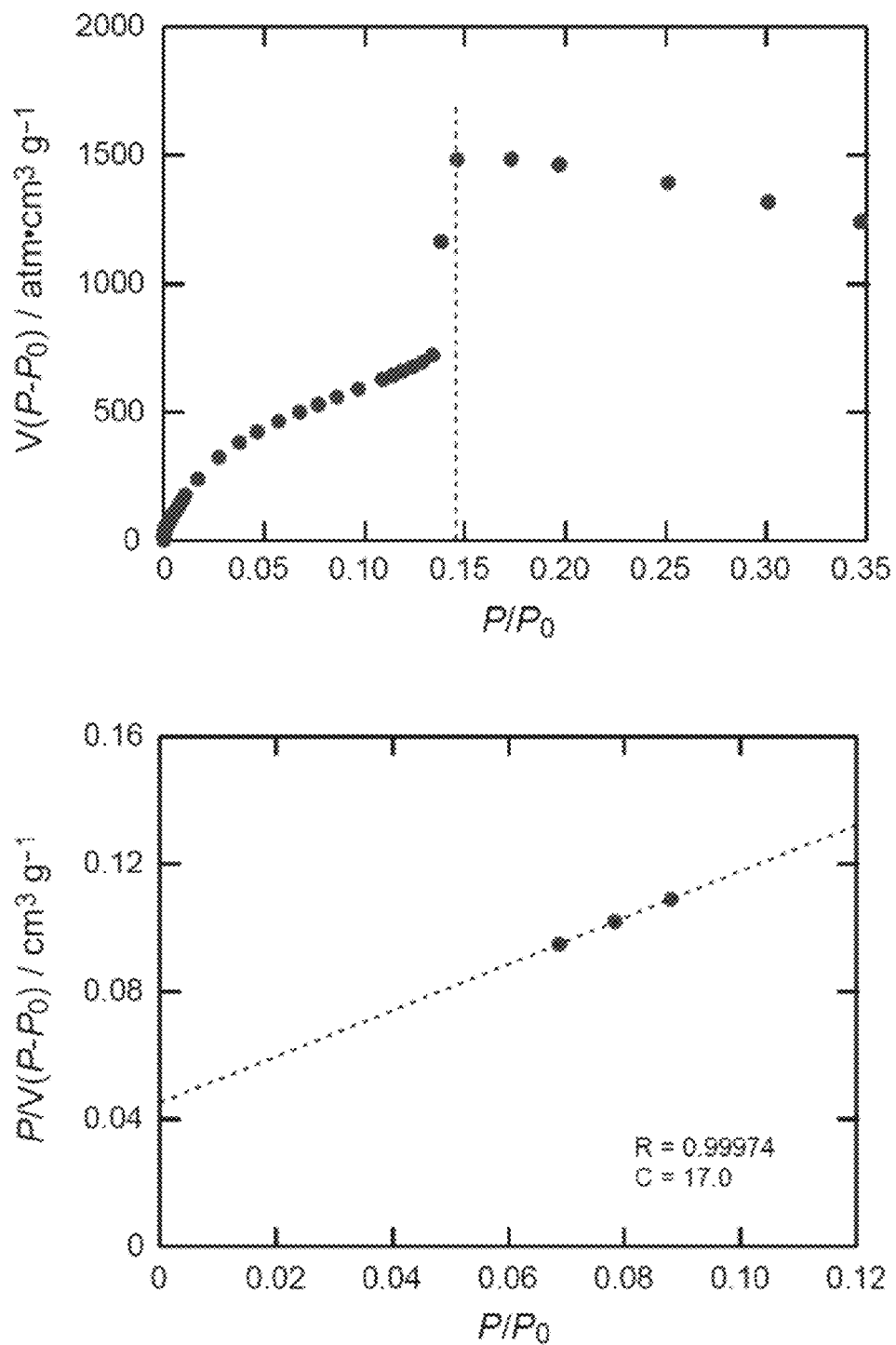
FIG. 30 shows V(P$_0$–P) vs. P/P$_0$ for MOF-200 (top). Only the range below P/P$_0$=0.14 satisfies the first consistency criterion for applying the BET theory. (Bottom) Plot of the linear region for the BET equation.
Figure 31:
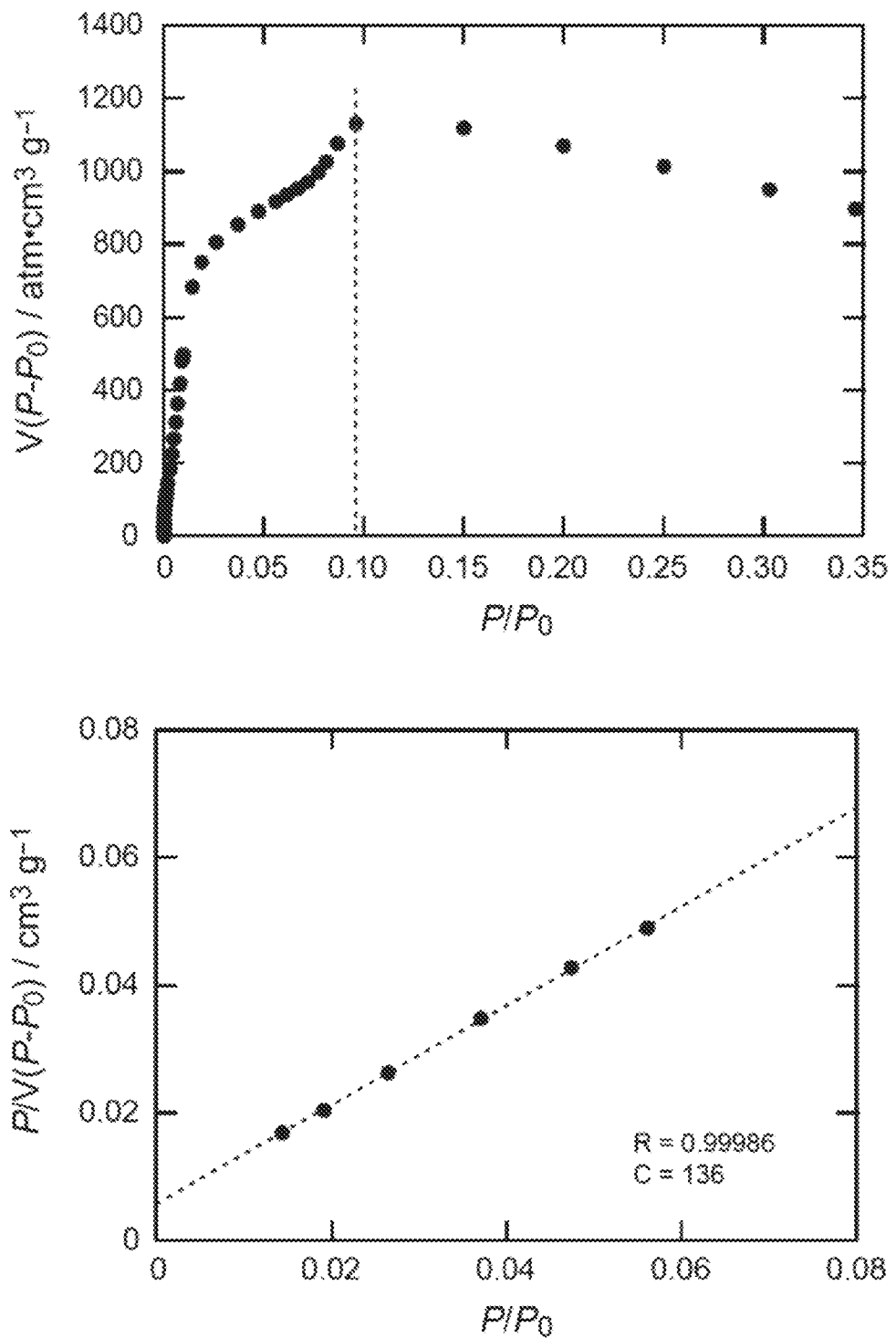
FIG. 31 shows V(P$_0$–P) vs. P/P$_0$ for MOF-205. Only the range below P/P$_0$=0.09 satisfies the first consistency criterion for applying the BET theory. (Bottom) Plot of the linear region for the BET equation.
Figure 32:
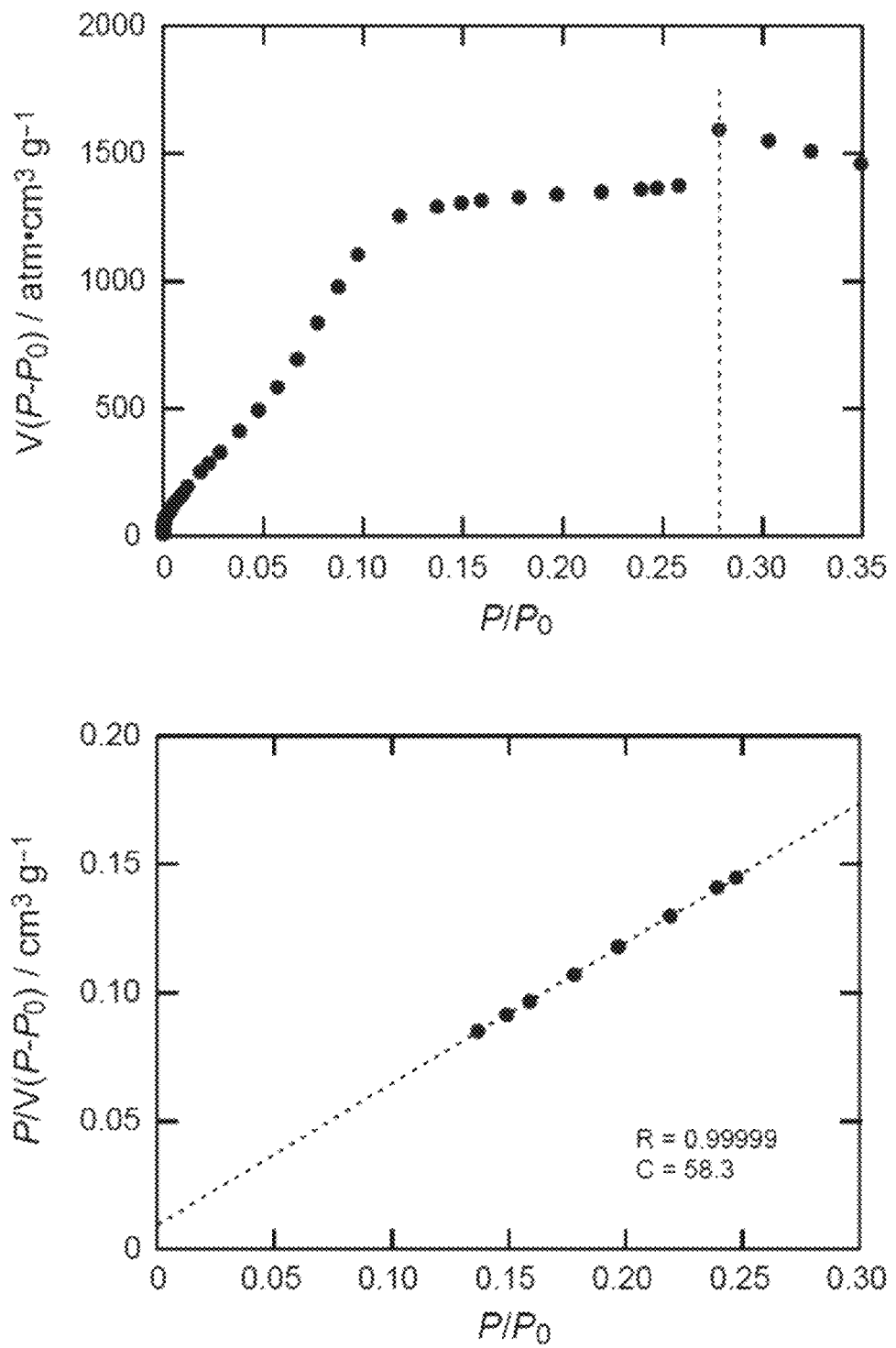
FIG. 32 shows V(P$_0$–P) vs. P/P$_0$ for MOF-210 (top). Only the range below P/P$_0$=0.27 satisfies the first consistency criterion for applying the BET theory. (Bottom) Plot of the linear region for the BET equation.
Figure 33:
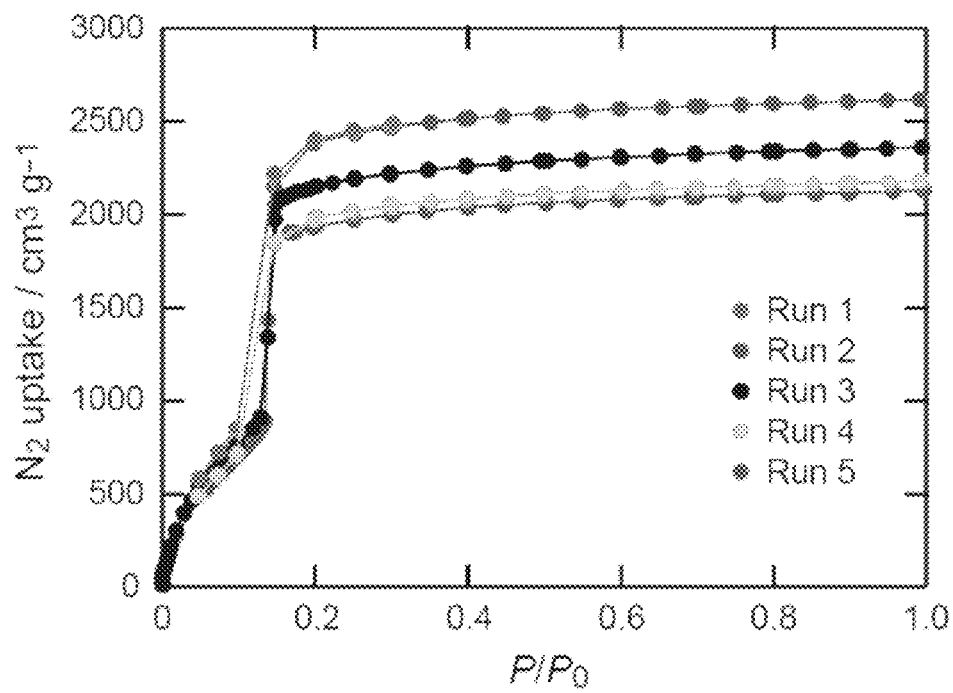
FIG. 33 is a N$_2$ isotherms of independently prepared MOF-200.
Figure 34:
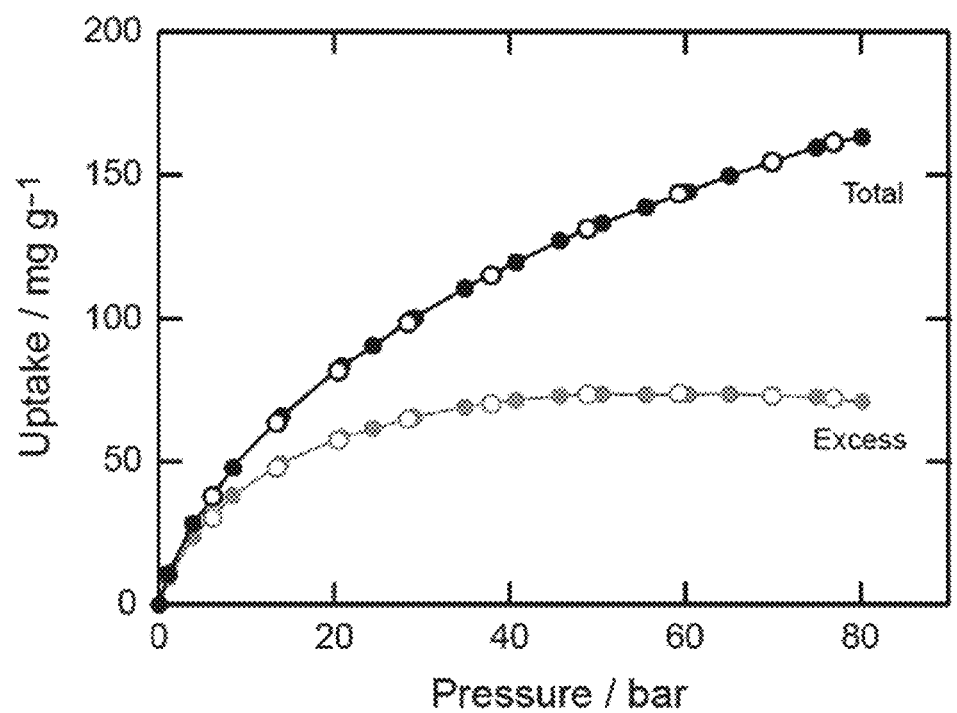
FIG. 34 is a high-pressure H$_2$ isotherms plot for MOF-200 measured at 77 K. Lines represent surface excess and total uptakes, and filled and open symbols represent adsorption and desorption branches.
Figure 35:
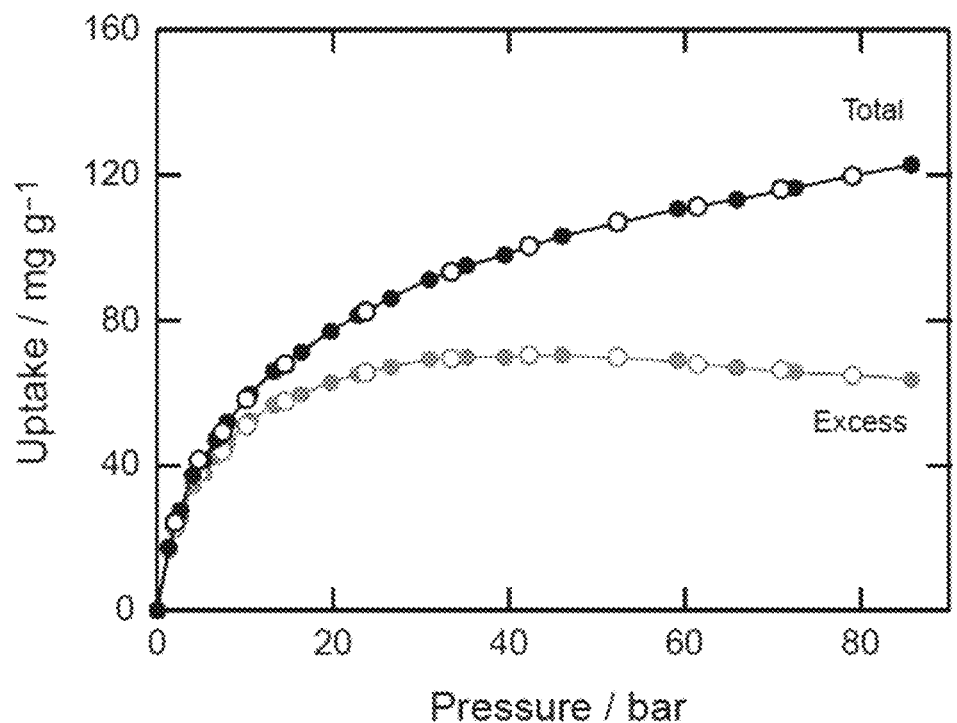
FIG. 35 shows a high-pressure H$_2$ isotherms plot for MOF-205 measured at 77 K. All symbols are the same as in FIG. 34.
Figure 36:
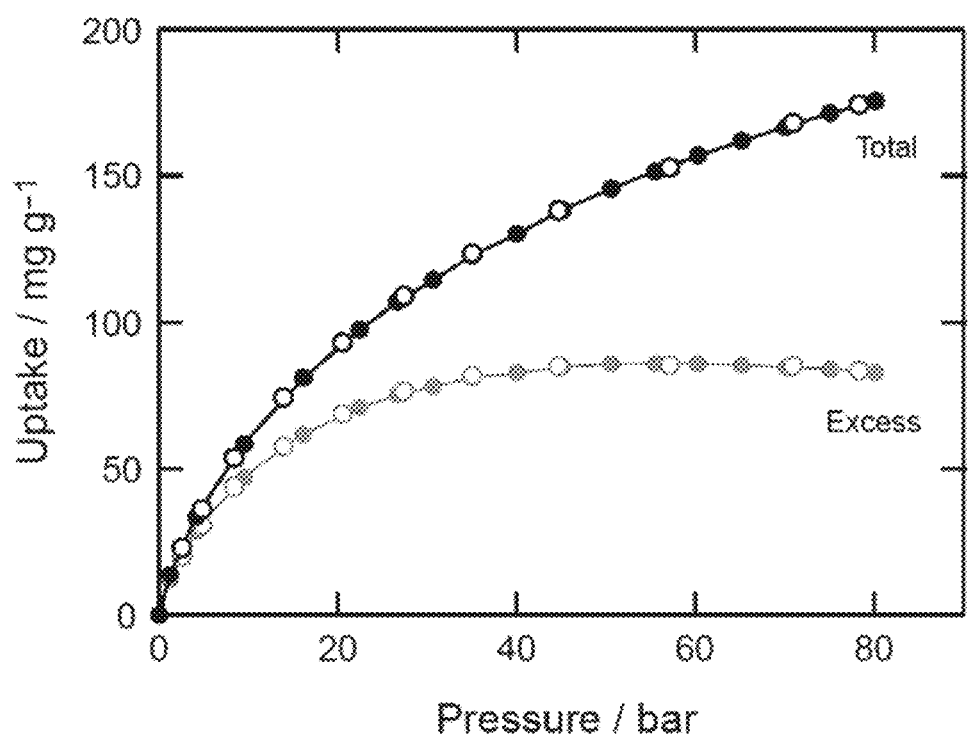
FIG. 36 shows a high-pressure H$_2$ isotherms plot for MOF-210 measured at 77 K. All symbols are the same as in FIG. 34.
Figure 37:
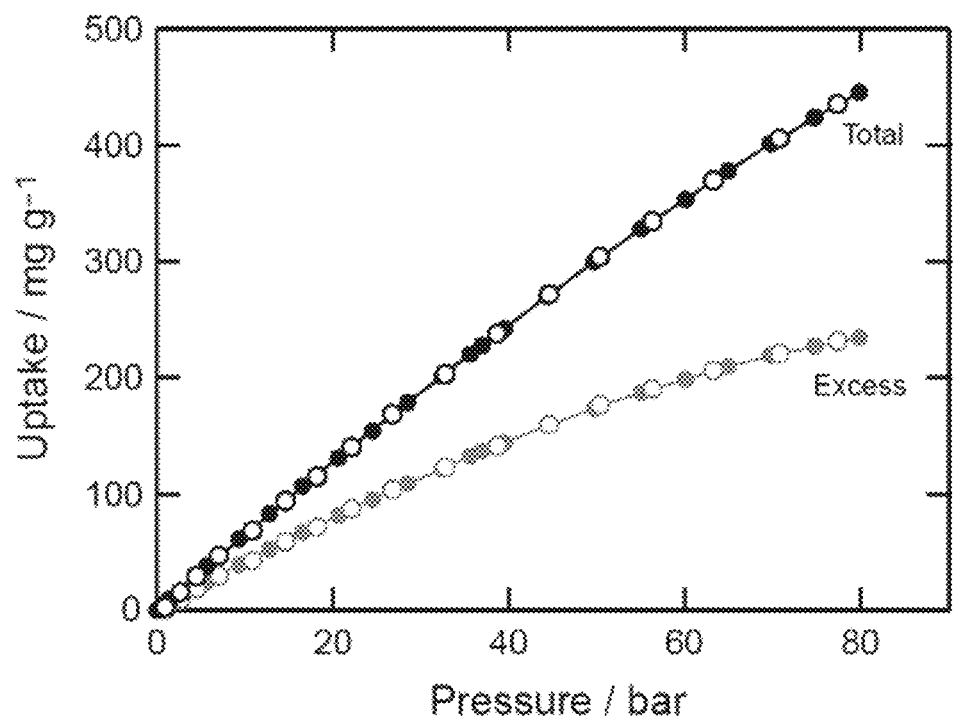
FIG. 37 shows a high-pressure CH$_4$ isotherms for MOF-200 measured at 298 K. All symbols are the same as in FIG. 34.
Figure 38:
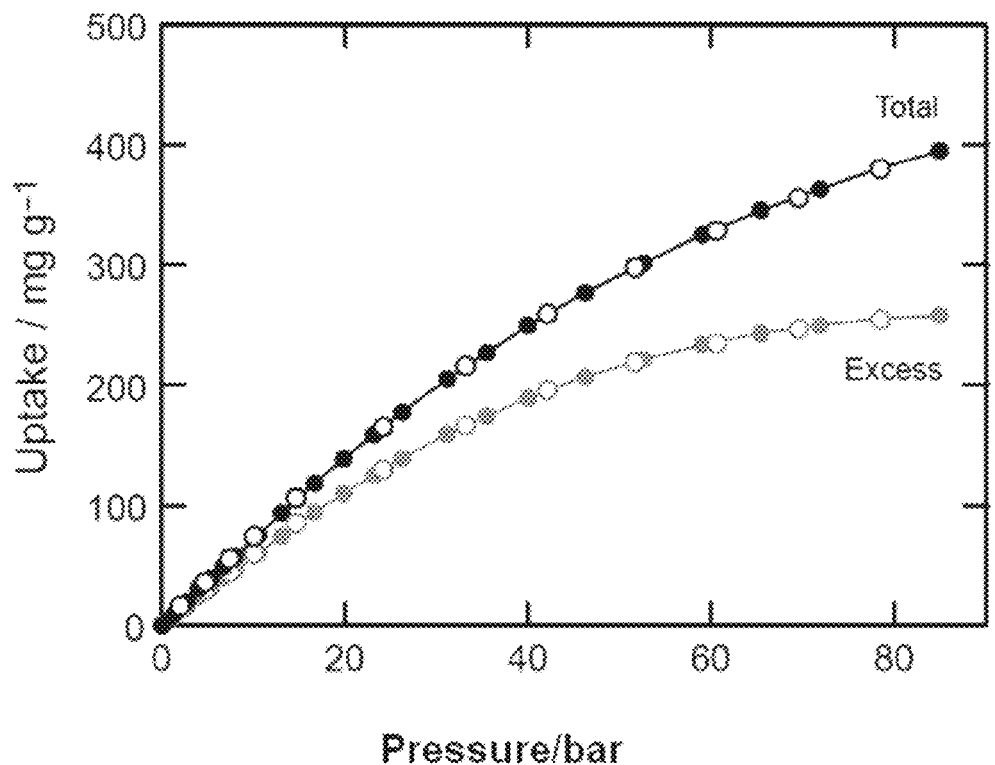
FIG. 38 shows a high-pressure CH$_4$ isotherms plot for MOF-205 measured at 298 K. All symbols are the same as in FIG. 34.
Figure 39:
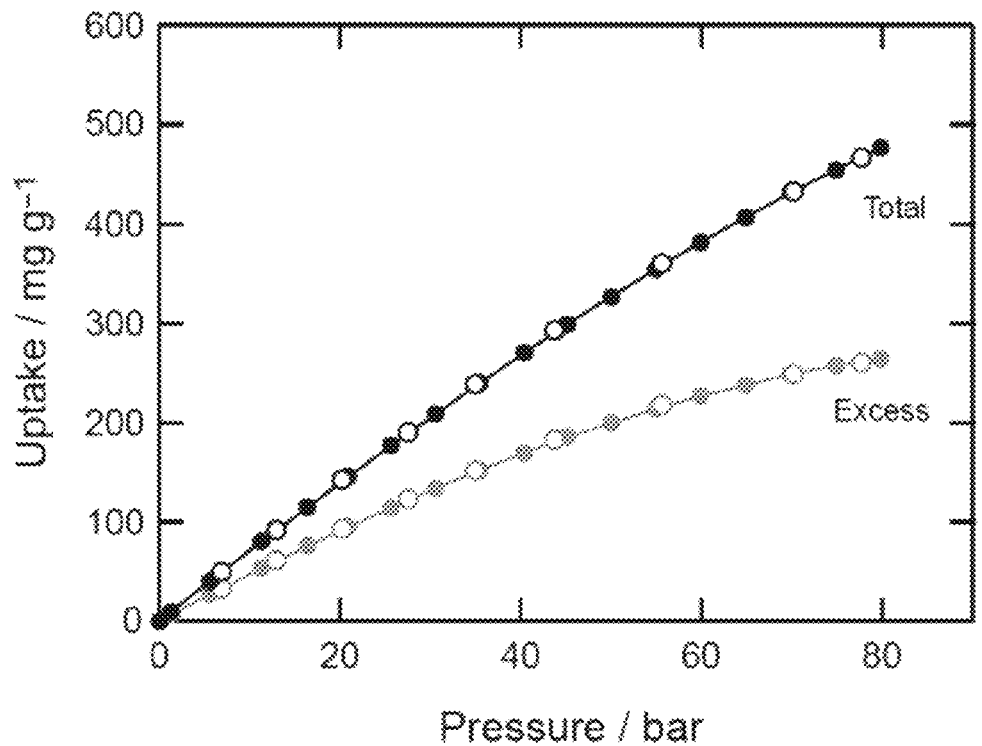
FIG. 39 shows a high-pressure CH$_4$ isotherms plot for MOF-210 measured at 298 K. All symbols are the same as in FIG. 34.
Figure 40:
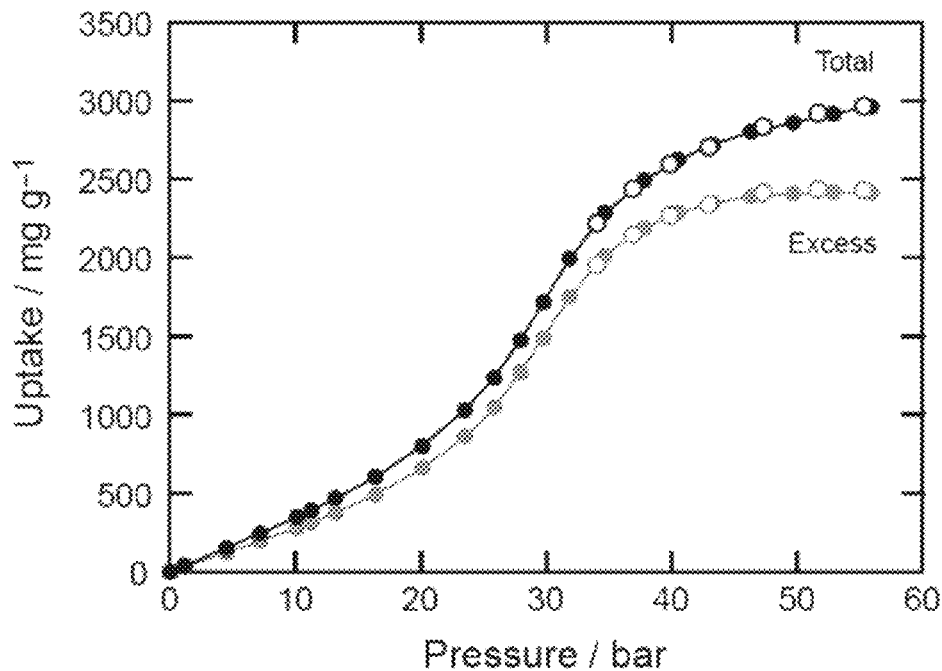
FIG. 40 shows a high-pressure CO$_2$ isotherms plot for MOF-200 measured at 298 K. All symbols are the same as in FIG. 34.
Figure 41:
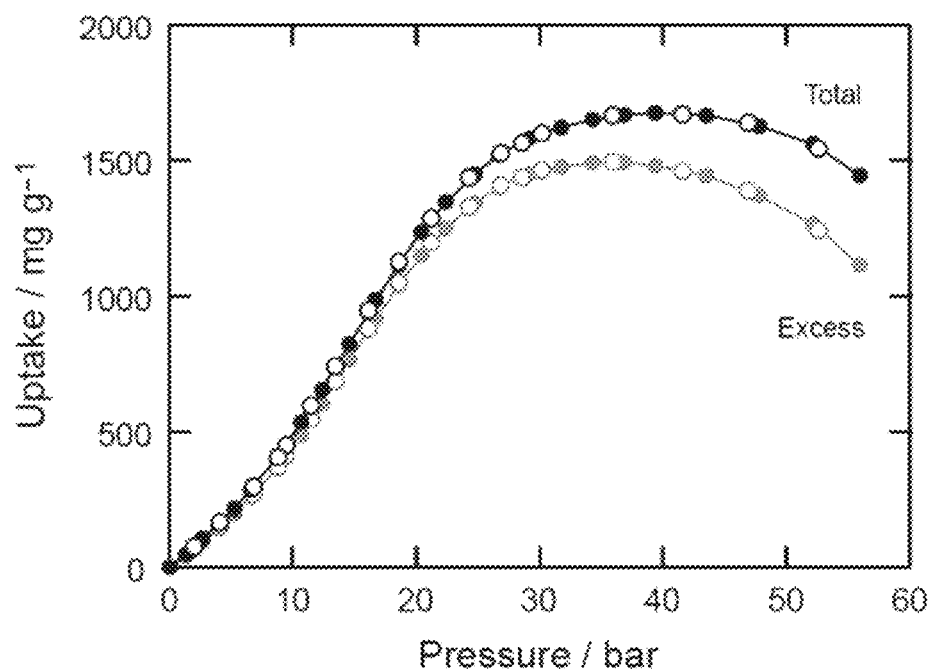
FIG. 41 shows a high-pressure CO$_2$ isotherms plot for MOF-205 measured at 298 K. All symbols are the same as in FIG. 34.
Figure 42:
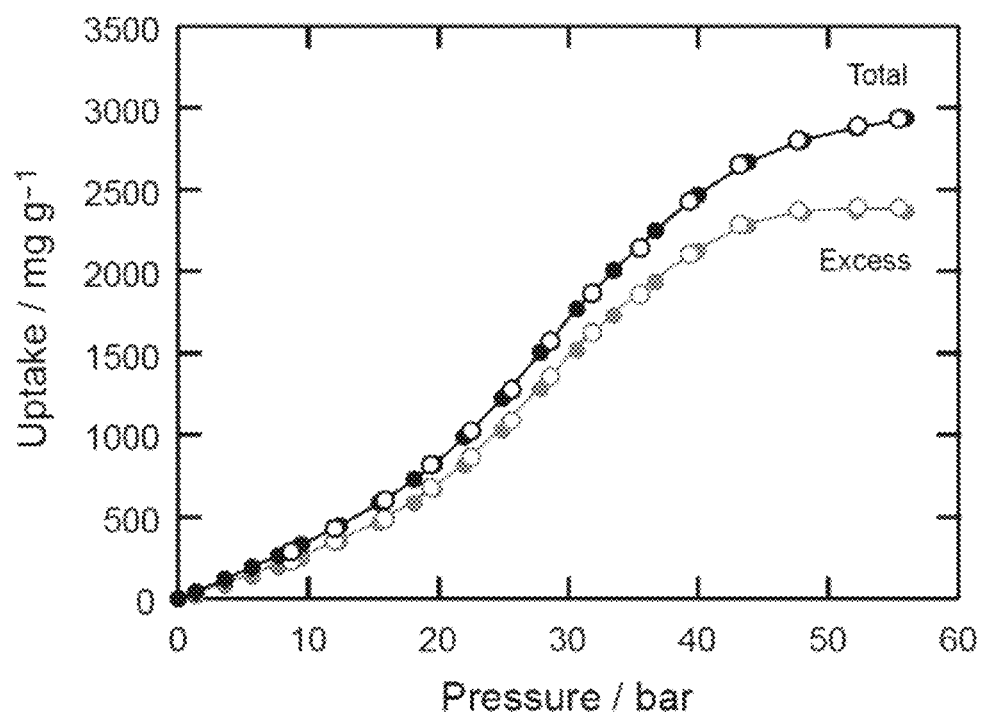
FIG. 42 shows a high-pressure CO$_2$ isotherms for MOF-210 measured at 298 K. All symbols are the same as in FIG. 34.

DFT calculations. DFT calculations were performed on clusters isolated from the unit cells of MOF-200 and MOF-210, with the atomic coordinates taken from the experimental crystallographic data. These clusters included building units (e.g. metal-oxide corner and the linker) representative of their respective unit cells. Details of structure and atom types on MOF-200 and MOF-210 clusters are shown in FIGS. 24 and 25, respectively. All DFT calculations were performed with the Gaussian 03 software using the PBEPBE level of theory and the 6-31G* basis set, and partial atomic charges were extracted using the ChelpG method by fitting them to reproduce the electrostatic potential generated by the DFT calculations. Resulting partial charges for MOF-200 and MOF-210 are given in Tables 6 and 7, respectively.

Grand canonical Monte Carlo (GCMC) simulations and interaction potential. The interaction energy between the atoms was computed through the Lennard-Jones (LJ) and Coulomb potentials $$V_{ij} = 4\varepsilon_{ij}\left[\left(\frac{\sigma_{ij}}{r_{ij}}\right)^{12} - \left(\frac{\sigma_{ij}}{r_{ij}}\right)^{6}\right] + \frac{q_i q_j}{4\varepsilon_0 r_{ij}}$$

where i and j are interacting atoms, and $r_{ij}$ is the distance between atoms i and j. $\epsilon_{ij}$ and $\sigma_{ij}$ are the LJ well depth and diameter, respectively. $q_i$ and $q_j$ are the partial charges of the interacting atoms, and $\epsilon_0$ is the dielectric constant. LJ parameters between different types of sites were calculated using the Lorentz-Berthelot mixing rules.

MOF Models. LJ parameters for MOF-200 and MOF-210 atoms were taken from the DREIDING force field. Partial charges for MOF atoms were derived from DFT calculations as explained above. Table 8 shows the LJ parameters for all atom types found in MOF-200 and MOF-210.

TABLE 6

Partial atomic charges for MOF-200 atoms.

| | Atom No | | | | | |
|---|---|---|---|---|---|---|
| | 1 | 2 | 3 | 4 | 5 | 6 |
| Charge (e) | 1.225 (Zn) | −1.390 (O) | −0.603 (O) | 0.560 (C) | 0.076 (C) | −0.174 (C) |
| | Atom No | | | | | |
| | 7 | 8 | 9 | 10 | 11 | 12 |
| Charge (e) | −0.154 (C) | 0.055 (C) | 0.036 (C) | −0.143 (C) | −0.167 (C) | 0.067 (C) |
| | Atom No | | | | | |
| | 13 | 14 | 15 | 16 | 17 | 18 | 19 |
| Charge (e) | 0.051 (C) | −0.196 (H) | 0.150 (H) | 0.138 (H) | 0.132 (H) | 0.136 (H) | 0.136 (H) |

TABLE 7

Partial atomic charges for MOF-210 atoms.

| | Atom No. | | | | | |
|---|---|---|---|---|---|---|
| | 1 | 2 | 3 | 4 | 5 | 6 |
| Charge (e) | 1.406 (Zn) | −1.592 (O) | −0.679 (O) | −0.679 (O) | 0.622 (C) | 0.046 (C) |
| | Atom No. | | | | | |
| | 7 | 8 | 9 | 10 | 11 | 12 |
| Charge (e) | −0.159 (C) | −0.166 (C) | 0.194 (C) | −0.136 (C) | −0.115 (C) | 0.195 (C) |
| | Atom No. | | | | | |
| | 13 | 14 | 15 | 16 | 17 | 18 |
| Charge (e) | −0.254 (C) | 0.625 (C) | 0.027 (C) | −0.135 (C) | −0.162 (C) | 0.060 (C) |
| | Atom No. | | | | | |
| | 19 | 20 | 21 | 22 | 23 | |
| Charge (e) | 0.154 (H) | 0.150 (H) | 0.178 (H) | 0.143 (H) | 0.139 (H) | |

TABLE 8

LJ paramaters for MOF-200 and MOF-210 atoms.

| Atom type | σ (Å) | ε/k₃ (K) |
|---|---|---|
| C | 3.473 | 47.856 |
| O | 3.033 | 48.158 |
| H | 2.846 | 7.649 |
| Zn | 4.045 | 27.677 |

Nitrogen Model. Nitrogen molecule was modeled using the TraPPE force field. This force field was originally fit to reproduce the vapor-liquid coexistence curve of nitrogen. In this force field nitrogen molecule is a rigid structure where the N—N bond length is fixed at its experimental value of 1.10 Å. This model also reproduces the experimental gas-phase quadrupole moment of nitrogen by placing partial charges on N atoms and on a point located at the center of mass (COM) of the nitrogen molecule. Table 9 shows the LJ parameters and partial charges for nitrogen.

TABLE 9

LJ parameters and partial charges for the sites in the nitrogen molecule.

| | σ (Å) | ε/k₃ (K) | q (e) |
|---|---|---|---|
| N | 3.31 | 36.0 | −0.482 |
| N₂ COM | 0 | 0 | 0.964 |

General GCMC simulation settings. All GCMC simulations included a 10000 cycle equilibration period followed by a 10000 cycle production run. A cycle consists of n Monte Carlo steps; where n is equal to the number of molecules (which fluctuates during a GCMC simulation). All simulations included random insertion/deletion, translation and rotation moves of nitrogen molecules with equal probabilities. MOF atoms were held fixed at their crystallographic positions. An LJ cutoff distance of 12.5 Å was used for all simulations. The Ewald sum technique was used to compute the electrostatic interactions. One unit cell of MOF-200 or MOF-210 (Rhombohedral representation) was used for the simulations. Nitrogen isotherms were simulated at 77 K up to 0.9 bar. Fugacities needed to run the GCMC simulations were calculated using the Peng-Robinson equation of state. All simulated adsorption data reported in this work are the excess quantities, as it is the proper quantity for comparison with experimental data as explained elsewhere.

TABLE 10

Simulated surface areas and pore volume of MOFs.

| | BET SA/m² g⁻¹ | Langmuir SA/m² g⁻¹ | Pore volume/cm³ g⁻¹ |
|---|---|---|---|
| MOF-200 | 6260 | 12040 | 4.19 |
| MOF-210 | 6580 | 10450 | 3.63 |

Geometric Surface Area Calculations. Geometric surface areas of the MOFs listed in Table 1 were calculated by rolling a sphere probe over the framework atoms as explained in the work of Düren et al. The probe diameter was equal to the van der Waals diameter of nitrogen, which is 3.72 Å. The diameters of the framework atoms were also set to their van der Waals diameters (Table 11) which were calculated by multiplying their Lennard-Jones well depth diameters, σ, by 2^(1/6). The σ values of all framework atoms were taken from the DREIDING force field except for the Cu and Cr atoms, which were taken from the Universal Force Field (UFF).

TABLE 11

Van der Waals diameters of the framework atoms of MOFs listed in Table 1.

| Atom type | van der Waals diameter (Å) |
|---|---|
| C | 3.898 |
| O | 3.404 |
| H | 3.195 |
| N | 3.663 |
| S | 4.030 |
| Zn | 4.540 |
| Cu | 3.495 |
| Cr | 3.023 |

Gas Adsorption Analyses. As-synthesized sample of MOF-205 were immersed in dichloromethane for 3 days; during the exchange the dichloromethane was refreshed three times. The resulting dichloromethane-exchanged sample of MOF-205 was transferred as a suspension to a quartz cell and the solvent was decanted. The wet sample was then evacuated ($10^{-3}$ Torr) at room temperature for 10 h then at 100° C. for 12 h.

As-synthesized samples of MOF-200 and 210 were immersed in DEF and dichloromethane for 3 days, respectively, during which the activation solvent was decanted and freshly replenished three times. Obtained samples were immersed in acetone for 12 h, during which the activation solvent was replenished more than five times. The sample was evacuated with supercritical $CO_2$ in a Tousimis Samdri PVT-3D critical point dryer. Briefly, the acetone-containing sample was placed in the chamber and acetone was completely exchanged with liquid $CO_2$. After that the chamber containing the sample and liquid $CO_2$ was heated up around 40° C. and kept under the supercritical condition (typically 1300 psi) for 1 h. The $CO_2$ was slowly vented (ca. 1 h) from the chamber at around 40° C., yielding porous material.

Low-pressure gas adsorption measurements. Low-pressure gas adsorption experiments (up to 760 torr) were carried out on a Quantachrome AUTOSORB-1 automatic volumetric instrument. Ultrahigh-purity-grade $N_2$ and He gases were used in all adsorption measurements. The N2 (77 K) isotherms were measured using a liquid nitrogen bath (77 K).

BET surface area of MOFs. A BET surface area was obtained by using the data points on the adsorption branch of the $N_2$ isotherm. The BET surface area for MOF-200, 205, and 210 were calculated to be 4530, 4460, and 6240 m² g⁻¹, respectively.

TABLE 12

Porosity data of highly porous MOFs.

| Compound | RCSR code | Linker | Void volume (%) | Crystal density (g cm$^{-3}$) | $A_{BET}$‡ (m$^2$ g$^{-1}$) | $A_{Lang}$‡ (m$^2$ g$^{-1}$) | $A_{geo}$‡‡ (m$^2$ g$^{-1}$) | $V_p$‡ (cm$^3$ g$^{-1}$) | Reference |
|---|---|---|---|---|---|---|---|---|---|
| MOF-5 | pcu | BDC | 79 | 0.59 | 2860 | 3480 | 3390 | 1.22 | This work |
|  |  |  |  |  | 3800¶ | 4400¶ |  | 1.55¶ |  |
| MOF-177 | qom | BTB | 83 | 0.43 | 4500 | 5340 | 4740 | 1.89 | (S31) |
| MOF-180 | qom | BTE | 89 | 0.25 | ND | ND | 6080 | ND | This work |
| MOF-200 | qom | BBC | 90 | 0.22 | 4530 | 10400 | 6400 | 3.59 | This work |
| MOF-205 | ith-d | BTB, NDC | 85 | 0.38 | 4460 | 6170 | 4680 | 2.16 | This work |
| MOF-210 | toz | BTE, BPDC | 89 | 0.25 | 6240 | 10400 | 5850 | 3.60 | This work |
| UMCM-2 | umt | BTB, T2DC‡ | 83 | 0.40 | 5200 | 6060 | 4360 | 2.32 | (S32) |
| NOTT-112 | ntt | TDBB‡ | 80 | 0.48 | 3800 | ND | 3950 | 1.67 | (S33) |
| PCN-14 | nbo | ADIP‡ | 66 | 0.83 | 1750 | 2180 | 1860 | 0.87 | (S34) |
| MIL-101c | mtn-e | BDC | 83 | 0.44 | 4230 | 5900 | 2880 | 2.15 | (S35, S36) |

ND, no data.
‡Acronyms; $A_{BET}$, $A_{Lang}$, and $A_{geo}$ are the BET, Langmuir, and geometric surface areas;
$V_p$ is the measured pore volume;
$H_2$T2DC = thieno[3,2-b]thiophene-2,5-dicarboxylic acid, $H_6$TDBB = 1,3,5-tris(3',5'-dicarboxy[1,1'-biphenyl]-4-yl-)benzene;
$H_4$ADIP = 5,5'-(9,10-anthracenediyl)di-isophthalic acid.
†See Section S6.
¶Values taken from Ref. S37.

High-pressure gas adsorption measurements. High-pressure gas adsorption isotherms for MOF-205 were gravimetrically recorded on a GHP-300 gravimetric high-pressure analyzer from VTI Corporation (currently TA Instruments). To obtain the excess adsorption isotherm, all data points were corrected for buoyancy and the thermal gradient that arises between the balance and the sample bucket. For MOF-200 and 210 equilibrium gas adsorption isotherms were measured using the static volumetric method in an HPA-100 from the VTI Corporation (currently Particulate Systems). Ultra-high-purity grade $H_2$, $CH_4$, He (99.999% purity), and $CO_2$ gases (99.995% purity) were used throughout the high-pressure adsorption experiments. When $H_2$ gas was used, water and other condensable impurities were removed with a liquid nitrogen trap.

Estimation of total gas uptake. Although the surface excess mass is a useful concept, from the viewpoint of gas storage, the total amount that a material can store is more relevant. However, at high temperatures and pressures (i.e., above the critical point of gases), the density profile of the adsorbed phase becomes more diffused and, therefore, it is not possible to distinguish between the adsorbed and bulk phases with the present techniques. In this situation the surface excess is the only experimentally accessible quantity, and there is not a reliable method to estimate the absolute adsorbed amount with high accuracy, although many efforts have been devoted to resolve this issue. Therefore, the absolute amount of hydrogen adsorbed was estimated using a simple equation: (total uptake)=(excess uptake)+(bulk density of gas)×(pore volume).

Needless to say, the volumetric gas uptake (e.g., g L$^{-1}$ unit) is also influenced by the packing factor of the crystalline materials. The packing density is influenced by both shape and size of the materials and usually is below unity, although these numbers for MOFs are not available here. Indeed, the volumetric uptake should be 10-25% smaller compared to the data in Table 13, if the packing density is 0.7.

TABLE 13

Summary of high-pressure adsorption measurements for MOFs.

| | $H_2$ at 77 K and 80 bar | | | $CH_4$ at 298 K and 80 bar | | | $CO_2$ at 298 K and 50 bar | | |
|---|---|---|---|---|---|---|---|---|---|
| Compound | Excess‡ (mg g$^{-1}$) | Total (mg g$^{-1}$) | Total† (g L$^{-1}$) | Excess (mg g$^{-1}$) | Total (mg g$^{-1}$) | Total† (g L$^{-1}$) | Excess‡ (mg g$^{-1}$) | Total (mg g$^{-1}$) | Total† (g L$^{-1}$) |
| MOF-5 | 53 | 82 | 48 | 165 | 250 | 148 | 864 | 1030 | 608 |
|  | 76 | 106 | 63 | ND | ND | ND | ND | ND | ND |
| MOF-177 | 73 | 116 | 50 | 243 | 345 | 147 | 1356 | 1550 | 662 |
| MOF-200 | 74 | 163 | 36 | 234 | 445 | 99 | 2437 | 2830 | 628 |
| MOF-205 | 70 | 120 | 46 | 258 | 380 | 145 | 1495 | 1675 | 638 |
| MOF-210 | 86 | 176 | 44 | 264 | 475 | 118 | 2396 | 2870 | 712 |
| UMCM-2 | 69 | 124 | 50 | ND | ND | ND | ND | ND | ND |
| NOTT-112 | 76 | 107 | 54 | ND | ND | ND | ND | ND | ND |
| PCN-14 | 44 | 67 | 55 | 212* | 222* | 193* | ND | ND | ND |
| MIL-101c | ND | ND | ND | 172 | 295 | 130 | 775 | 1054 | 464 |
| Bulk gas density | NA | NA | 26 | NA | NA | 59 | NA | NA | 131 |

ND, no data;
NA, not applicable.
‡Maximum values were used when isotherms show saturation uptake.
†Crystal density was applied to the gravimetric density.
*Measured at 290 K.

A number of embodiments of the invention have been described. Nevertheless, it will be understood that various modifications may be made without departing from the spirit and scope of the invention. Accordingly, other embodiments are within the scope of the following claims.

What is claimed is:

1. A metal-organic framework (MOF) comprising:
a plurality of metal clusters, wherein each metal cluster comprises one or more metal ions; and
a plurality of at least one first-multidentate aromatic tritopic linking ligands comprising at least one first linking ligand and at least one second linking ligand which is different from the first linking ligand, wherein the linking ligands connect adjacent metal clusters, and wherein the plurality of linking ligands having a sufficient number of accessible sites for atomic or molecular adsorption such that the surface area of the metal-organic framework is greater than about 5500 m²/g.

2. The MOF of claim 1, wherein each metal cluster comprises 3 or more metal ions.

3. The MOF of claim 1, wherein the plurality of-linking ligands have a sufficient number of accessible sites for atomic or molecular adsorption that the surface area is greater than 6,000 m²/g.

4. The MOF of claim 1, wherein the plurality of linking ligands have a sufficient number of accessible sites for atomic or molecular adsorption that the surface area is greater than about 6,500 m²/g.

5. The MOF of claim 1, wherein the plurality of linking ligands have a sufficient number of accessible sites for atomic or molecular adsorption that the surface area is greater than about 10,000 m²/g.

6. The MOF of claim 1, wherein the metal ion is selected from the group consisting of $Li^+$, $Na^+$, $Rb^+$, $Mg^{2+}$, $Ca^{2+}$, $Sr^{2+}$, $Ba^{2+}$, $Sc^{3+}$, $Ti^{4+}$, $Zr^{4+}$, $Ta^{3+}$, $Cr^{3+}$, $Mo^{3+}$, $W^{3+}$, $Mn^{3+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Ni^{2+}$, $Ni+$, $Pd^{2+}$, $Pd+$, $Pt^{2+}$, $Pt+$, $Cu^{2+}$, $Cu+$, $Au+$, $Zn^{2+}$, $Al^{3+}$, $Ga^{3+}$, $In^{3+}$, $Si^{4+}$, $Si^{2+}$, $Ge^{4+}$, $Ge^{2+}$, $Sn^{4+}$, $Sn^{2+}$, $Bi^{5+}$, $Bi^{3+}$, $Cd^{2+}$, $Mn^{2+}$, $Tb^{3+}$, $Gd^{3+}$, $Ce^{3+}$, $La^{3+}$, $Cr^{4+}$ and combinations thereof.

7. The MOF of claim 1, wherein the plurality of linking ligands is comprised of two or more linking ligands comprised of at least two general structural formulas selected from Formula I, II, IV, VI, or VII:

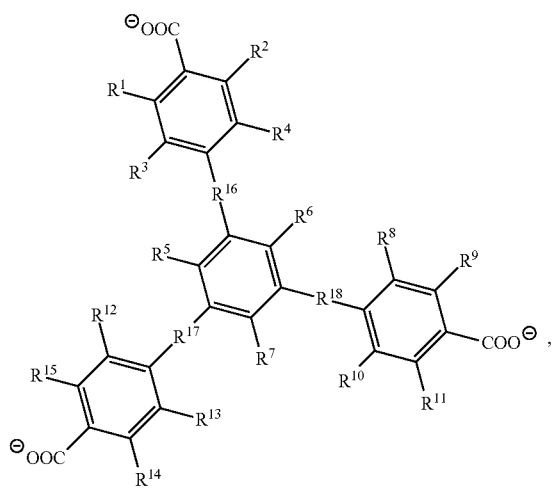

Formula I

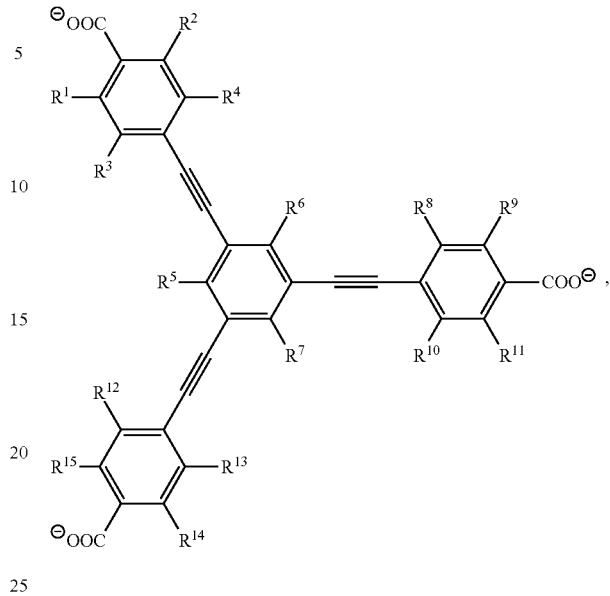

Formula II

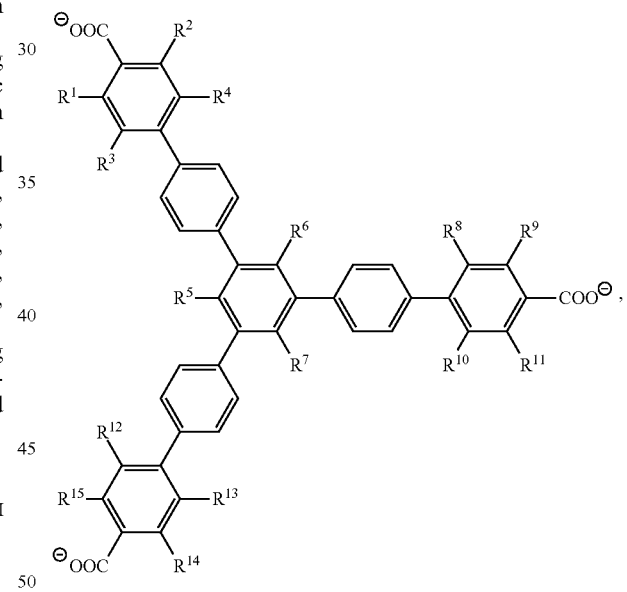

Formula IV

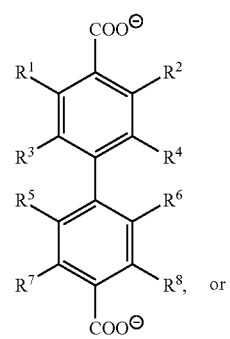

Formula VI or

-continued

Formula VII

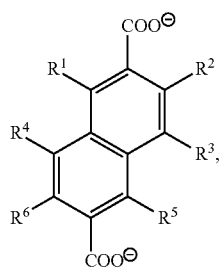

wherein,

R1-R15 are each individually selected from: alkyl, aryl, alkoxy, akenes, alkynes, phenyl, substitutions of the foregoing, sulfur-containing groups, silicon-containing groups, nitrogen-containing groups, oxygen-containing groups, halogen, nitro, amino, cyano, boron-containing groups, phosphorous-containing groups, carboxylic acids, or esters, H, $NH_2$, CN, OH, =O, =S, Cl, I, F,

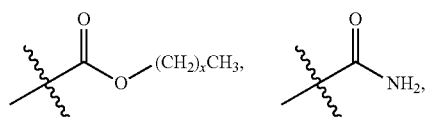

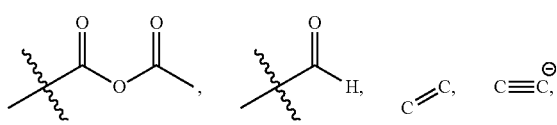

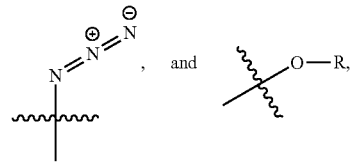

wherein X=1, 2, or 3;

wherein R16, R17 and R18 may or may not be present, if present R16, R17 and R18 are selected from an alkyl or cycloalkyl group, comprising 1 to 20 carbon atoms, an aryl group comprising 1 to 5 phenyl rings, an alkyl or aryl amine comprising alkyl or cycloalkyl groups having from 1 to 20 carbon atoms or aryl groups comprising 1 to 5 phenyl rings, or —C≡C—.

8. The MOF of claim 1, wherein the plurality of linking ligands is comprised of two or more linking ligands comprised of at least two general structural formulas selected from Formula III, V, VIII, or IX:

Formula III

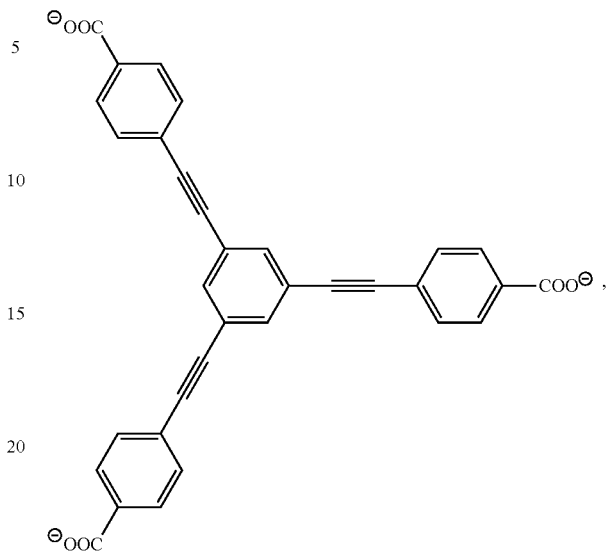

(4,4',4''-(benzene-1,3,5-triyl-tris(ethyne-2,1-diyl)tribenzoate)
(BTE)

Formula V

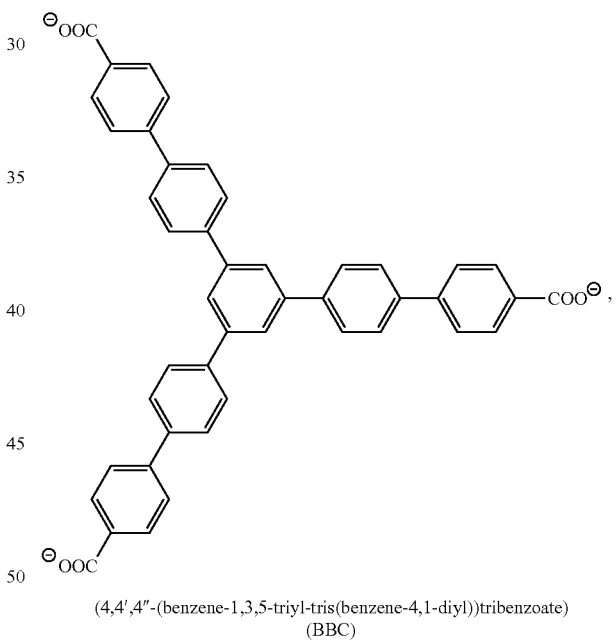

(4,4',4''-(benzene-1,3,5-triyl-tris(benzene-4,1-diyl))tribenzoate)
(BBC)

Formula VIII

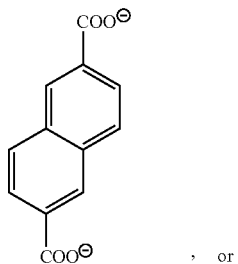, or (2-6-napthalenedicarboxylate)
(NDC)

-continued

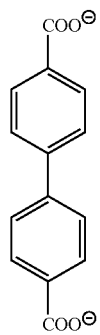

(biphenyl-4,4'-dicarboxylate)
(BPDC)

Formula IX

9. The MOF of claim 1, wherein the at least one first linking ligand has a general formula selected from the group comprising Formula VI, VII, VIII, and IX:

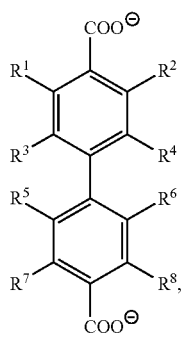

Formula VI

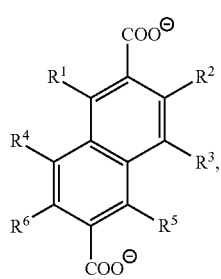

Formula VII

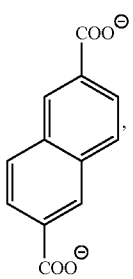

and (2-6-napthalenedicarboxylate)
(NDC)

-continued

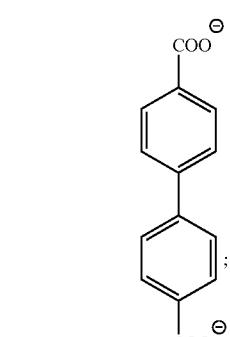

(biphenyl-4,4'-dicarboxylate)
(BPDC)

Formula IX and wherein the at least one second linking ligand has a general formula selected from the group comprising Formula I, II, III, IV, and V:

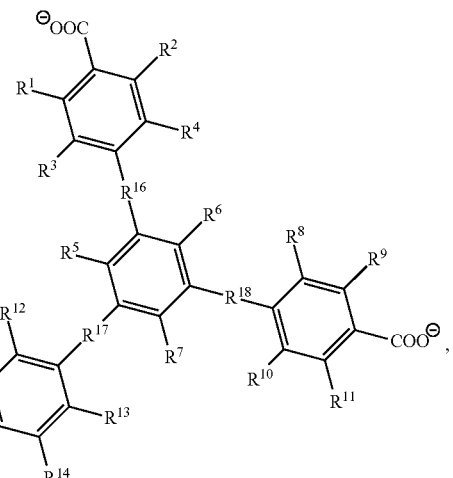

Formula I

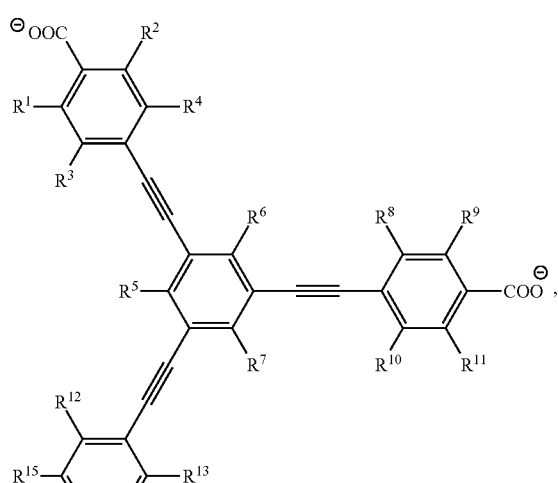

Formula II

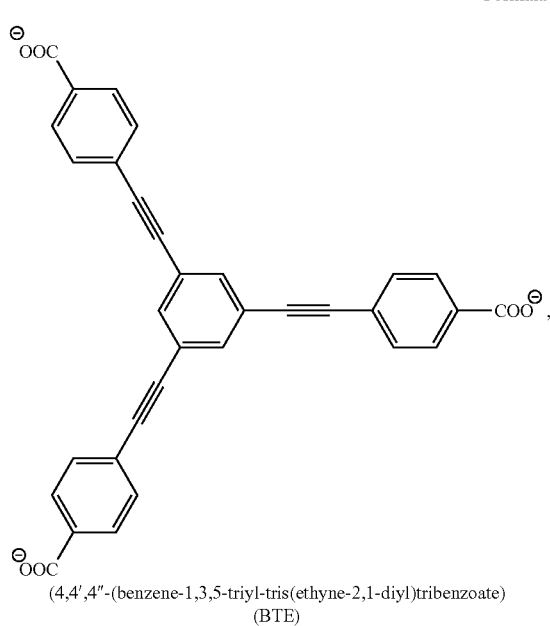
(4,4′,4″-(benzene-1,3,5-triyl-tris(ethyne-2,1-diyl)tribenzoate)
(BTE)
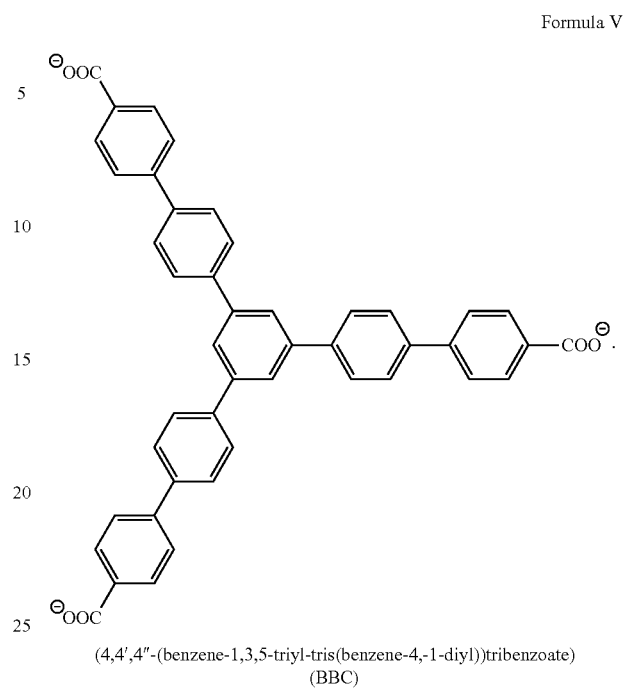
(4,4′,4″-(benzene-1,3,5-triyl-tris(benzene-4,-1-diyl))tribenzoate)
(BBC)
10. The MOF of claim 1, wherein the at least one first linking ligand has a general formula selected from the group comprising Formula VI, VII, VIII, and IX:
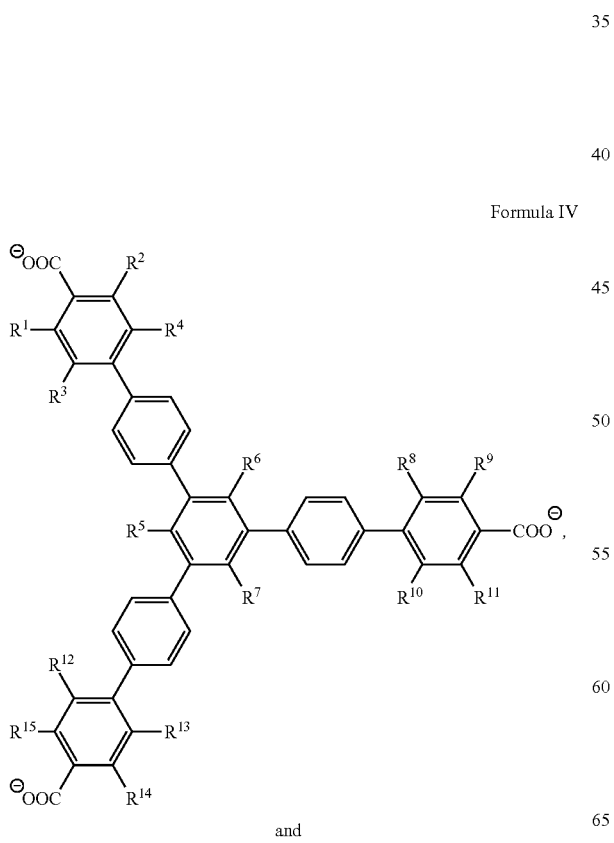
and
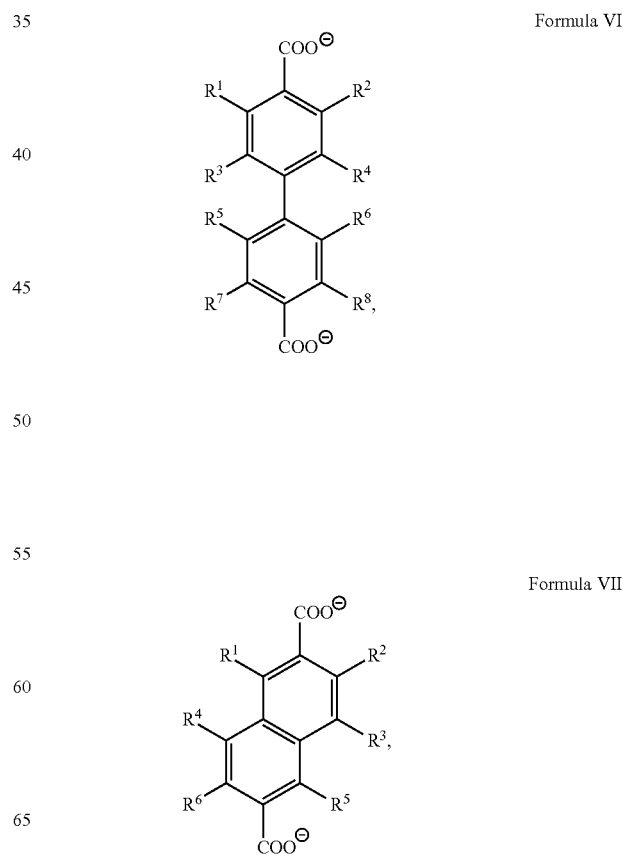

47
-continued

Formula VIII

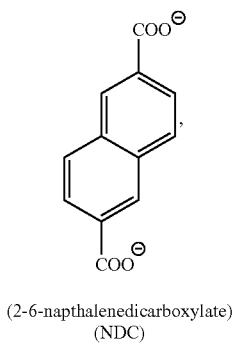

(2-6-napthalenedicarboxylate)
(NDC)

and

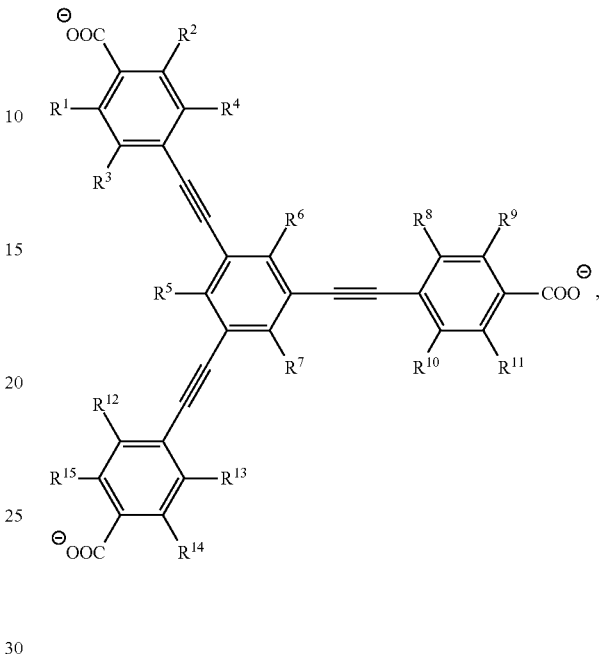

and wherein the at least one second linking ligand is selected from the group consisting of Formula I and II:

Formula I

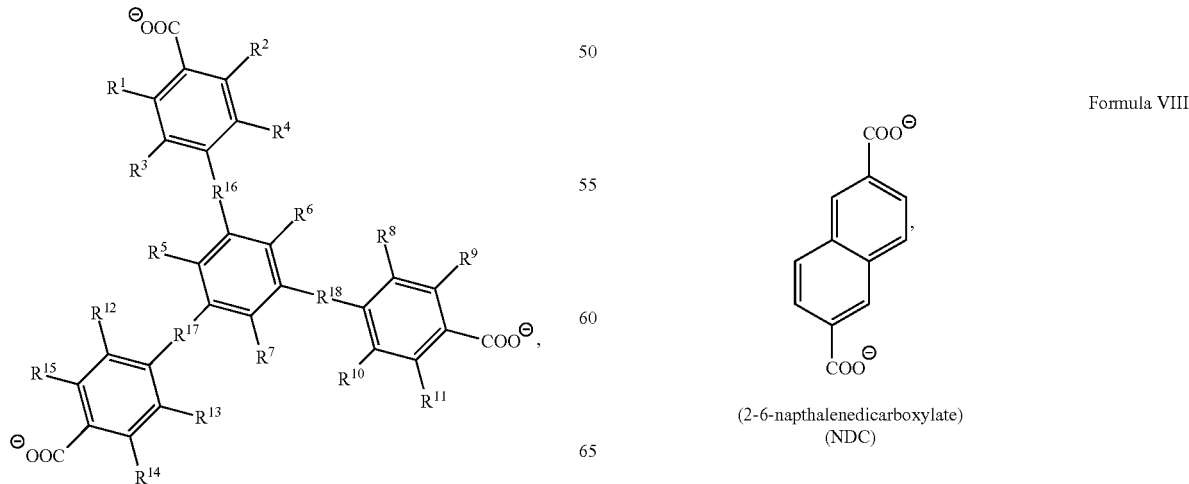

48
-continued

Formula II wherein the structure of Formula I lacks $R^{16}$, $R^{17}$ and $R^{18}$.

11. The MOF of claim 1, wherein the plurality of multidentate aromatic tritopic linking ligands is comprised of a first linking ligand having structural Formula VIII:

Formula VIII (2-6-napthalenedicarboxylate)
(NDC)

and a second linking ligand having structural Formula I:

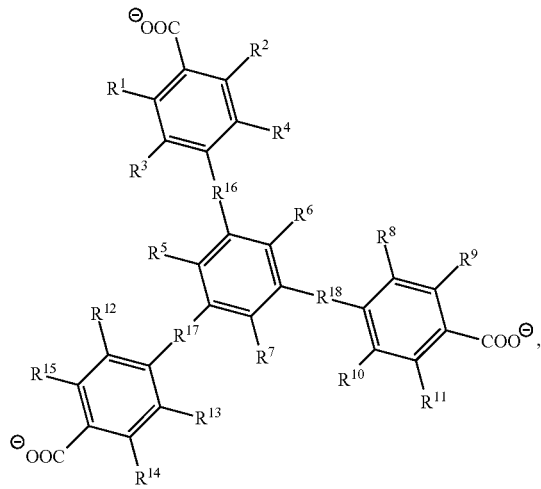

Formula I wherein the structure of Formula I lacks $R^{16}$, $R^{17}$ and $R^{18}$.

12. The MOF of claim 11, wherein the metal-organic framework has the structure and chemical properties of MOF-205.

13. The MOF of claim 1, wherein the plurality of multidentate aromatic tritopic linking ligands is comprised of at least one first linking ligand having structural Formula IX:

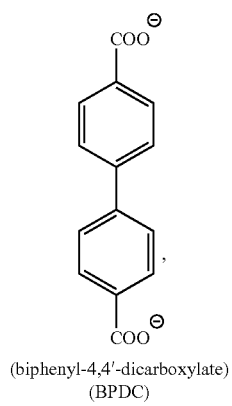

Formula IX (biphenyl-4,4'-dicarboxylate)
(BPDC)

and at least one second linking ligand having structural Formula I

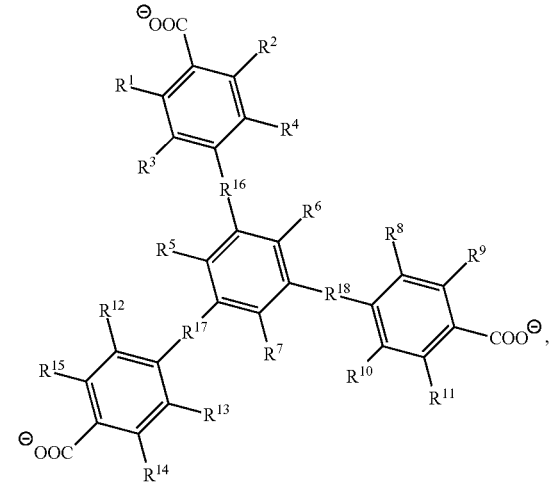

Formula I wherein the structure of Formula I lacks $R^{16}$, $R^{17}$ and $R^{18}$.

14. The MOF of claim 13, wherein the metal-organic framework has the structure and chemical properties of MOF-210.

15. The MOF of claim 6, wherein the metal ion is a metal ion selected from the group consisting of $Mg^{2+}$, $Ca^{2+}$, $Sr^{2+}$, $Ba^{2+}$, $Fe^{2+}$, $Ru^{2+}$, $Os^{2+}$, $Co^{2+}$, $Ni^{2+}$, $Pd^{2+}$, $Pt^{2+}$, $Cu^{2+}$, $Zn^{2+}$, $Si^{2+}$, $Ge^{2+}$, $Sn^{2+}$, $Cd^{2+}$, and combinations thereof.

16. The MOF of claim 6, wherein the metal ion is $Zn^{2+}$.

17. The MOF of claim 1, wherein the plurality of linking ligands comprise at least one linking cluster selected from the group consisting of carboxylate, $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_{4H}$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, $CH(SH)_2$, $C(SH)_3$, $CH(NH_2)_2$, $C(NH_2)_3$, $CH(OH)_2$, $C(OH)_3$, $CH(CN)_2$, and $C(CN)_3$, wherein R is an alkyl group having from 1 to 5 carbon atoms, or an aryl group comprising 1 to 2 phenyl rings.

18. The MOF of claim 17, wherein the plurality of linking ligands comprise carboxylate linking clusters.

19. A method for gas storage and separation comprising contacting the MOF of claim 1 with a fluid wherein an analyte in the fluid interacts and is absorbed by the MOF.

20. A method of forming a MOF, the method comprising: combining a solution comprising a solvent and metal ions selected from the group consisting Group 1 through 16 metals including actinides, and lanthanides, and combinations thereof with at least one first linking ligand comprising the general formula of I-V:

Formula I
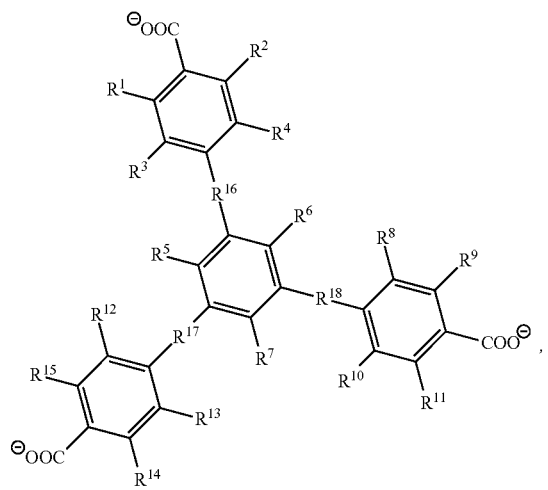
Formula III
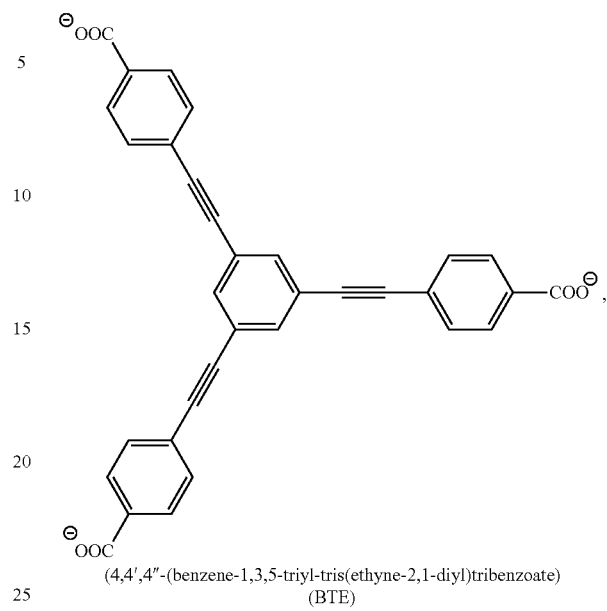
(4,4′,4″-(benzene-1,3,5-triyl-tris(ethyne-2,1-diyl)tribenzoate)
(BTE)
Formula II
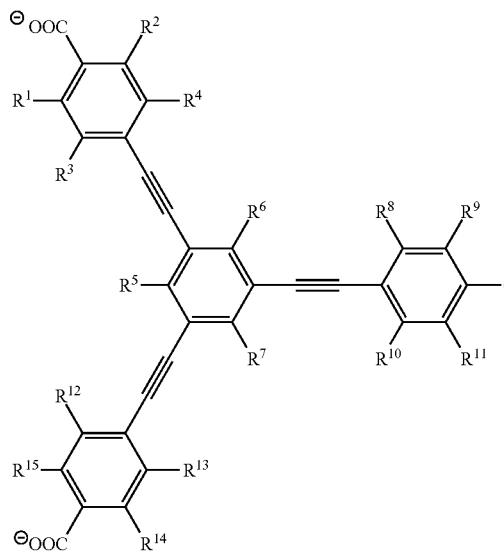
Formula IV
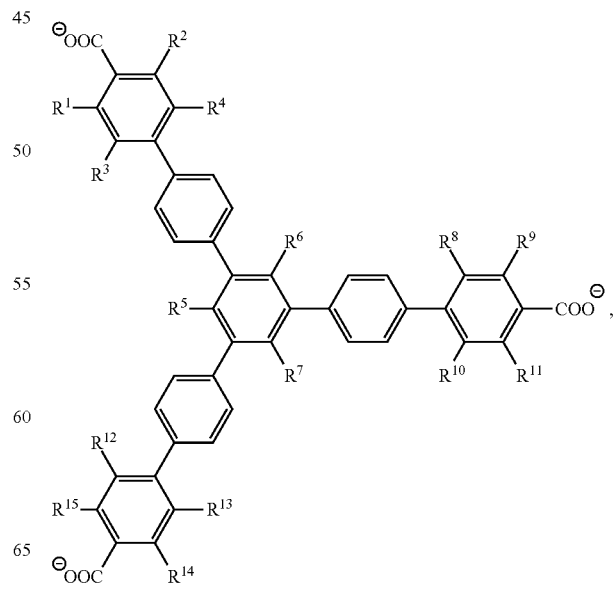

Formula V
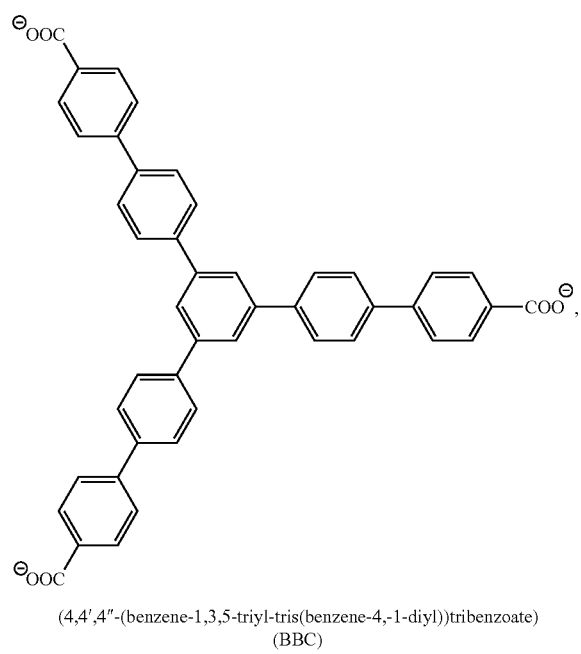
(4,4',4''-(benzene-1,3,5-triyl-tris(benzene-4,-1-diyl))tribenzoate)
(BBC)
and with at least one second linking ligand comprising the general formula VI-IX:
Formula VI
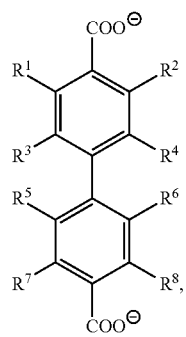
Formula VII
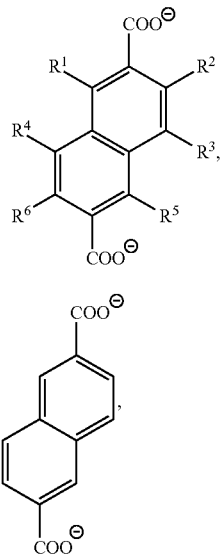
Formula VIII
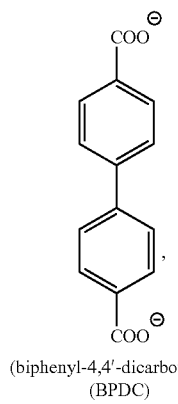
(2-6-napthalenedicarboxylate)
(NDC)
Formula IX
(biphenyl-4,4'-dicarboxylate)
(BPDC)
such that the surface area of the metal-organic framework is greater than 5500 m²/g.
* * * * *